United States Patent [19]

Rorer

[11] Patent Number: 4,514,211

[45] Date of Patent: Apr. 30, 1985

[54] BENZOFURAN AND BENZOTHIOPHENE SULFONAMIDES

[75] Inventor: Morris P. Rorer, Newark, Del.

[73] Assignee: E. I. Du Pont de Nemours and Company, Wilmington, Del.

[21] Appl. No.: 489,099

[22] Filed: Apr. 27, 1983

Related U.S. Application Data

[63] Continuation-in-part of Ser. No. 410,993, Aug. 27, 1982, abandoned, which is a continuation-in-part of Ser. No. 317,183, Oct. 16, 1981, abandoned.

[51] Int. Cl.$^3$ ............... C07D 405/12; C07D 409/12; A01N 47/36

[52] U.S. Cl. ............................. 71/92; 71/93; 544/209; 544/212; 544/219; 544/253; 544/278; 544/320; 544/321; 544/323; 544/324; 544/331; 544/332; 548/265; 548/268

[58] Field of Search .............. 71/92, 93; 544/320, 544/321, 331, 332, 324, 323, 209, 212, 278, 253, 219; 548/265, 268

[56] References Cited

U.S. PATENT DOCUMENTS 4,339,266 7/1982 Levitt ................................ 71/92
4,391,627 7/1983 Levitt ................................ 71/90

Primary Examiner—Robert Gerstl

[57] ABSTRACT

Benzofuran and benzothiophene sulfonamides show utility as herbicides and plant growth regulants.

52 Claims, No Drawings

BENZOFURAN AND BENZOTHIOPHENE SULFONAMIDES

BACKGROUND OF THE INVENTION

This invention relates to benzofuran and benzothiophene sulfonamides which are novel. The compounds of this invention and their agriculturally suitable salts, are useful as agricultural chemicals, e.g., plant growth regulants and herbicides. The invention also includes intermediates useful for making these compounds.

Netherlands Patent No. 121,788, published Sept. 15, 1966, discloses the preparation of compounds of the following Formula and their use as general or selective herbicides:

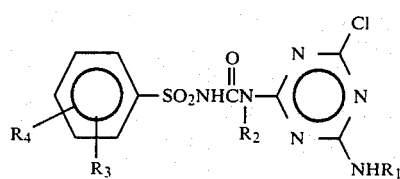

wherein $R_1$ and $R_2$ may independently be alkyl of 1-4 carbon atoms; and $R_3$ and $R_4$ may independently be hydrogen, chlorine or alkyl of 1-4 carbon atoms.

U.S. Pat. No. 3,637,366 discloses compounds having the formula:

R₁HN—⟨⟩—SO₂—NHR₂ wherein $R_1$ is hydrogen or lower saturated aliphatic acyl and $R_2$ is hydrogen, 2-pyrimidinyl, pyridyl, amidino, acetyl or carbamoyl.

The disclosed compounds are said to provide control of crabgrass, cress, endive, clover and *Poa annua*.

French Pat. No. 1,468,747 discloses the following para-substituted phenylsulfonamides as being useful as antidiabetic agents:

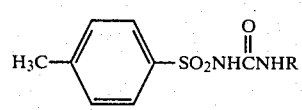

wherein

R=H, halogen, CF₃ or alkyl.

Logemann et al., Chem. Ab., 53, 18052 g (1959), disclose a number of sulfonamides, including uracil derivatives and those having the formula:

H₃C—⟨⟩—SO₂NHCNHR
              ‖
              O wherein

R is butyl, phenyl or

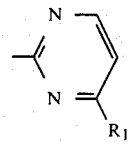

and $R_1$ is hydrogen or methyl.

When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121-5 (1962) [Chem. Ab., 59 1633 e] describes the synthesis of N-[(2,6-dimethoxypyrimidin-4-yl)aminocarbonyl]-4-methylbenzenesulfonamide:

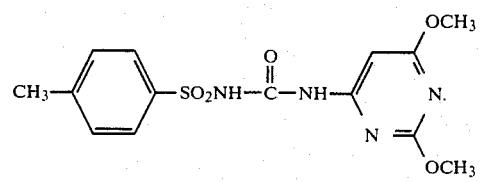

U.S. Pat. No. 4,127,405 teaches compounds which are useful for controlling weeds in wheat having the formula

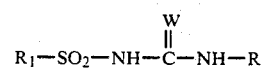

wherein

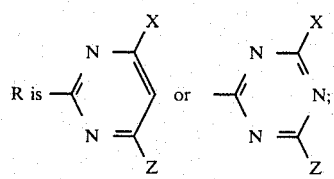

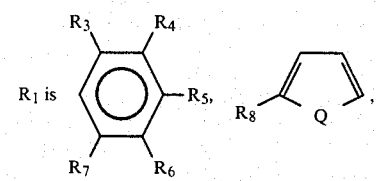

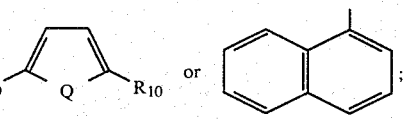

$R_3$ and $R_6$ are independently hydrogen, fluorine, chlorine, bromine, iodine, alkyl of 1-4 carbon atoms, alkoxy of 1-4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1-2 carbon atoms or alkoxy of 1-2 carbon atom;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1-3 carbon atoms, trifluoromethyl, $CH_3S$— or $CH_3OCH_2$—; and Z is methyl or methoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

In addition, U.S. Ser. No. 227,886 teaches o-alkylsulfonylbenzenesulfonylureas which are useful as herbicides.

In U.S. Ser. No. 274,233, there is a disclosure of herbicidal benzo[b]thiophene- and benzofuransulfonylureas in which the sulfonylureido group is bonded to the heterocyclic ring.

The presence of undesired vegetation causes substantial damage to useful crops, especially agricultural products that satisfy man's basic food and fiber needs, such as cotton, rice, corn, wheat, and the like. The current population explosion and concomitant world food and fiber shortage demand improvements in the efficiency of producing these crops. Prevention or minimizing the loss of a portion of such valuable crops by killing, or inhibiting the growth of undesired vegetation is one way of improving this efficiency. A wide variety of materials useful for killing, or inhibiting (controlling) the growth of undesired vegetation is available; such materials are commonly referred to as herbicides. The need still exists however, for more effective herbicides.

SUMMARY OF THE INVENTION

This invention relates to compounds of Formula I, Formula I', Formula II and Formula II' and their agriculturally suitable salts, suitable agricultural compositions containing them, and their use as pre-emergence and/or post-emergence herbicides.

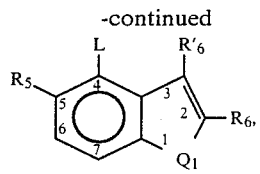

I

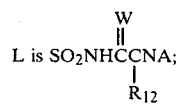

I'

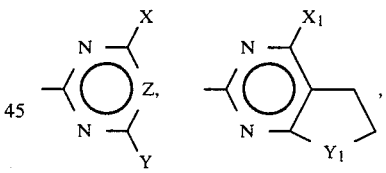

II

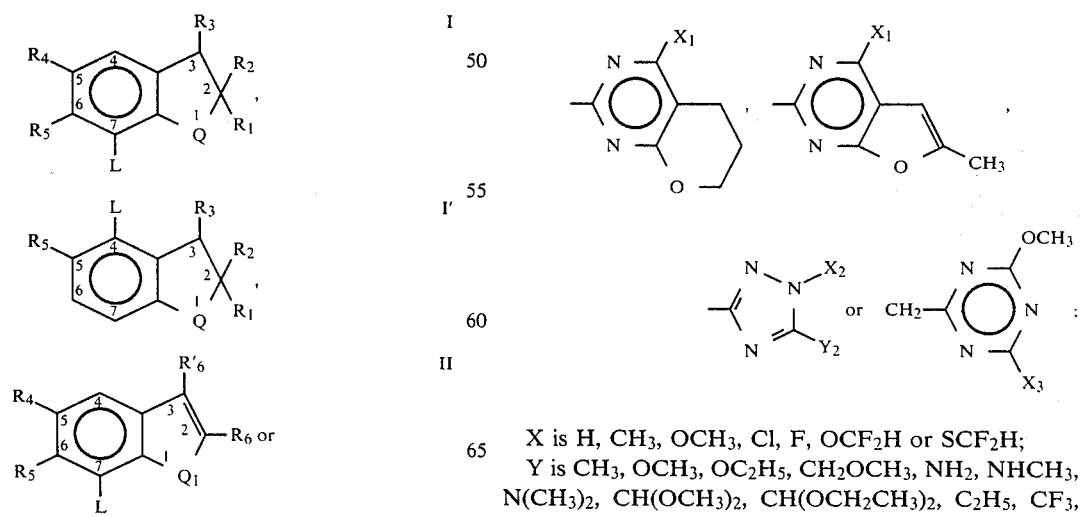

II' wherein

Q is O, S, SO or $SO_2$;

$Q_1$ is O, S or $SO_2$;

L is $SO_2NH\overset{\overset{W}{\|}}{C}N\underset{\underset{R_{12}}{|}}{}A$;

$R_1$ is H or $C_1$-$C_4$ alkyl;

$R_2$ is H or $C_1$-$C_4$ alkyl;

$R_3$ is H or $CH_3$;

$R_4$ is H, Cl, $CH_3$, $CF_3$, $OCH_3$, Br, F, $SCH_3$ or $OCF_2H$;

$R_5$ is H, $CH_3$, $OCH_3$, Cl, Br, $NO_2$, $CO_2R_7$, $SO_2R_8$, $OSO_2R_9$, $SO_2NR_{10}R_{11}$, F, $CF_3$, $SCH_3$, $OCF_2H$ or $SO_2N(OCH_3)CH_3$;

$R_6$ is H, Cl, Br or $C_1$-$C_4$ alkyl;

$R_6'$ is H, $CH_3$, Cl or Br;

$R_7$ is $C_1$-$C_3$ alkyl, $CH_2CH=CH_2$, $CH_2CH_2OCH_3$ or $CH_2CH_2Cl$;

$R_8$ is $C_1$-$C_3$ alkyl;

$R_9$ is $C_1$-$C_3$ alkyl or $CF_3$;

$R_{10}$ and $R_{11}$ are independently $C_1$-$C_2$ alkyl;

$R_{12}$ is H or $CH_3$;

W is O or S;

A is

X is H, $CH_3$, $OCH_3$, Cl, F, $OCF_2H$ or $SCF_2H$;

Y is $CH_3$, $OCH_3$, $OC_2H_5$, $CH_2OCH_3$, $NH_2$, $NHCH_3$, $N(CH_3)_2$, $CH(OCH_3)_2$, $CH(OCH_2CH_3)_2$, $C_2H_5$, $CF_3$, $CH_2=CHCH_2O$,

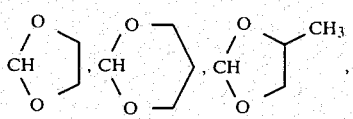

CH≡CCH$_2$O, CF$_3$CH$_2$O, OCH$_2$CH$_2$Cl, OCH$_2$CH$_2$Br, OCH$_2$CH$_2$F, CN, CH$_2$OCH$_2$CH$_3$, OCH$_2$CH$_2$OCH$_3$ or GCF$_2$T wherein G is O or S and T is H, CHClF, CHBrF, CF$_2$H or CHFCF$_3$;

Z is CH, N, CCH$_3$, CC$_2$H$_5$, CCl or CBr;
Y$_1$ is O or CH$_2$;
X$_1$ is CH$_3$, OCH$_3$, OC$_2$H$_5$ or OCF$_2$H;
X$_2$ is CH$_3$, C$_2$H$_5$ or CH$_2$CF$_3$;
Y$_2$ is C$_2$H$_5$, CH$_3$, OCH$_3$, OC$_2$H$_5$, SCH$_3$ or SC$_2$H$_5$; and
X$_3$ is CH$_3$ or OCH$_3$;
provided that
(1) in Formulae II and II', when R$_5$ is NO$_2$, then R$_6$ is C$_1$-C$_4$ alkyl and R$_6$' is CH$_3$;
(2) when X is Cl or F, then Z is CH and Y is OCH$_3$, NH$_2$, NHCH$_3$, N(CH$_3$)$_2$ or OCF$_2$H;
(3) when Q is SO, then W is O;
(4) when R$_4$ is other than H, then R$_5$ is H; and
(5) R$_1$ and R$_2$ taken together are not more than four carbon atoms.

Preferred for reasons of their higher herbicidal activity or more favorable ease of synthesis are:
(1) Compounds of the generic scope of Formula I.
(2) Compounds of Preferred 1 where W is O.
(3) Compounds of Preferred 2 where R$_5$ is H, Cl, CH$_3$, OCH$_3$, CO$_2$R$_7$ or SO$_2$R$_8$, R$_4$ is H, Cl, CH$_3$ or OCH$_3$, and Y is CH$_3$, OCH$_3$, OC$_2$H$_5$, CH$_2$OCH$_3$, NH$_2$, NHCH$_3$, N(CH$_3$)$_2$, CH(OCH$_3$)$_2$,

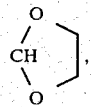

C$_2$H$_5$, CF$_3$, CH$_2$=CHCH$_2$O, HC≡CCH$_2$O, CF$_3$CH$_2$O, OCF$_2$H or SCF$_2$H.
(4) Compounds of Preferred 3 where R$_3$, R$_4$, R$_5$ and R$_{12}$ are H, R$_1$ is H, CH$_3$ or CH$_2$CH$_3$ and R$_2$ is H or CH$_3$.
(5) Compounds of Preferred 4 where A is

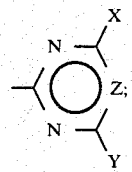

Z is CH or N; and X is CH$_3$, OCH$_3$ or Cl.
(6) Compounds of Preferred 5 where Y is CH$_3$, OCH$_3$, CH$_2$OCH$_3$ or N(CH$_3$)$_2$.
(7) Compounds of the generic scope of Formula I'.
(8) Compounds of Preferred 7 where W is O and Q is S or O.
(9) Compounds of Preferred 8 where R$_5$ is H, Cl, CH$_3$, OCH$_3$, CO$_2$R$_7$ or SO$_2$R$_8$; and Y is CH$_3$, OCH$_3$, OC$_2$H$_5$, CH$_2$OCH$_3$, NH$_2$, NHCH$_3$, N(CH$_3$)$_2$, CH(OCH$_3$)$_2$,

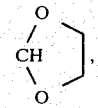

C$_2$H$_5$, CF$_3$, CH$_2$=CHCH$_2$O, HC≡CCH$_2$O, CF$_3$CH$_2$O, OCF$_2$H or SCF$_2$H.
(10) Compounds of Preferred 9 where R$_5$ and R$_{12}$ are H and R$_1$ and R$_2$ are independently H or CH$_3$.
(11) Compounds of Preferred 10 where A is

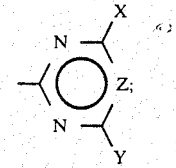

Z is CH or N; and X is CH$_3$, OCH$_3$ or Cl.
(12) Compounds of Preferred 11 where Y is CH$_3$, OCH$_3$, CH$_2$OCH$_3$ or N(CH$_3$)$_2$.
(13) Compounds of the generic scope of Formula II.
(14) Compounds of Preferred 13 where W is O, R$_6$ is H, CH$_3$ or CH$_2$CH$_3$ and R$_6$' is H.
(15) Compounds of Preferred 14 where R$_5$ is H, Cl, CH$_3$, OCH$_3$, CO$_2$R$_7$ or SO$_2$R$_8$, R$_4$ is H, Cl, CH$_3$ or OCH$_3$, and Y is CH$_3$, OCH$_3$, OC$_2$H$_5$, CH$_2$OCH$_3$, NH$_2$, NHCH$_3$, N(CH$_3$)$_2$, CH(OCH$_3$)$_2$,

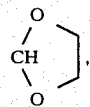

C$_2$H$_5$, CF$_3$, CH$_2$=CHCH$_2$O, HC≡CCH$_2$O, CF$_3$CH$_2$O, OCF$_2$H or SCF$_2$H.
(16) Compounds of Preferred 15 where R$_4$, R$_5$, R$_6$' and R$_{12}$ are H and R$_6$ is H or CH$_3$.
(17) Compounds of Preferred 16 where A is

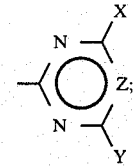

Z is CH or N; and X is CH$_3$, OCH$_3$ or Cl.
(18) Compounds of Preferred 17 where Y is CH$_3$, OCH$_3$, CH$_2$OCH$_3$ or N(CH$_3$)$_2$.
(19) Compounds of the generic scope of Formula II'.
(20) Compounds of Preferred 19 where W is O, Q is O or S, R$_6$ is H or CH$_3$ and R$_6$' is H or CH$_3$.
(21) Compounds of Preferred 20 where R$_5$ is H, Cl, CH$_3$, OCH$_3$, CO$_2$R$_7$ or SO$_2$R$_8$; and Y is CH$_3$, OCH$_3$, OC$_2$H$_5$, CH$_2$OCH$_3$, NH$_2$, NHCH$_3$, N(CH$_3$)$_2$, CH(OCH$_3$)$_2$,

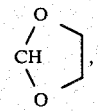

$C_2H_5$, $CF_3$, $CH_2$=$CHCH_2O$, $HC\equiv CCH_2O$, $CF_3CH_2O$, $OCF_2H$ or $SCF_2H$.

(22) Compounds of Preferred 21 where $R_5$ and $R_{12}$ are H.

(23) Compounds of Preferred 22 where A is

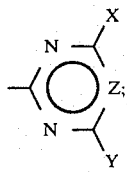

Z is CH or N; and X is $CH_3$, $OCH_3$ or Cl.

(24) Compounds of Preferred 23 where Y is $CH_3$, $OCH_3$, $CH_2OCH_3$ or $N(CH_3)_2$.

Specifically preferred are:
N-[(4,6-dimethylpyrimidin-2-yl)aminocarbonyl]-2,3-dihydro-2-methyl-7-benzothiophenesulfonamide, 1,1-dioxide, m.p. 214°–216°;
N-[(4-methoxy-6-methylpyrimidin-2-yl)aminocarbonyl]-2,3-dihydro-2-methyl-7-benzothiophenesulfonamide, 1,1-dioxide, m.p. 238°–240°;
N-[(4,6-dimethoxypyrimidin-2-yl)aminocarbonyl]-2,3-dihydro-2-methyl-7-benzothiophenesulfonamide, 1,1-dioxide, m.p. 234°–235°;
N-[(4-methoxy-6-methyl-1,3,5-triazin-2-yl)aminocarbonyl]-2,3-dihydro-2-methyl-7-benzothiophenesulfonamide, 1,1-dioxide, m.p. 214°–216°;
N-[(4,6-dimethoxy-1,3,5-triazin-2-yl)aminocarbonyl]-2,3-dihydro-2-methyl-7-benzothiophenesulfonamide, 1,1-dioxide, m.p. 160°–170°;
N-[(4,6-dimethoxypyrimidin-2-yl)aminocarbonyl]-2,3-dihydro-7-benzothiophenesulfonamide, 1,1-dioxide, m.p. 247°–249° C.;
N-[(4,6-dimethoxypyrimidin-2-yl)aminocarbonyl]-2,3-dihydro-2,2-dimethyl-7-benzothiophenesulfonamide, 1,1-dioxide, m.p. 236°–238° C.; and
N-[(4,6-dimethylpyrimidin-2-yl)methylaminocarbonyl]-2,3-dihydro-2-methyl-7-benzothiophenesulfonamide, 1,1-dioxide, m.p. 208°–211° C.

This invention also relates to compounds of Formulae (IIIa) and (IVa) which are useful intermediates for the preparation of the herbicidal compounds of Formula I and II.

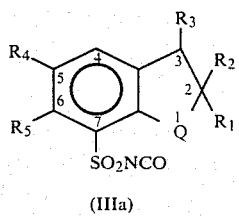

(IIIa)

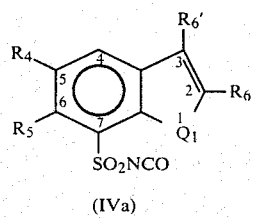

(IVa)

where
Q is O, S or $SO_2$;
$R_1$ is H or $C_1$–$C_4$ alkyl;
$R_2$ is H or $C_1$–$C_4$ alkyl;
$R_3$ is H or $CH_3$;
$R_4$ is H, Cl, Br, F or $CH_3$;
$R_5$ is H, $OCH_3$, $CH_3$, $OSO_2CH_3$ or $OSO_2C_2H_5$;
$Q_1$ is O, S or $SO_2$;
$R_6$ is H or $CH_3$; and
$R_6'$ is H or $CH_3$.

DETAILED DESCRIPTION OF THE INVENTION

Synthesis

As shown in Equations 1 and 2, the compounds of Formulae (I), (I'), (II) and (II') can be prepared by reacting sulfonylisocyanates or isothiocyanates of Formulae (III) and (IV), with an appropriate amine of Formula (V), wherein $R_1$ to $R_6'$, $R_{12}$, A, $Q_1$, Q and W are as previously defined.

Equation 1

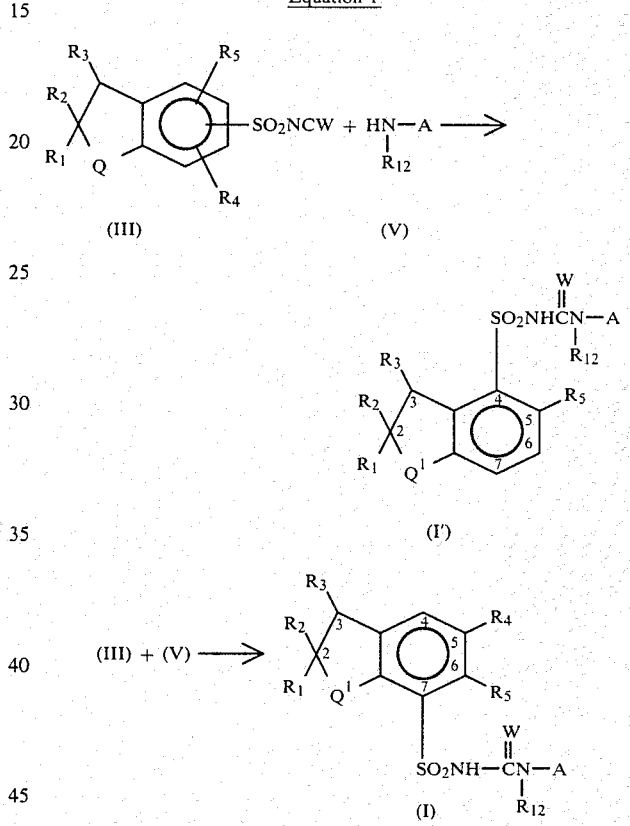

Equation 2

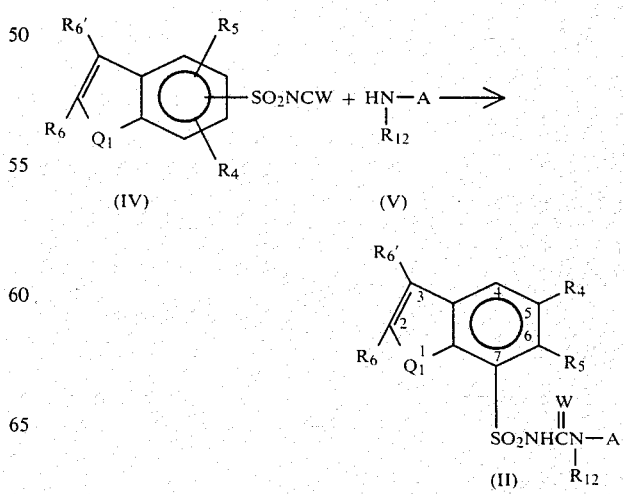

(IV) + (V) ⟶ 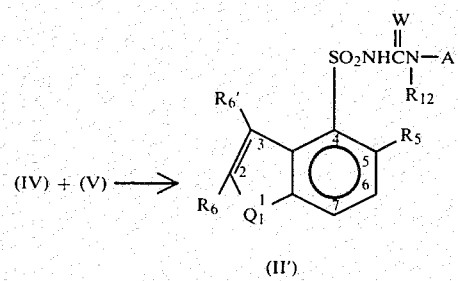

(II')

The reactions of Equations 1 and 2 are best carried out in inert aprotic organic solvents such as methylene chloride, tetrahydrofuran or acetonitrile at ambient pressure and temperature. The mode of addition is not critical; however, it is often convenient to add the sulfonylisocyanate or isothiocyanate to a stirred suspension of amine V. The reactions are generally exothermic. In some cases the desired product is insoluble in the warm reaction medium and crystallizes from it in pure form. Products soluble in the reaction medium are isolated by evaporation of the solvent, trituration of the solid residue with solvents such as 1-chlorobutane, ethyl ether, ethyl acetate or pentane, and filtration.

Alternatively, as shown in Equations 3 and 4, compounds I, I', II and II', where $R_5$ is other than $CO_2R_7$ and W=O, can be prepared by reacting arylsulfonamides of Formulae (VI) and (VII), respectively, with an appropriate methyl carbamate of Formula (VIII), in the presence of an equimolar amount of trimethylaluminum.

Equation 3

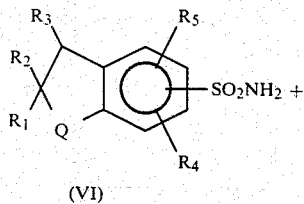

(VI)

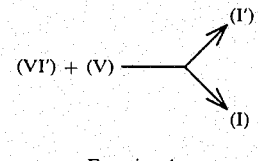

(VIII)

Equation 4

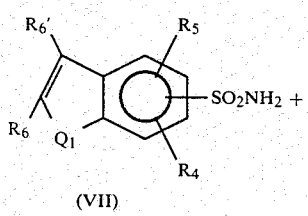

(VII)

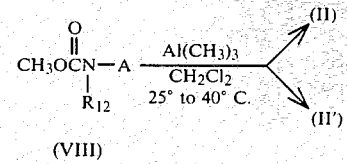

(VIII)

wherein for Equations 3 and 4 $R_1$ to $R_6'$, $R_{12}$, A, $Q_1$ and Q are as previously defined, except $R_5$ is other than $CO_2R_7$.

The reactions of Equations 3 and 4 are best carried out in methylene chloride at about 25° to 40° C. for 10 to 96 hours under a nitrogen atmosphere. The product is isolated by addition of an aqueous acetic acid or hydrochloric acid solution followed by extraction of the product into methylene chloride, or by direct filtration of a product of low solubility. The product is purified by trituration with solvents such as 1-chlorobutane, ethyl acetate or ethyl ether or subjected to chromatography procedures. Trimethylaluminum is commercially available. The reactions of Equations 3 and 4 are particularly useful for preparing I, I', II and II' (W=O) where sulfonylisocyanates are difficult to prepare from the corresponding sulfonamides VI and VII.

In addition, as shown in Equations 3a and 4a below, compounds of Formulae (I), (I'), (II) and (II') (where W=O) can be prepared by reacting sulfonylcarbamates VI' and VII', respectively, with an appropriate amine V.

Equation 3a

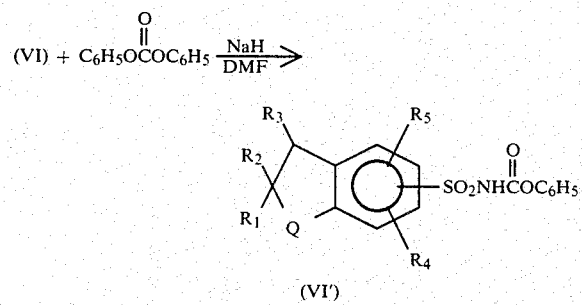

(VI')

Equation 4a

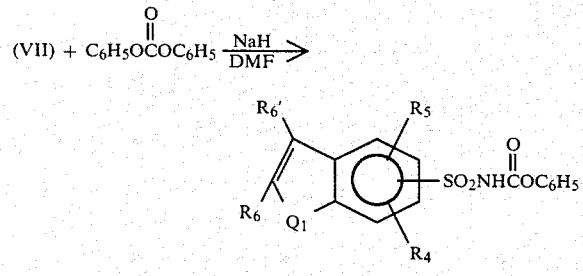

(VII')

-continued

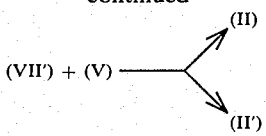

-continued

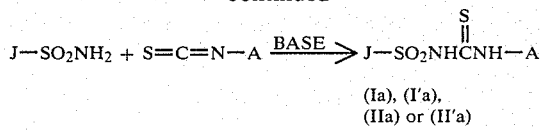

(Ia), (I'a),
(IIa) or (II'a)

where J is

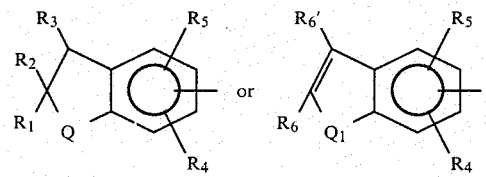

wherein for Equations 3a and 4a $R_1$ to $R_6'$, $R_{12}$, A, $Q_1$ and Q are as previously defined, except $R_5$ is other than $CO_2R_7$.

The reactions are run at 50°–100° C. in a solvent such as dioxane for 0.5 to 24 hours as taught in EPO Publication No. 44807. The required carbamates VI' and VII' are prepared by reacting corresponding sulfonamides VI and VII, respectively, with diphenylcarbonate in the presence of a strong base.

The intermediate sulfonylisocyanates of Formulae (III) and (IV) (W=0) in Equations 1 and 2 can be prepared from sulfonamides by methods taught in U.S. Pat. No. 4,238,621. The method requires reacting sulfonamides with phosgene, in the presence of n-butylisocyanate and a tertiary amine catalyst, at reflux in a solvent such as xylene or chlorobenzene. A preferred catalyst is 1,4-diazabicyclo[2.2.2]octane (DABCO).

Alternatively, the sulfonylisocyanates can be prepared from sulfonamides by a two-step procedure. This involves (a) reacting the sulfonamides with n-butylisocyanate and a base such as $K_2CO_3$ at reflux in an inert solvent such as 2-butanone to form a n-butyl sulfonylurea; and (b) reacting this compound with phosgene and DABCO catalyst at reflux in xylene or chlorobenzene solvent. The latter method is similar to a procedure taught by Ulrich and Sayigh, New Methods of Preparative Organic Chemistry, Vol. VI, p. 223–241, Academic Press, New York and London, W. Foerst Ed.

The intermediate sulfonylisothiocyanates of Formulae (III) and (IV) (W=S) in Equations 1 and 2 can be prepared from sulfonamides by methods taught in H. Hartke, Arch. Pharm., 229, 174 (1966). The method requires (a) reacting an appropriate sulfonamide with an equivalent amount of carbon disulfide and two equivalents of potassium hydroxide in dimethylformamide at room temperature for 1–8 hours to form the dipotassium salt of the sulfonyliminodithiocarbonate; (b) diluting the suspension with ethyl acetate, ethyl ether or similar aprotic solvent to cause the salt to precipitate, (c) reacting the isolated, dried salt with phosgene in an inert solvent such as xylenes, benzene, carbon tetrachloride or methylene chloride at about room temperature for 1–3 hours; and (d) isolating the sulfonylisothiocyanate, which is usually soluble in the solvent, by filtering off the insoluble potassium chloride and concentrating the filtrate. In place of phosgene, a chloroformic ester (e.g., methyl chloroformate), phosphorus pentachloride, sulfuryl chloride or thionyl chloride may be used.

The compounds of Formula (I), (I'), (II) and (II'), where W is S and $R_{12}$ is H, may also be prepared by reacting an appropriate sulfonamide with a heterocyclic isothiocyanate of Formula (V'), as shown in Equation 4b.

Equation 4b and wherein $R_1$ to $R_6'$, Q, $Q_1$ and A are as originally defined.

The reaction is carried out at 25° to 80° C. in an inert, aprotic solvent such as acetone or acetonitrile in the presence of a base such as potassium carbonate for 0.5 to 24 hours. The required heterocyclic isothiocyanates V' are prepared from the corresponding amines V as taught in EPO Publication 35893.

The intermediate sulfonamides of Formulae (VI) and (VII) in Equations 3 and 4 can be prepared by reacting corresponding sulfonyl chlorides with ammonium hydroxide or ammonia in an inert solvent such as tetrahydrofuran or methylene chloride at ambient temperature, according to procedures widely reported in the literature for preparing other sulfonamides, e.g., Crossley et al., J. Am. Chem. Soc., 60, 2223 (1938) and Pailer, Monatsh, 92, 677 (1961).

Arylsulfonyl chlorides are ordinarily prepared from aromatic amines by diazotization with sodium nitrite in HCl, followed by reaction of the diazonium salt with sulfur dioxide and cupric chloride in acetic acid, according to the teachings of Yale and Sowinski, J. Org. Chem., 25, 1824 (1960). As shown in Equations 5 and 6, however, sulfonyl chlorides (XI) and (XII) are preferably prepared by a modification of this procedure.

Equation 5

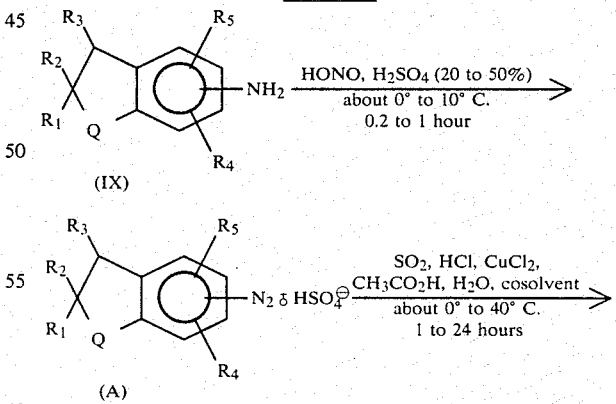

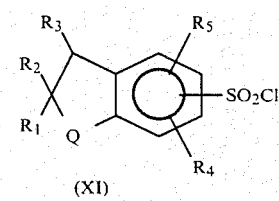

-continued
Equation 6

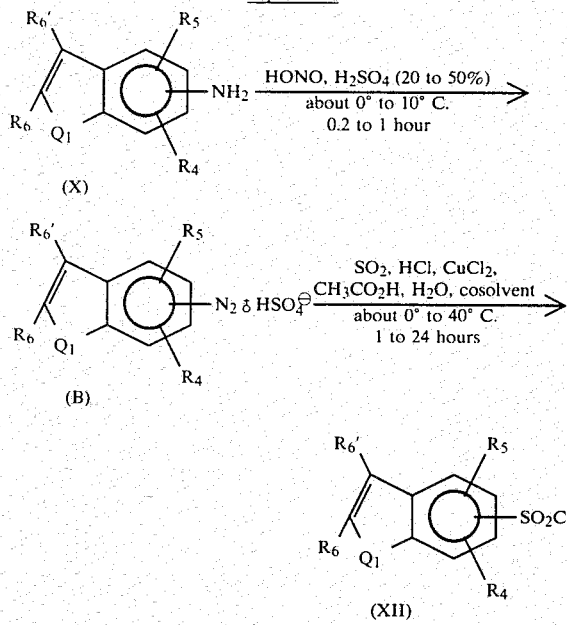

The diazotization reactions of Equations 5 and 6 are best carried out with sodium nitrite in dilute sulfuric acid (about 20 to 50%), at about 0° to 10° C. for about 0.2 to 1 hour. This method for preparing diazonium salts from benzofuranamines and benzo[b]thiopheneamines is widely reported in the literature, e.g., Bordwell and Stange, J. Am. Chem. Soc., 27, 5939 (1955); Arnold and McCool, ibid 64, 1315 (1942); Neth. Appl. 6,602,601; and U.S. Pat. No. 4,032,649.

The sulfonyl chlorides in Equations 5 and 6 are prepared by reacting the diazonium salts with stirred suspensions containing sulfur dioxide, hydrochloric acid and cupric chloride. The reactions are preferably carried out in a cosolvent mixture consisting of acetic acid-water (about 1:1) and an immiscible, inert solvent such as 1-chlorobutane or methylene chloride, preferably 1-chlorobutane. The reactions are run at about 0° to 40° C., preferably at 25° to 40° C. for 1 to about 24 hours. The mode of addition is not critical; it is however, often convenient to add the diazonium salt to the suspension containing the sulfur dioxide. The sulfonyl chlorides are isolated by addition of water, separation of the organic phase, washing the organic phase with saturated aqueous $NaHCO_3$ and water and evaporation of the solvent under reduced pressure at less than about 50° C.

An alternate method for preparing some 2,3-dihydro-7-benzo[b]thiophenesulfonamides of Formula (VI) (Q=S) in Equation 3 above is shown in Equation 7 below.

Equation 7

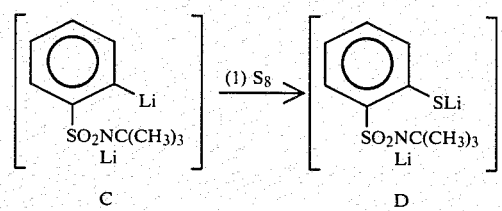

-continued
Equation 7

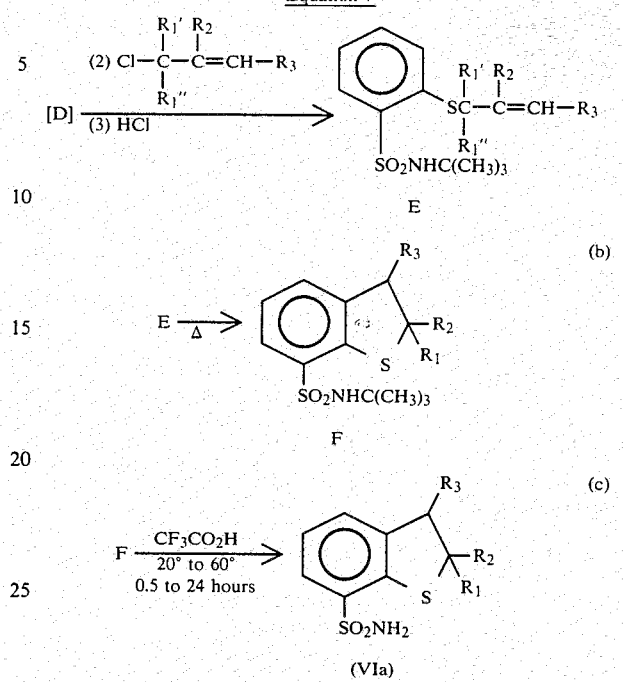

wherein
$R_1$ is $C_1$–$C_4$ alkyl;
$R_2$ and $R_3$ are as previously defined;
$R_1'$ is H or $CH_3$; and
$R_1''$ is H or $C_1$–$C_3$ alkyl; when
$R_1''$ is $C_3H_7$, $R_1'$ is H.

The reactions of Equation 7(a) are run in-situ as follows: The dilithium salt C is prepared by reacting t-butylbenzenesulfonamide with two equivalents of n-butyl lithium at 0° to 30° C. in an inert solvent such as tetrahydrofuran for one to five hours, according to the teachings of Lombardino, J. Org. Chem., 36, 1843 (1971). The N-t-butyl-2-propenylthiobenzenesulfonamide of Formula E is then prepared by (1) contacting this mixture containing C with elemental sulfur at 0° and stirring at ambient temperature for one to five hours to form lithium thiolate D; (2) contacting this mixture with an appropriate allyl halide at 0° and stirring at ambient temperature for about 24 hours to form E; and (3) isolating E by addition of dilute hydrochloric acid to this mixture to decompose any salts present, followed by separation and concentration of the organic phase. The reaction of organolithium reagents with sulfur to form lithium thiolates which may be alkylated in-situ is known in the art, e.g., Gschwend et al., "Organic Reactions", 26, Chapter 1, p. 83 (1979) and references cited therein.

In Reaction 7(b) above, the N-t-butyl-2,3-dihydro-7-benzo[b]thiophenesulfonamides of Formula F are prepared by heating E either neat or in an inert solvent such as quinoline or N,N-dimethylaniline at 150°–300° C. for 0.25 to 2 hours to cause cyclization. Compound F is isolated by addition of an inert solvent such as ether or methylene chloride, washing well with dilute hydrochloric acid and water, followed by separation and concentration of the organic phase. Compound F can be purified by column chromatography and recrystallization procedures.

And in Reaction 7(c), the t-butylsulfonamides F are dealkylated to form sulfonamides VIa by reacting F with excess trifluoroacetic acid at 20° to 40° C. for about 10 to 30 hours. Compounds VIa are isolated and purified by concentration of the reaction mixture, addition of methylene chloride to the residue, washing the suspension with dilute aqueous NaHCO₃ and concentration of the organic phase. Alternatively, t-butylsulfonamides F may be converted to sulfonamides VIa by heating in methanol containing at least an equimolar quantity of hydrochloric acid, followed by concentration of the reaction mixture and precipitation of the product with ether.

The amines of Formulae (IX) and (X) in Equations 5 and 6 above are important starting materials for the preparation of the compounds of this invention, which can be prepared by the following general methods.

Several of the starting 4- and 7-amino-2,3-dihydrobenzofurans of Formula (IX) in Equation 5 are known. For instance, 4-amino-2,3-dihydro-2,2-dimethylbenzofuran may be prepared by the procedure of Cruickshank et al., J. Med. Chem., 13, 1110 (1970); 7-amino-2,3-dihydro-2,2-dimethylbenzofuran by the procedure of Netherlands Pat. No. 6,602,601; 7-amino-2,3-dihydro-2-methylbenzofuran by the procedure of Belgium Pat. No. 744,858; 4-amino-2,3-dihydrobenzofuran by the procedure of U.S. Pat. No. 3,963,717; and 7-amino-2,3-dihydrobenzofuran by the procedure of U.S. Pat. No. 3,963,717.

The 7-amino-2,3-dihydrobenzofurans of Formula (IX) in Equation 5, where $R_5$ is H, $CH_3$, $OCH_3$, Cl, F, $SCH_3$, $OCF_2H$, Br or $CF_3$, can be prepared by a procedure analogous to that taught in Netherlands Pat. No. 6,602,601. This procedure is illustrated in Equation 8 below.

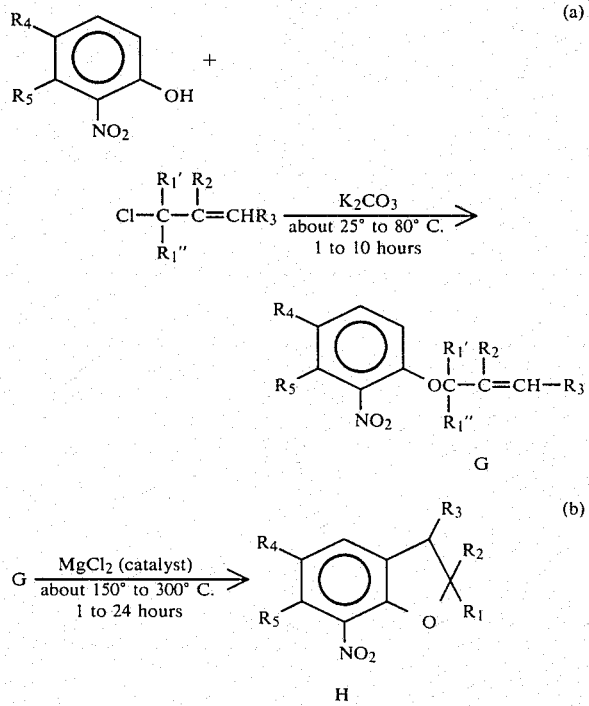

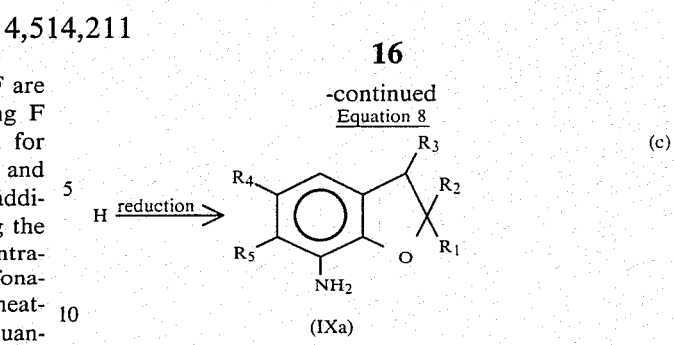

wherein
$R_1$ is $C_1$–$C_4$ alkyl;
$R_2$, $R_3$ and $R_4$ are as originally defined;
$R_5$ is H, $CH_3$, $OCH_3$, Cl, Br, F, $CF_3$, $SCH_3$ or $OCF_2H$;
$R_1'$ is H or $CH_3$; and
$R_1''$ is H or $C_1$–$C_3$ alkyl; when $R_1''$ is $C_3H_7$, $R_1'$ is H.

As shown in Equation 8, the preparation requires three steps: (1) reacting a 3- or 4-(substituted)-2-nitrophenol with an appropriately substituted allyl halide to form intermediate G; (2) heating this compound at elevated temperatures 150° to 300° C. with a catalyst to cause cyclization to form H; and (3) reducing this compound to form IXa. The first reaction is run in a warm protic solvent such as ethanol in the presence of a weak base such as $K_2CO_3$. The cyclization step is normally run neat at elevated temperatures, in the range of 150° to 300° C. for 1 to 24 hours. A Friedel-Crafts catalyst, such as magnesium chloride, is ordinarily used to promote the cyclization reaction and increase product yields. Intermediate H may be purified by recrystallization or chromatography procedures. The reduction step can be carried out by any of several known methods for reducing nitro groups to amino groups. For example, intermediate H can be catalytically reduced with 5% palladium-on-charcoal in ethanol solvent at about 25° to 45° C. and at 1 to 3 atmospheres of pressure. Alternatively, H can be heated with stannous chloride in concentrated hydrochloric acid at about 25° to 80° C. for 0.5 to 3 hours to form IXa.

Alternatively, the Claisen rearrangement-cyclization reaction in Equation 8b above can be run stepwise as follows: (a) phenyl allyl ether G can be rearranged at about 150° to 200° C. for 0.5 to 10 hours either neat or in the presence of a suitable high boiling solvent such as diethylaniline or o-dichlorobenzene to yield the corresponding 4- or 5-(substituted)-6-nitro-2-allylphenol, according to the teachings in S. J. Rhoads and N. R. Raulins, Organic Reactions, Vol. 22, p. 1–253, John Wiley and Sons, New York and London, W. G. Dauben, Ed.; and (b) this compound may be cyclized to dihydrobenzofuran H by methods widely reported in the literature for analogous type reactions. For instance, heating the rearranged product with pyrimidine.HCl ($R_4$ and $R_5 \neq OCH_3$), or with acidic reagents such as hydrogen bromide in acetic acid, or with a Friedel-Crafts catalyst such as magnesium chloride can yield H according to teachings of Claisen and Tietze, Ann, 449, 81 (1926), and 442, 235 (1925); Arnold and Mc Cool, J. Am. Chem. Soc., 64, 1315 (1942); J. Entel et al., ibid., 73, 2365 (1951); P. Cruickshank et al., J. Med. Chem., 13, 1110 (1970); and Q. Bartz et al., J. Am. Chem. Soc., 57, 371 (1935).

The 7-amino-2,3-dihydrobenzofurans of Formula (IX) in Equation 5, where $R_5$ is $OSO_2R_9$, $SO_2R_8$, $CO_2R_7$, $OCH_3$, $SO_2NR_{10}R_{11}$, $SCH_3$, $OCF_2H$ or $SO_2N$-

($OCH_3$)$CH_3$, can be prepared as shown in Equation 9 below.

Equation 9

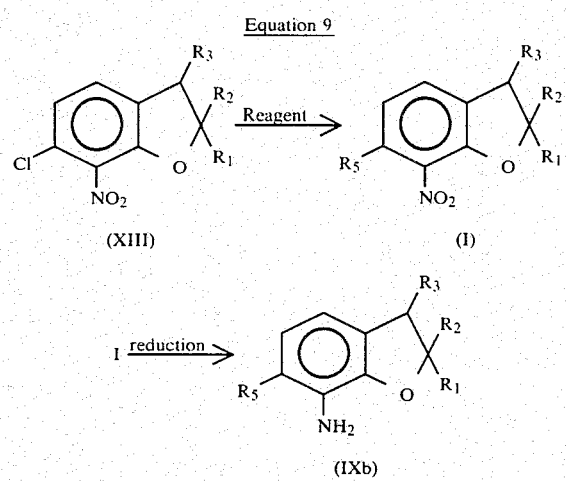

wherein $R_1$, $R_2$ and $R_3$ are as originally defined; and
$R_5$ is $OSO_2R_9$, $SO_2R_8$, $CO_2R_7$, $OCH_3$, $SO_2NR_{10}R_{11}$, $SCH_3$, $OCF_2H$ or $SO_2N(OCH_3)CH_3$.

According to Equation 9, a 6-chloro-7-nitro-2,3-dihydrobenzofuran of Formula (XIII) is reacted with reagents as discussed below to form intermediate I containing the desired $R_5$ group. The nitro compound I is then reduced to form IXb. These reactions can be run by obvious methods by one skilled in the art.

Intermediate I, where $R_5$ is $OSO_2CH_3$ for example, is prepared in two steps: (1) heating XIII with one equivalent of a strong base such as sodium or potassium hydroxide in dimethylformamide at 50° to 80° C., for 1 to 8 hours, to form I, where $R_5$ is OH; and (2) reacting the resulting phenol with methanesulfonyl chloride, in the presence of a base such as triethylamine, in an inert solvent such as tetrahydrofuran, at 25° to 70° C., for 1 to 24 hours, to form I where $R_5$ is $OSO_2CH_3$. Intermediate I, where $R_5$ is $SO_2CH_3$ for example, is also prepared in two steps: (1) heating XIII with one equivalent of sodium methylmercaptide in dimethylformamide at 25° to 80°, for 1 to 8 hours, to form I, where $R_5$ is $SCH_3$; and (2) oxidizing the resulting compound with 30% hydrogen peroxide in acetic acid solvent, at 0° to 60°, for 1 to 8 hours, to form I, where $R_5$ is $SO_2CH_3$. Intermediate I, where $R_5$ is $CO_2CH_3$ for example, is prepared in three steps: (1) reacting XIII with one equivalent of potassium cyanide in dimethylformamide at 50° to 80° C., for 1 to 24 hours, to form I where $R_5$ is CN; (2) hydrolyzing the cyano group to a carboxylic acid by any of several methods known in the art; for example, I where $R_5$ is CN can be refluxed with concentrated hydrochloric acid in acetic acid solvent to form I where $R_5$ is $CO_2H$; and (3) converting the carboxylic acid to a carbonyl chloride which is then reacted with methanol to form I where $R_5$ is $CO_2CH_3$. The latter reactions can be run by known methods by one skilled in the art. Intermediate I, where $R_5$ is $OCH_3$ or $OCF_2H$, are prepared by alkylating a phenol of Formula I, where $R_5$ is OH, with reagents such as dimethylsulfate or methyl iodide or chlorodifluoromethane. The reactions take place in the presence of a base such as potassium carbonate in an inert solvent such as dioxane or dimethylformamide at about 0° to 80° C. by methods known in the art. Intermediate I, where $R_5$ is $SO_2NR_{10}R_{11}$ or $SO_2N(OCH_3)CH_3$, are prepared in two steps from I, where $R_5$ is $SCH_3$: (1) Intermediate I, where $R_5$ is $SCH_3$, is oxidatively chlorinated to the corresponding sulfonyl chloride by addition of chlorine to the sulfide in the presence of water at about 15° to 80° C., in an aliphatic carboxylic acid solvent such as acetic acid, for 1 to 24 hours to form I, where $R_5$ is $SO_2Cl$; and (2) reacting the sulfonyl chloride with an appropriate secondary amine by general methods to form I, where $R_5$ is $SO_2NR_{10}R_{11}$ or $SO_2N(OCH_3)CH_3$.

In the final step of Equation 9, I can be reduced to IXb by methods previously described in Equation 8. Many starting 6-chloro-7-nitro-2,3-dihydrobenzofurans of Formula (XIII) are also prepared by methods described above in Equation 8.

Similarly, the 4-amino-2,3-dihydrobenzofurans of Formula (IX) in Equation 5, where $R_5$ is $SO_2R_8$, $OSO_2R_9$, $CO_2R_7$, $OCH_3$, $SO_2NR_{10}R_{11}$, $SCH_3$, $OCF_2H$ or $SO_2N(OCH_3)CH_3$, can be prepared by procedures described in Equation 9. Thus, by starting with an appropriate 5-chloro-4-nitro-2,3-dihydrobenzofuran, and proceeding with the reactions described above in Equation 9, one skilled in the art can prepare the subject 4-amino-2,3-dihydrobenzofurans of Formula (IX). The preparation of many 5-chloro-4-nitro-2,3-dihydrobenzofurans is described below in Equation 11. 5-Chloro-4-nitro-2,3-dihydrobenzofuran may be prepared by hydrolysis of the diazonium cobaltinitrite salt of 5-chloro-4-amino-2,3-dihydrobenzofuran by obvious methods by one skilled in the art. Similarly, 6-chloro-7-nitro-2,3-dihydrobenzofuran of Formula (XIII) in Equation 9 above, may be prepared from 6-chloro-7-amino-2,3-dihydrobenzofuran. For general details, refer to an analogous type reaction described in D. E. Bosewell, et al., J. Heterocycl. Chem., 5, 69 (1968).

The 7-amino-2,3-dihydrobenzofurans of Formula (IX) in Equation 5, where $R_5$ is $NO_2$, $SO_2NR_{10}R_{11}$ or $SO_2N(OCH_3)CH_3$ can be prepared as shown in Equation 10.

Equation 10

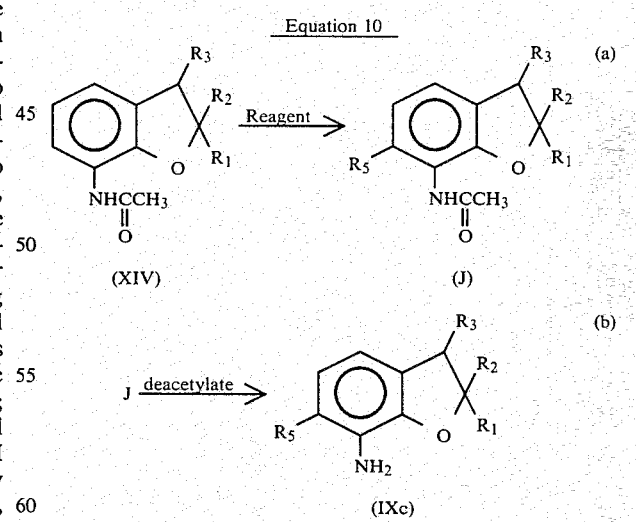

wherein $R_1$, $R_2$ and $R_3$ are as originally defined; and
$R_5$ is $NO_2$, $SO_2NR_{10}R_{11}$ or $SO_2N(OCH_3)CH_3$.

According to Equation 10, a 7-acetamido-2,3-dihydrobenzofuran XIV is reacted with reagents as described below to form intermediate J. Then J is deacetylated to form IXc.

Intermediate J, where $R_5$ is $NO_2$, is prepared in two steps: (1) nitration of XIV with nitric acid in acetic acid solvent, at about 10° to 25° C., for 0.5 to 5 hours, to form a mixture containing in part J where $R_5$ is $NO_2$; and (2) separation of J from the mixture by recrystallization or chromatographic procedures.

Intermediate J, where $R_5$ is $SO_2NR_{10}R_{11}$ or $SO_2N(OCH_3)CH_3$, is prepared in three steps: (1) chlorosulfonation of intermediate XIV with chlorosulfonic acid to form a mixture of products containing in part J, where $R_5$ is $SO_2Cl$; (2) contacting the resulting mixture with an appropriate secondary amine in an inert solvent such as tetrahydrofuran, at about 10° to 60° C., for 0.5 to 10 hours to form in part J where $R_5$ is $SO_2NR_{10}R_{11}$ or $SO_2N(OCH_3)CH_3$; and (3) separation of the desired intermediate J from the crude product by recrystallization or chromatographic procedures. The chlorosulfonation step can be run by reacting XIV with excess chlorosulfonic acid, i.e., about a three equivalent excess, at 25° to 70° C., in an inert solvent such as chloroform, for 0.5 to 8 hours.

Deacetylation of J to form IXc, can be carried out by saponification or acid hydrolysis procedures. Thus, refluxing J in 90% ethanol with one equivalent of sodium hydroxide, for 0.25 to 3 hours, can provide IXc. Alternatively, heating J, at 50° to 80° C., with hydrochloric acid in acetic acid for 0.5 to 3 hours can also provide IXc. The starting compound XIV can be prepared by known methods, i.e., by heating, at 50° to 100° C., an appropriate 7-amino-2,3-dihydrobenzofuran in acetic anhydride, with a catalytic amount of sulfuric acid, for 1 to 10 hours.

Similarly, the 4-amido-2,3-dihydrobenzufurans of Formula (IX) in Equation 5, where $R_5$ is $NO_2$, $SO_2NR_{10}R_{11}$ or $SO_2N(OCH_3)CH_3$, can be prepared by procedures described in Equation 10 above. Thus, by starting with an appropriate 4-acetamido-2,3-dihydrobenzofuran, and proceeding with the appropriate reactions described above in Equation 10, the following compounds can be prepared: 4-amino-2,3-dihydro-5-nitrobenzofurans and 4-amino-5-(N,N-dialkylsulfonamido or N-methyl-N-methoxysulfonamido)-2,3-dihydrobenzofurans of Formula (IX), where $R_1$ to $R_3$ are as defined above. The starting 4-acetamido-2,3-dihydrobenzofurans can be prepared from 4-amino-2,3-dihydrobenzofurans by methods also described in Equation 10.

The 4-amino-2,3-dihydrobenzofurans of Formula (IX) in Equation 5, where $R_5$ is H, $OCH_3$, Cl, Br, $CO_2R_7$, $OSO_2R_9$, $OCF_2H$ or F, can be prepared as illustrated below in Equation 11.

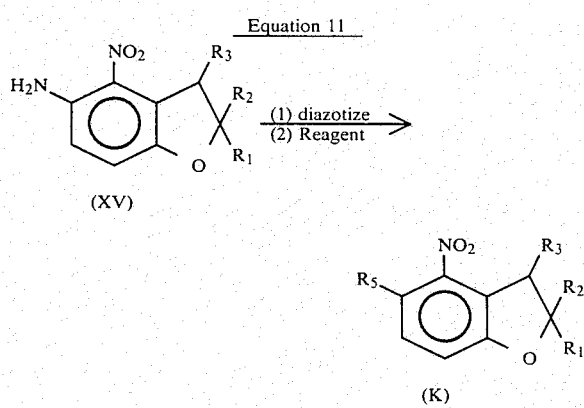

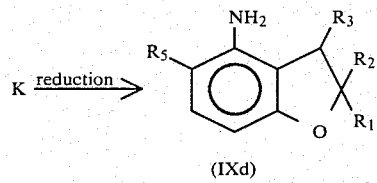

wherein
$R_1$ is $C_1-C_4$ alkyl;
$R_2$ and $R_3$ are as originally defined; and
$R_5$ is H, $OCH_3$, Cl, Br, $CO_2R_7$, $OSO_2R_9$, $OCF_2H$ or F.

According to Equation 11, a 5-amino-2,3-dihydro-4-nitrobenzofuran of Formula (XV) is diazotized, then reacted with appropriate reagents to form intermediate K. Reduction of K can then provide IXd. The diazonium salt can be prepared with sodium nitrite in dilute sulfuric (20 to 50%) at about 0° to 10° C. by methods known in the art, e.g., Arnold and McCool, J. Am. Chem. Soc., 64, 1315 (1942). Intermediate K, where $R_5$ is as defined above, can be prepared from the diazonium salt by methods also known in the art.

Thus, intermediate K, where $R_5$ is Cl, Br or F, can be prepared by heating the diazonium salt with cuprous chloride and hydrochloric acid or with cuprous bromide and hydrobromic acid, according to the Sandmeyer reaction, e.g., Powers, J. Med. Chem., 19, 57 (1976) and Morrison and Boyd, Organic Chemistry, 3rd Ed.; pgs. 767–770 (1974). Intermediates K, were $R_5$ is $OCH_3$ or $OCF_2H$, can be prepared in two steps: (1) intermediate K, where $R_5$ is OH, is prepared by refluxing the diazonium salt with copper sulfate solution (50%), a procedure well-known in the art for preparing phenols from diazonium salts, e.g., Arnold and McCool, J. Am. Chem. Soc., 64, 1315 (1942); and (2) the phenol is then contacted with dimethylsulfate or chlorodifluoromethane as described above in Equation 9 to form K, where $R_5$ is $OCH_3$ or $OCF_2H$.

Intermediate K, where $R_5$ is $OSO_2R_9$, can be prepared by reacting the phenol described above with an appropriate alkylsulfonyl chloride and a base such as triethylamine in an inert solvent such as tetrahydrofuran at a temperature of about 0° to 60° C.

Intermediate K, where $R_5$ is $CO_2R_7$, is prepared in the following manner: (1) intermediate K, where $R_5$ is CN, is prepared by the Sandmeyer reaction. Thus, the diazonium salt is heated with cuprous cyanide according to methods well known in the art, e.g, Hansch and Schmidhalter, J. Org. Chem., 20, 1056 (1955); (2) intermediate K, where $R_5$ is $CO_2H$, is then prepared by refluxing the cyano compound, with hydrochloric acid in acetic acid solvent for 1 to 10 hours; and (3) intermediate K, where $R_5$ is $CO_2R_7$, is prepared by converting the carboxylic acid to a carbonyl chloride which is then reacted with appropriate alcohols to form K., where $R_5$ is $CO_2R_7$. Reaction (3), takes place according to methods known in the art.

Intermediate K, where $R_5$ is H, is prepared by reacting the diazonium salt with 50% hypophosphorous acid at 0° to 20° C. for 1 to 24 hours, according to a procedure of Bordwell and Stange, J. Am. Chem. Soc., 77, 5939 (1955). The final step in Equation 11, the reduction of K to form IXd, is carried out by the methods described previously in Equation 9.

The starting compounds of Formula (XV) in Equation 11 can be prepared according to the disclosure of Arnold and McCool, J. Am. Chem. Soc., 64, 1315 (1942), the disclosure of which is herein incorporated by reference. Arnold and McCool teach the preparation of 5-amino-2,3-dihydro-2-methyl-4-nitrobenzofuran by a multistep procedure starting with the reaction of 4-hydroxyacetophenone with allylbromide. By reacting 4-hydroxyacetophenone with other appropriately substituted allylbromides, or allyl chlorides, and using the multistep reactions and conditions taught by Arnold and McCool, one skilled in the art can prepare the compounds of Formula (XV) in Equation 11.

The 4-amino-2,3-dihydrobenzofurans of Formula (IX) in Equation 5, where $R_5$ is $CH_3$, H, Cl, Br, F or $CF_3$, can be prepared by a procedure analogous to that taught in Cruickshank, J. Med. Chem., 13, 1110 (1970). This procedure is illustrated in Equation 12 below.

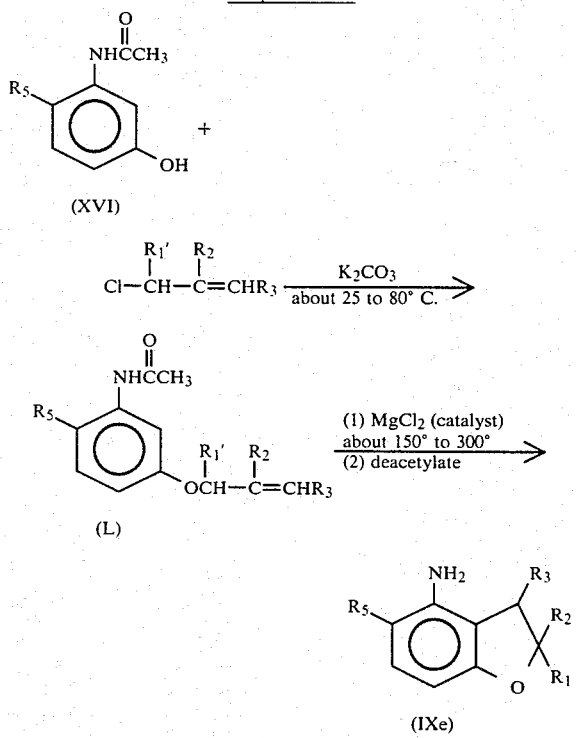

wherein
$R_1'$ is H or $C_1$–$C_3$ alkyl;
$R_1$ is $C_1$–$C_4$ alkyl;
$R_2$ and $R_3$ are as originally defined; and
$R_5$ is H, $CH_3$, Cl, Br, F or $CF_3$.

According to Equation 12, the preparation requires three steps: (1) reacting a 2-(substituted)-5-hydroxybenzacetamide of Formula (XVI) with an appropriately substituted allyl chloride and potassium carbonate at about 25° to 80° C. in an inert solvent such as acetone to form intermediate L; (2) heating this compound at elevated temperatures, about 150° to 300° C. with a suitable Friedel-Crafts catalyst such as magnesium chloride to cause cyclization to form a 5-(substituted)-4-acetamido-2,3-dihydrobenzofuran; and (3) deacetylating this compound in the usual manner to form IXe. These reactions can be run using general methods described previously in Equations 8 and 10, starting with an appropriate 2-(substituted)-5-hydroxybenzacetamide of Formula (XVI).

The 4- and 7-aminobenzofurans of Formula (X) in Equation 6, where $R_5$ is H and $R_6$ and $R_6'$ are H or $CH_3$, can be prepared by known general methods. Such methods are exemplified by Pene et al., Bull. Soc. Chim. France, 586 (1966); Rodighiero et al., Gazz. Chim. Ital., 91, 90 (1961); Royer et al., Bull. Soc. Chim. France, 1026 (1970); Kawase, Chem. Ind. (London), 687 (1970); Belgium 744, 859; Kawase et al., Bull. Chem. Soc. Japan, 44, 749 (1971); Fr. Demande 2,338,041; U.S. Pat. Nos. 3,577,441; and 3,452,033.

The 7-aminobenzofurans of Formula (X) in Equation 6, where $R_5$ is H, $OCH_3$, Cl, Br, F, $CF_3$, $SCH_3$, $OCF_2H$, $SO_2NR_{10}R_{11}$, $SO_2N(OCH_3)CH_3$, $CO_2R_7$, $SO_2R_8$ or $OSO_2R_9$ can be prepared as shown in Equation 13 below.

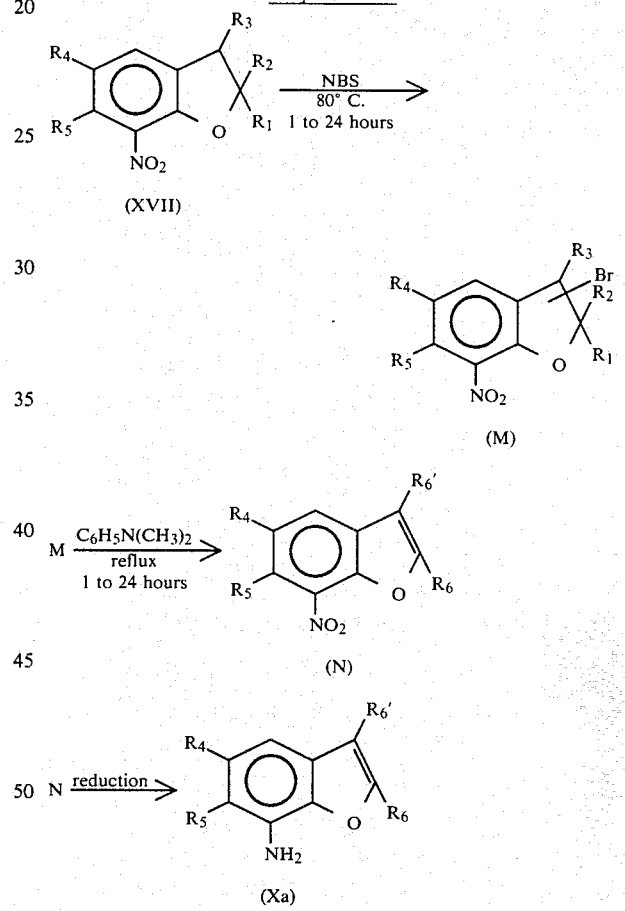

wherein
$R_1$, $R_2$ and $R_3$ are as originally defined, except at least one of $R_1$ or $R_2$ must be H;
$R_4$ is H, Cl, Br, F, $CF_3$, $OCH_3$, $SCH_3$ or $OCF_2H$;
$R_5$ is H, $OCH_3$, Cl, Br, $CO_2R_7$, $SO_2R_8$, F, $CF_3$, $SCH_3$, $OCF_2H$, $OSO_2R_9$, $SO_2NR_{10}R_{11}$ or $SO_2N(OCH_3)CH_3$;
$R_6'$ is H or $CH_3$; and
$R_6$ is H or $C_1$–$C_4$ alkyl.

As shown in Equation 13, the 7-aminobenzofurans of Formula (Xa) can be prepared from corresponding 7-nitro-2,3-dihydrobenzofurans of Formula (XVII), where at least one of $R_1$ or $R_2$ is H. The procedure involves a dehydrogenation reaction followed by a reduction reaction. The dehydrogenation reaction may be carried out using a procedure of Geisman, J. Am. Chem. Soc., 72, 4326 (1950) and Hurd, J. Am. Chem. Soc., 80, 4711 (1958).

Thus, compound XVII is dehydrogenated by a two-step sequence: (1) 2,3-dihydrobenzofuran XVII is heated at 60° to 80° C. for 1 to 24 hours with N-bromosuccinimide (NBS) and benzoyl peroxide catalyst in an inert organic solvent such as benzene or carbon tetrachloride thereby brominating the non-aromatic portion of the molecule to form intermediate M; (2) this intermediate is heated with excess N,N-dimethylaniline, $[C_6H_5N(CH_3)_2]$, either neat or in an inert aprotic solvent such as toluene for 1 to 24 hours, to cause dehydrobromination to form 7-nitrobenzofuran N. Reduction of N to form 7-aminobenzofuran Xa can be carried out by any of several methods known in the art for reducing nitrobenzofurans. For instance, catalytic reduction of N with Raney Nickel catalyst in an inert solvent such as ethanol at about 25° to 70° C. and 1 to 3 atmospheres of hydrogen can provide Xa, according to a procedure of Belgium Pat. No. 744,858. Many of the starting compounds XVII are described above in Equations 8 and 9.

Similarly, the 4-aminobenzofurans of Formula (X) in Equation 6, where $R_5$ is H, $OCH_3$, Cl, Br, $CO_2R_7$, F, $CF_3$, $SCH_3$, $OCF_2H$, $SO_2NR_{10}R_{11}$, $SO_2N(OCH_3)CH_3$, $OSO_2R_9$ or $SO_2R_8$ and $R_6$ is H or $C_1$–$C_4$ alkyl and $R_6'$ is H or $CH_3$, can be prepared by procedures described in Equation 13. Thus, by starting with an appropriate 5-(substituted)-2,3-dihydro-4-nitrobenzofuran, and proceeding with the reactions described in Equation 13, one skilled in the art can prepare the subject 4-aminobenzofurans of Formula (X). The preparation of many of the starting 5-(substituted)-2,3-dihydro-4-nitrobenzofurans is described above, e.g. Equations 9 and 11.

The 7-aminobenzofurans of Formula (X) in Equation 6, where $R_5$ is H, $CH_3$, Cl, Br, $OCH_3$, $SO_2R_8$, F, $CF_3$ or $SCH_3$ can be prepared as shown in Equation 14 below.

wherein
$R_4$ is as originally defined;
$R_5$ is H, $CH_3$, Cl, Br, $OCH_3$, $SO_2R_8$, F, $CF_3$ or $SCH_3$;
$R_6$ is H or $C_1$–$C_4$ alkyl; and
$R_6'$ is $CH_3$.

According to Equation 14, the preparation requires three steps (1) reacting a 3- or 4-(substituted)-2-nitrophenol with an α-chloroketone such as chloropropanone for 1 to 8 hours at 30° to 80° C. in the presence of a base such as $K_2CO_3$ in an inert solvent such as acetone to form intermediate O; (2) cyclizing O to form a 7-nitrobenzofuran; and (3) reducing this compound to form a 7-aminobenzofuran of Formula (Xb). The cyclization step is carried out in polyphosphoric acid at a temperature of about 100° C. for 0.5 to 24 hours. Other methods are known in the art for preparing benzofurans from phenoxypropanones e.g., Pene, Bull. Soc. Chim. France, 586 (1966); Kawase, Chem. Ind. (London), 687 (1970); and Kawase et al., Bull. Chem. Soc. Japan, 44, 749 (1971). The reduction step can be carried out by the general methods described in Equation 13 above. Compound Xb, where $R_5$ is $SO_2R_8$, is prepared by (a) oxidizing the intermediate 7-nitrobenzofuran, where $R_5$ is $SR_8$, with 30% peracetic acid in acetic acid at 0° to 60° C. to form an intermediate 7-nitrobenzofuran, where $R_5$ is $SO_2R_8$, and (b) reducing this compound to form Xb where $R_5$ is $SO_2R_8$, by methods described in Equation 13 above.

The 7-aminobenzofurans of Formula (X) in Equation 6, where $R_5$ is $NO_2$, $SO_2NR_{10}R_{11}$ or $SO_2N(OCH_3)CH_3$ and $R_6$ is $C_1$–$C_4$ alkyl and $R_6'$ is $CH_3$, can be prepared as shown in Equation 15.

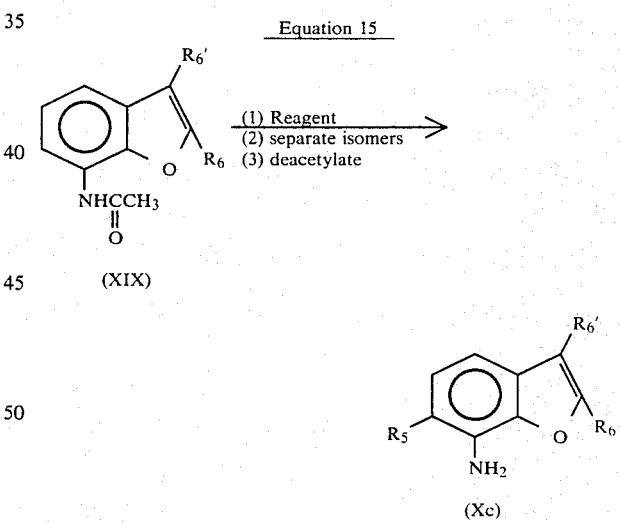

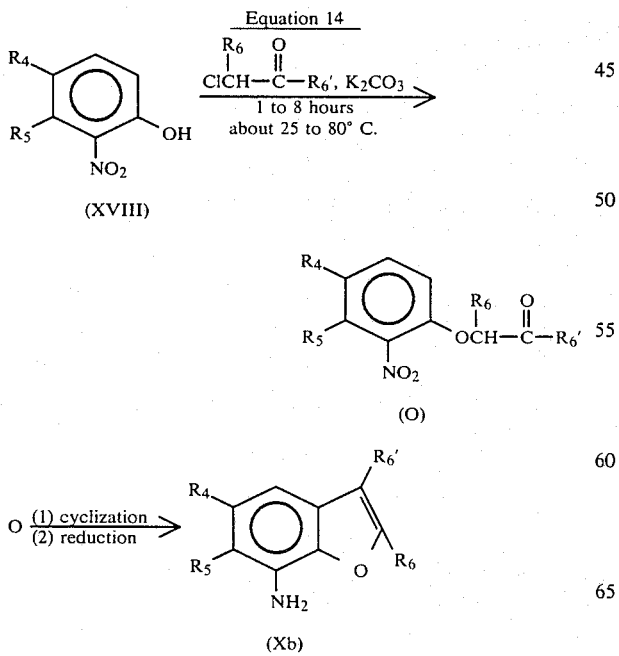

The reactions of Equation 15 can be carried out by procedures described previously in Equation 10. Thus, by nitration of chlorosulfonation of an appropriate 7-acetamidobenzofuran XIX according to procecures described in Equation 10, one skilled in the art can prepare the subject compounds Xc.

Similarly, the 4-aminobenzofurans of Formula (X) in Equation 6, where $R_5$ is $NO_2$, $SO_2NR_{10}R_{11}$ or $SO_2N$-$(OCH_3)CH_3$, $R_6$ is $C_1$–$C_4$ alkyl and $R_6'$ is $CH_3$, can be prepared by procedures described in Equation 15 above. Thus, by starting with an appropriate 4-acetamidobenzofuran, and carrying out the reactions described in Equation 15, one skilled in the art can prepare the subject 4-aminobenzofurans of Formula (X).

The 4-aminobenzofurans of Formula (X) in Equation 6, where $R_5$ is $CH_3$, Cl, Br, H, F or $CF_3$ can be prepared by a procedure analogous to that taught by Kawase et al., Bull. Chem. Soc. Jap., 749, 44 (1971). This procedure is illustrated in Equation 16 below.

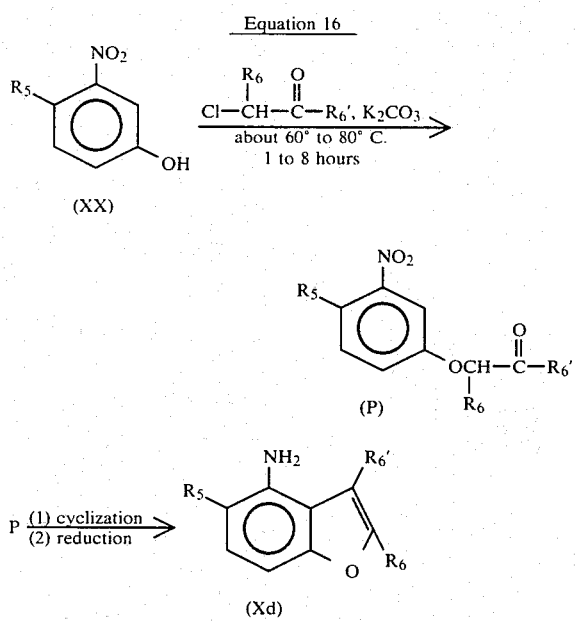

wherein $R_5$ is H, Cl, Br, $CH_3$, F or $CF_3$;

$R_6'$ is $CH_3$; and $R_6$ is H or $C_1$–$C_4$ alkyl.

According to Equation 16, the procedure requires three steps: (1) refluxing an appropriately substituted 4-substituted-3-nitrophenol with an α-chloroketone such as chloropropanone for 1 to 8 hours in the presence of a base, e.g., $K_2CO_3$, in a solvent, e.g., acetone, to form intermediate P; (2) cyclizing P to form a 4-nitrobenzofuran; and (3) reducing this compound to form a 4-aminobenzofuran of Formula (Xd). The cyclization step can be carried out in polyphosphoric acid at about 80° to 120° C. for 0.5 to 24 hours. The reduction step can be carried out by methods described in Equation 13 above.

The 4- and 7-amino-2,3-dihydrobenzo[b]thiophenes of Formula (IX) in Equation 5, where $R_4$ and $R_5$ are H can be prepared by the Bucherer reaction, as shown in Equation 17 below.

Equation 17

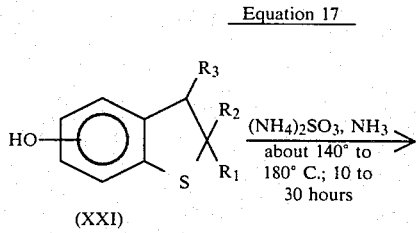

-continued
Equation 17

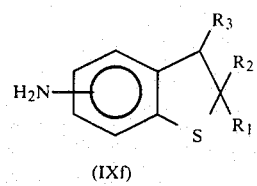

wherein $R_1$, $R_2$ and $R_3$ are as originally defined.

The reaction of Equation 17 can be carried out using general conditions reported in the literature for Bucherer reactions, e.g. Boswell et al., J. Heterocyclic Chem., 5, 69 (1968). An appropriate 4- or 7-hydroxy-2,3-dihydrobenzo[b]thiophene of Formula (XXI) is heated with concentrated ammonium hydroxide, sulfur dioxide and water in an autoclave at about 140° to 180° C. for 10 to 30 hours to provide IXf. The starting compounds XXI can be prepared by known methods. Several such methods are exemplified by Ger. Offen. 2,252,335; Kilsheimer, J. Agr. Food Chem., 17, 91 (1969); U.S. Pat. No. 4,032,649; and Ger. Offen. 2,534,857.

The 7-amino-2,3-dihydrobenzo[b]thiophenes of Formula (IX) in Equation 5, where $R_5$ is H, $CH_3$, $OCH_3$, Cl, Br, F or $CF_3$, can be prepared as shown in Equation 18 below.

Equation 18 wherein $R_1$ is $C_1$–$C_4$ alkyl;

$R_2$, $R_3$ and $R_4$ are as originally defined;

$R_5$ is H, $CH_3$, $OCH_3$, Cl, Br, F or $CF_3$;

$R_1'$ is H or $CH_3$; and $R_1''$ is H or $C_1$–$C_3$ alkyl; when $R_1''$ is $C_3H_7$, $R_1'$ is H.

According to Equation 18, the preparation requires two steps: In Step 18(a) a 3- or 4-(substituted)-2-aminothiophenol is reacted with an appropriately substituted allyl chloride, or allyl bromide, to form intermediate Q. The reaction is run in a warm protic solvent such as ethanol in the presence of an equimolar amount of a base such as sodium hydroxide for 1 to 10 hours. After dilution with water, the product Q is isolated by extraction with methylene chloride and concentration of the organic phase. Compound Q may be further purified by chromatography procedures.

And in step 18(b), Q is heated neat at 200° to 300° C. for about 0.5 to 5 hours to cause cyclization to form IXg. During the reaction, a thiochroman of Formula R may also form as a side-product. The desired product IXg can be separated from R and purified by high resolution distillation or chromatography procedures by one skilled in the art.

The 7-amino-2,3-dihydrobenzo[b]thiophenes of Formula (IX) in Equation 5, where $R_5$ is H, $CH_3$, $OCH_3$, Cl or Br, can be prepared by a procedure analogous to that taught in Singerman, U.S. Pat. No. 4,032,649, the disclosure of which is herein incorporated by reference. The relevant portion of the procedure is illustrated in Equation 19 below.

Equation 19

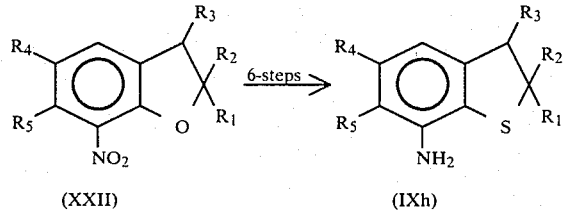

(XXII)    (IXh)

wherein $R_1$ is $C_1$–$C_4$ alkyl;

$R_2$ and $R_4$ are as originally defined;

$R_3$ is H; and $R_5$ is H, $CH_3$, $OCH_3$, Cl, Br or F.

U.S. Pat. No. 4,032,649 teaches the preparation of 7-amino-2,3-dihydro-2,2-dimethylbenzo[b]thiophene by a six-step reaction sequence starting with 7-nitro-2,3-dihydro-2,2-dimethylbenzofuran. By starting with an appropriate 5- or 6-(substituted)-7-nitro-2,3-dihydrobenzofuran of Formula (XXII), and following the six reactions described in U.S. Pat. No. 4,032,649, one skilled in the art can prepare the 5- or 6-(substituted)-7-amino-2,3-dihydrobenzo[b]thiophenes of Formula (IXh). The starting compound XXII can be prepared by methods described heretofore.

The six-step reaction sequence of Equation 19 involves (a) reacting XXII with potassium tert-butoxide in dimethylsulfoxide at 0° to 60° C. for 0.5 to 10 hours to form a 6-nitro-4 or 5-(substituted)-2-vinylphenol, (b) reacting this compound with sodium hydride and dimethylthiocarbamoyl chloride in tetrahydrofuran solvent at 0° to 60° C. for 1 to 10 hours to form a O-[6-nitro-4 or 5-(substituted)-2-vinyl]-N,N-dimethylthiocarbamate, (c) heating this compound under nitrogen at 150° to 200° C. for 0.5 hours to form a S-[6-nitro-4 or 5-(substituted)-2-vinyl]-N,N-dimethylthiocarbamate, (d) reducing this compound with iron powder in acetic acid at 25° to 90° C. for 0.5 to 3 hours to form a S-[6-amino-4 or 5-(substituted)-2-vinyl]-N,N-dimethylthiocarbamate, (e) reacting this compound with potassium hydroxide in water-methanol solvent at 40° to 80° C. for 1 to 24 hours to form a 6-amino-4 or 5-(substituted)-2-vinylthiophenol, and (f) cyclizing this compound by heating under nitrogen at 150° to 250° C. for 0.5 to 6 hours to form IXh in Equation 19.

The 7-amino-2,3-dihydrobenzo[b]thiophenes of Formula (IX) in Equation 5, where $R_5$ is $CO_2R_7$, $OSO_2R_9$, $SO_2R_8$, $OCH_3$, $SCH_3$ or $OCF_2H$, can be prepared as shown in Equation 20 below.

Equation 20

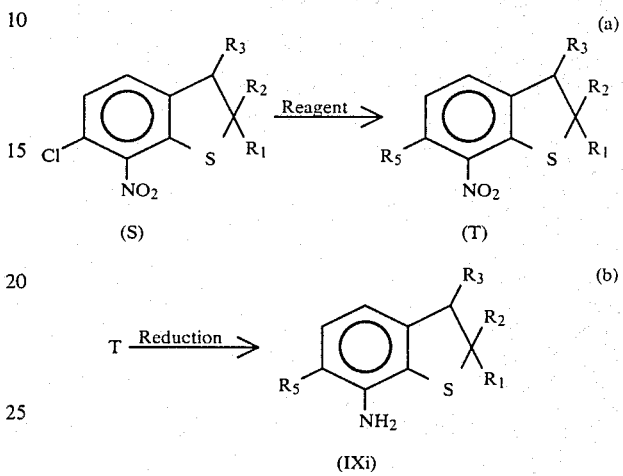

wherein $R_1$, $R_2$ and $R_3$ are as originally defined; and $R_5$ is $CO_2R_7$, $OSO_2R_9$, $SO_2R_8$, $OCH_3$, $SCH_3$ or $OCF_2H$.

According to Equation 20, a 6-chloro(or bromo-)-7-nitro-2,3-dihydrobenzo[b]thiophene S is reacted with reagents described below to form intermediate T containing the desired $R_5$ group. The nitro-compound T is then reduced to form IXi. These reactions can be run by obvious methods.

Thus, compound T, can be prepared by one skilled in the art using procedures similar to those described above in Equation 9 for preparing I, where $R_5$ is $OSO_2R_9$, $CO_2R_7$, $OCH_3$, $SCH_3$ or $OCF_2H$. Compound T, where $R_5$ is $SO_2R_8$, is prepared by reacting S with an appropriate sulfinate salt, i.e., $KSO_2R_8$, in an inert solvent such as dimethylformamide at about 40° to 100° C. for 1 to 8 hours. Nitro compound T is reduced to amine IXi with iron powder and acetic acid in ethanol solvent at about 50° to 80° C. for 1 to 5 hours. Many starting compounds S may be prepared by analogous procedures described above in Equation 19 in U.S. Pat. No. 4,032,649 by one skilled in the art. Thus, an appropriate S-[6-nitro-5-chloro(or bromo)-2-vinyl]-N,N-dimethylthiocarbamate may be reacted with potassium hydroxide to form the corresponding 6-nitro-5-chloro(or bromo)-2-vinylthiophenol. This compound may then be heated at elevated temperatures, i.e., 150° to 250° C., to cause cyclization to form a mixture containing S and the corresponding 7-chloro(or bromo)-8-nitrothiochroman. Compound S may be isolated and purified by high resolution distillation or chromatography. 6-Chloro-7-nitro-2,3-dihydrobenzo[b]thiophen may be prepared by hydrolysis of the diazonium cobaltinitrite salt of 6-chloro-7-amino-2,3-dihydrobenzo[b]thiophene by obvious methods. For general details, refer to an analogous type reaction described in D. E. Bosewell, et al., J. Heterocycl. Chem., 5, 69 (1968).

The 7-amino-2,3-dihydrobenzo[b]thiophenes of Formula (IX) in Equation 5, where $R_5$ is $CH_3$, H, Cl, Br, $OCH_3$, $CO_2R_7$, $OSO_2R_9$, F, $CF_3$, $SCH_3$ or $OCF_2H$, can be prepared as shown in Equation 21 below.

Equation 21

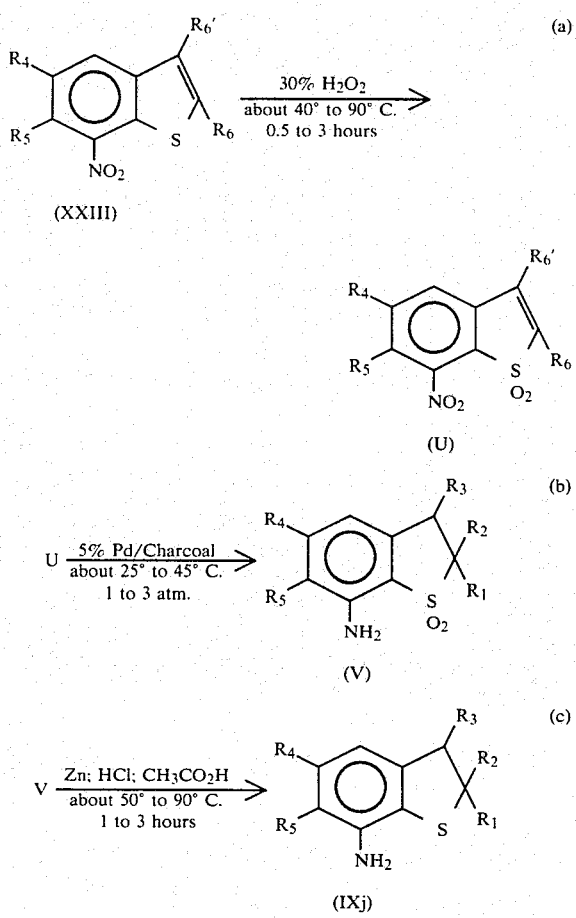

wherein
$R_1$, $R_2$ and $R_3$ are as originally defined, except at least one of $R_1$ or $R_2$ is H;
$R_4$ is H, Cl, $CH_3$, $CF_3$, $OCH_3$, Br, F or $OCF_2H$;
$R_5$ is H, $CH_3$, Cl, Br, $OCH_3$, $CO_2R_7$, $OSO_2R_9$, F, $CF_3$, $SCH_3$ or $OCF_2H$;
$R_6$ is H or $C_1$-$C_4$ alkyl; and
$R_6'$ is H or $CH_3$.

The stepwise reduction of benzo[b]thiophenenes to form 2,3-dihydrobenzo[b]thiophenes is known in the art, e.g., Bordwell and Stange, J. Am. Chem. Soc., 77, 5939 (1955) and Bordwell and McKellin, ibid., 73, 2251 (1951). The reactions of Equation 21 can be carried out using general procedures disclosed in the cited references. In the first step, a 7-nitrobenzo[b]thiophene of Formula (XXIII), is oxidized with 30% hydrogen peroxide in acetic acid at about 50° to 115° C. for 0.5 to 2 hours to form benzo[b]thiophene-1,1-dioxide U. Intermediate U is catalytically hydrogenated with 5% palladium-on-charcoal at 1 to 3 atmospheres of pressure, at 25° to 45° C., in ethanol solvent to form 2,3-dihydrobenzo[b]thiophene-1,1-dioxide V. In the last step, V is refluxed with zinc and concentrated hydrochloric acid in acetic acid solvent for 1 to 3 hours to produce IXj. Many of the starting 7-nitrobenzo[b]thiophenes of Formula (XXIII) are described hereinafter.

The 4-amino-2,3-dihydrobenzo[b]thiophenes of Formula (IX) in Equation 5, where $R_5$ is H, $CH_3$, Cl, Br, $OCH_3$, $CO_2R_7$, $OSO_2R_9$, $SO_2R_8$, F, $CF_3$, $SCH_3$ or $OCF_2H$, can also be prepared using procedures described in Equations 20 and 21 above. Thus, by starting with an appropriate 5-chloro-4-nitro-2,3-dihydrobenzo[b]thiophene, and carrying out the appropriate reactions described in Equation 20 above, one skilled in the art can prepare the subject compounds, where $R_2$ is $SO_2R_8$, $CO_2R_7$, $OSO_2R_9$, $OCH_3$, $SCH_3$ or $OCF_2H$. Similarly, by starting with an appropriate 5-(substituted)-4-nitrobenzo[b]thiophene, and carrying out the appropriate reactions described in Equation 21, the subject compounds can be prepared, where $R_5$ is H, $CH_3$, $OCH_3$, Cl, Br, $CO_2R_7$, $OSO_2R_9$, F, $CF_3$, $SCH_3$ or $OCF_2H$. The required starting 5-(substituted)-4-nitrobenzo[b]thiophenes are described hereinafter.

The 4- and 7-amino-2,3-dihydrobenzo[b]thiophenes of Formula (IX) in Equation 5, where $R_5$ is $SO_2NR_{10}R_{11}$ or $SO_2N(OCH_3)CH_3$ can be prepared by using methods described previously in Equation 10. By starting with an appropriate 4- or 7-acetamido-2,3-dihydrobenzo[b]thiophene, and carrying out the chlorosulfonation reactions described in Equation 10, one skilled in the art can prepare the subject 4- and 7-amino-2,3-dihydrobenzo[b]thiophenes of Formula (IX). The starting acetamides can be prepared by known methods, i.e., refluxing a 4- or 7-amino-2,3-dihydrobenzo[b]thiophene in acetic anhydride in the presence of sulfuric acid as catalyst. The latter amino compounds can be prepared by the Bucherer reaction, as described above in Equation 17.

The 4- and 7-aminobenzo[b]thiophenes of Formula (X) in Equation 6, where $R_5$ is H, $R_6$ is H or $C_1$-$C_4$ alkyl and $R_6'$ is H or $CH_3$, can also be prepared by the Bucherer reaction. By starting with an appropriate 4- or 7-hydroxybenzo[b]thiophene, and carrying out the reaction described in Equation 17, one skilled in the art can prepare the subject 4- and 7-aminobenzo[b]thiophenes of Formula (X). Many of the starting 4- and 7-hydroxybenzo[b]thiophenes are known in the literature.

The 4-aminobenzo[b]thiophenes of Formula (X) in Equation 6, where $R_5$ is H, $OCH_3$, Cl, Br, $CO_2R_7$, $OSO_2R_9$, $OCF_2H$ or F, can be prepared as shown in Equation 22 below.

Equation 22

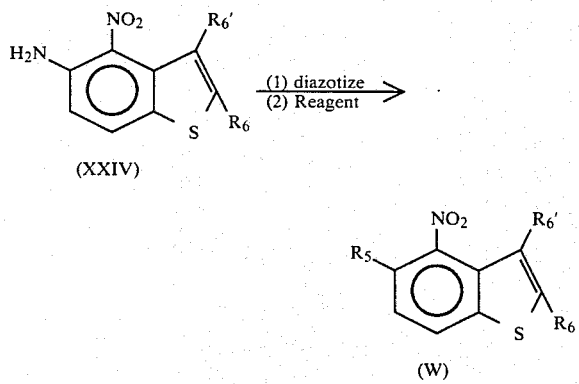

-continued
Equation 22

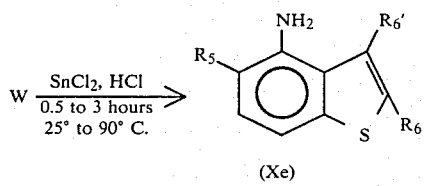

(Xe)

wherein
$R_5$ is H, $OCH_3$, Cl, Br, $CO_2R_7$, $OSO_2R_9$, $OCF_2H$ or F;
$R_6$ is H or $C_1$–$C_4$ alkyl; and
$R_6'$ is H or $CH_3$.

According to Equation 22, a 5-amino-4-nitrobenzo[b]thiophene of Formula (XXIV) is diazotized, then the diazonium salt is reacted with appropriate reagents to form intermediate W. Reduction of W then provides Xe. The diazonium salt can be prepared with sodium nitrite in dilute sulfuric acid (20 to 50%) at 0° to 10° C., a method well-known in the art for diazotizing aminobenzo[b]thiophenes, e.g. Bordwell and Stange, J. Am. Chem. Soc., 77, 5939 (1955). Intermediate W, where $R_5$ is as defined above, can be prepared from the diazonium salt using methods described heretofore in Equation 11 by one skilled in the art. The reduction step to form Xe from W can be carried out by any of several methods known in the art for reducing nitrobenzo[b]thiophenes to aminobenzo[b]thiophenes, e.g., Bordwell and Albisetti, J. Am. Chem. Soc., 70, 1955 (1948); and Martin-Smith and Reid, J. Chem. Soc., 938 (1960). Thus, refluxing W with stannous chloride and hydrochloric acid in acetic acid solvent for 0.5 to 3 hours can provide Xe. The starting 5-amino-4-nitrobenzo[b]thiophenes of Formula (XXIV) can be prepared by one skilled in the art according to the teachings of Bordwell and Stange, J. Am. Chem. Soc., 77, 5939 (1955); Fries et al., Ann, 527, 83 (1936); and G. Karimov et al., Dokl, Akad. Nauk. Tadzh. SSR, 13, 41 (1970), Chem. Abstr. 75:5605j.

The 7-aminobenzo[b]thiophenes of Formula (X) in Equation 6, where $R_5$ is H, $CH_3$, $OCH_3$, Cl, Br, F or $CF_3$, can be prepared as shown in Equation 23.

Equation 23

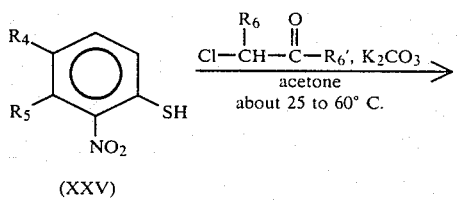

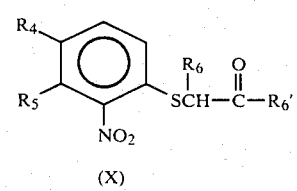

(X)

-continued
Equation 23

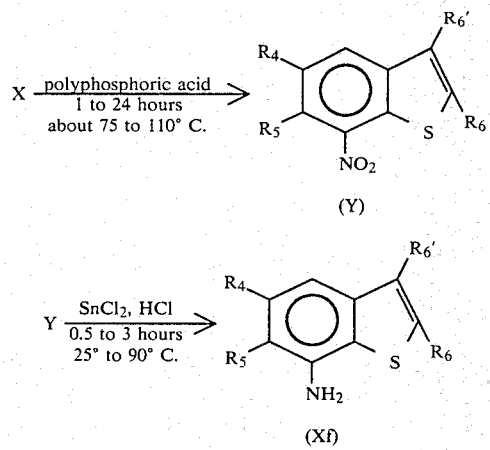

wherein
$R_4$ is as originally defined;
$R_5$ is H, $CH_3$, $OCH_3$, Cl, Br, F or $CF_3$;
$R_6$ is H or $C_1$–$C_4$ alkyl; and
$R_6'$ is $CH_3$.

The procedure of Equation 23 involves three reaction steps: (1) refluxing an appropriate 3-(substituted)-2-nitrothiophenol with an α-chloroketone such as chloropropane in the presence of a base such as $K_2CO_3$ in acetone solvent for 1 to 10 hours to form intermediate X; cyclizing X in polyphosphoric acid at about 100° for 1 to 24 hours to form a 6-(substituted)-7-nitrobenzo[b]thiophene Y; and reducing Y to form Xf. The reduction can be carried out by procedures described above in Equation 22. The cyclization of thiophenoxypropanones to form benzo[b]thiophenes is known in the art, e.g., Karimov et al., Dokl, Akad. Nauk. Tadzh, USSR, 13, 41 (1970), Chem. Abstr. 75:5605j; and Yasuo, Nippon Kagaku Zasshi 88, 758 (1967), Chem. Abstr. 69:59018g.

Also, by substituting chloroacetaldehyde diethyl acetal or 2-chloropropionaldehyde diethyl acetal for the α-chloroketone in Equation 23 above, and carrying out the procedure described therein, one skilled in the art can prepare 7-aminobenzo[b]thiophenes Xf, where $R_5$ is as defined above, $R_6$ is H or $CH_3$ and $R_6'$ is H.

The 4- and 7-aminobenzo[b]thiophenes of Formula (X) in Equation 6, where $R_5$ is $SO_2R_8$, $CO_2R_7$, $OSO_2R_9$, $OCH_3$, $SCH_3$ or $OCF_2H$, $R_6$ is H or $C_1$–$C_4$ alkyl and $R_6'$ is H or $CH_3$, can be prepared by methods analogous to those described previously in Equation 9. Thus, by starting with an appropriate 6-chloro-7-nitrobenzo[b]thiophene or 5-chloro-4-nitrobenzo[b]thiophene, and carrying out the appropriate reactions described in Equation 9, one skilled in the art can prepare the subject compounds of Formula (X). The starting 5-chloro-4-nitrobenzo[b]thiophenes and 6-chloro-7-nitrobenzo[b]thiophenes are described above in Equations 22 and 23, respectively.

The 4- and 7-aminobenzo[b]thiophenes of Formula (X) in Equation 6, where $R_5$ is $NO_2$, $SO_2NR_{10}R_{11}$ or $SO_2N(OCH_3)CH_3$, $R_6$ is $C_1$–$C_4$ alkyl and $R_6'$ is $CH_3$, can be prepared by methods described heretofore in Equation 10. Thus, by starting with an appropriate 4- or 7-acetamidobenzo[b]thiophene, and carrying out the nitration procedures described in Equation 10, one skilled in the art can prepare the subject 4- or 7- aminobenzo[b]thiophene of Formula (X), where $R_5$ is $NO_2$. Similarly, by carrying out the chlorosulfonation reactions on an appropriate 4- or 7-acetamidobenzo[b]-thiophene, one can prepare the subject 4- or 7-aminobenzo[b]thiophene of Formula (X), where $R_5$ is $SO_2NR_{10}R_{11}$ or $SO_2N(OCH_3)CH_3$. The nitration of acetamidobenzo[b]thiophenes is known in the art, e.g., Bordwell and Stange, J. Am. Chem. Soc., 77, 5939 (1955). The chlorosulfonation of benzo[b]thiophenes is also known, e.g. Pailer, Monatsh 92, 677 (1961).

The 4- and 7-aminobenzo[b]thiophene-1,1-dioxides of Formula (X) in Equation 6 ($Q_1$=$SO_2$), where $R_5$ is other than $CO_2R_7$, $OSO_2R_9$ or $SCH_3$, and $R_4$ is other than $SCH_3$, can be prepared from corresponding 4- and 7-aminobenzo[b]thiophenes. The preparation involves three steps: (1) acetylation of the amine with acetic anhydride to form a 4- or 7-acetamidobenzo[b]thiophene; (2) oxidation of this compound with 30% hydrogen peroxide to form a 4- or 7-acetamidobenzo[b]thiophene-1,1,-dioxide; and (3) deacetylation of this compound to form a 4- or 7-aminobenzo[b]thiophene-1,1-dioxide of Formula (X). The acetylation step can be carried out in refluxing acetic anhydride with sulfuric acid catalyst by obvious methods. The oxidation step can be carried out in acetic acid solvent at 50° to 115° C. for 0.5 to about 3 hours, according to the teachings of Bordwell and Stange, J. Am. Chem. Soc., 77, 5939 (1955). The deacetylation step can be carried out by hydrolysis with hydrochloric acid or saponification with sodium hydroxide by methods described heretofore in Equation 10.

Alternatively, certain 4- and 7-aminobenzo[b]-thiophene-1,1-dioxides of Formula (X) described below can be prepared from corresponding 4- and 7-nitrobenzo[b]thiophenes. This involves two steps: (1) oxidation of the nitro compound with 30% hydrogen peroxide by methods described above to form a 4- or 7-nitrobenzo[b]thiophene-1,1-dioxide; and (2) reduction of this nitro compound to form a 4- or 7-aminobenzo[b]thiophene-1,1-dioxide of Formula (X). The reduction step can be carried out with warm stannous chloride and hydrochloric acid in ethanol solvent according to the teachings of Bordwell and Albisetti, J. Am. Chem. Soc., 70, 1955 (1948) and Fries et al., Ann. 527 83 (1936). The starting 4- and 7-nitrobenzo[b]thiophenes have been described heretofore. By this method the 4- and 7-aminobenzo[b]-thiophene-1,1-dioxides of Formula (X) can be prepared, where $R_5$ is H, Cl, Br, $OCH_3$, $SO_2R_8$, $CO_2R_7$ or $OSO_2R_9$, $CH_3$, F, $CF_3$ or $OCF_2H$, and $R_4$ is other than $SCH_3$.

The 4- and 7-amino-2,3-dihydrobenzo[b]thiophene-1,1-dioxides of Formula (IX) in Equation 5 (Q=$SO_2$), where $R_5$ is other than $CO_2R_7$, $OSO_2R_9$, $NO_2$ or $SCH_3$, and $R_4$ is other than $SCH_3$, can be prepared from corresponding 4- and 7-aminobenzo[b]thiophenes. The preparation involves four steps: (1) acetylation of the amine with acetic anhydride to form a 4- or 7-acetamidobenzo[b]thiophene; (2) oxidation of this compound with 30% hydrogen peroxide to form a 4- or 7-acetamidobenzo[b]thiophene-1,1-dioxide; (3) catalytic reduction of this compound with 5% palladium-on charcoal to form a 4- or 7-acetamido-2,3-dihydro-benzo[b]thiophene-1,1-dioxide; and (4) deacetylation of this compound to form a 4- or 7-amino-2,3-dihydrobenzo[b]thiophene-1,1-dioxide of Formula (IX). The acetylation, oxidation and deacetylation steps can be carried out by methods described above for preparing 4- and 7-aminobenzo[b]thiophene-1,1-dioxides. The reduction step is best carried out at 25° to 40° C. at 1 to 3 atmospheres of pressure in an inert solvent such as ethanol. The catalytic reduction of benzo[b]thiophene-1,1-dioxides to form 2,3-dihydrobenzo[b]thiophene-1,1-dioxides is known in the art, e.g., Bordwell and Stange, J. Am. Chem. Soc., 77, 5939 (1955) and Bordwell and McKellin, ibid, 73, 2251 (1951).

Also, certain 4- and 7-amino-2,3-dihydrobenzo[b]thiophene-1,1-dioxides of Formula (IX) described below can be prepared from corresponding 4- and 7-nitrobenzo[b]thiophenes. By starting with an appropriate 5-(substituted)-4-nitrobenzo[b]thiophene or 5- or 6-(substituted)-7-nitrobenzo[b]thiophene, and carrying out the reactions heretofore described in Equations 21a and 21b, one skilled in the art can prepare 4- and 7-amino-2,3-dihydrobenzo[b]thiophene-1,1-dioxides of Formula (IX), where $R_5$ is H, Cl, Br, $CH_3$, $OCH_3$, $SO_2R_8$, $CO_2R_7$, $OSO_2R_9$, F, $CF_3$ or $OCF_2H$ and $R_4$ is other than $SCH_3$. The starting 5-(substituted)-4-nitrobenzo[b]thiophenes and 6-(substituted)-7-nitrobenzo[b]thiophenes have been described heretofore.

In addition, the 4- and 7-amino-2,3-dihydrobenzo[b]-thiophene-1,1-dioxides of Formula (IX), where $R_5$ is other than $CO_2R_7$, $OSO_2R_9$ or $SCH_3$ and $R_4$ is other than $SCH_3$, can be prepared from corresponding 4- and 7-amino-2,3-dihydrobenzo[b]thiophenes. The preparation involves three steps: (1) acetylation of the amine with acetic anhydride to form a 4- or 7-acetamido-2,3-dihydrobenzo[b]thiophene; (2) oxidation of this compound with 30% hydrogen peroxide in acetic acid at 15° to 80° C. for 0.5 to about 5 hours to form a 4- or 7-acetamido-2,3-dihydrobenzo[b]thiophene-1,1-dioxide; and (3) deacetylation of this compound to form the subject compounds of Formula (IX). The acetylation and deacetylation reactions can be run by methods described above for preparing 4- and 7-aminobenzo[b]-thiophene-1,1-dioxides from corresponding amines.

Similarly, the 4- and 7-amino-2,3-dihydrobenzo[b]thi-ophene-1-oxides of Formula (IX) in Equation 5 (Q=SO), where $R_5$ is other than $CO_2R_7$, $OSO_2R_9$ or $SCH_3$ and $R_4$ is other than $SCH_3$, can be prepared from corresponding 4- and 7-amino-2,3-dihydrobenzo[b]thiophenes. The preparation involves three steps: (1) acetylation of the amine with acetic anhydride to form a 4- or 7-acetamido-2,3-dihydrobenzo[b]thiophene; (2) oxidation of this compound with one mole equivalent of m-chloroperbenzoic acid to form a 4- or 7-acetamido-2,3-dihydrobenzoic[b]thiophene-1-oxide; and (3) deacetylation of this compound to form the subject compound of Formula IX. The oxidation step can be run in an inert solvent such as methylene chloride at about 0° to 10° C. for 1 to 16 hours, according to the teachings of Johnson and McCants, Jr., J. Am. Chem. Soc., 87, 1109 (1965). The acetylation and deacetylation steps can be run by methods described above. In addition, many sulfones and sulfoxides of Formulae (IX) and (X) in Equations 5 and 6 can be prepared by one skilled in the art by (1) oxidation of an appropriate 6-chloro-7-nitro-2,3-dihydrobenzo[b]thiophene, 5-chloro-4-nitro-2,3-dihydrobenzo[b]thiophene, or 6-chloro-7-nitrobenzo[b]thiophene, or 5-chloro-4-nitrobenzo[b]thiophene, described heretofore, to the corresponding sulfone or sulfoxide by general procedures described above or known in the art, and (2) subsequently carrying out the reactions described heretofore in Equations 9 and 20. By this procedure, the sulfones and sulfoxides of Formulae (IX) and (X) can be prepared where $R_4$ is H and $R_5$ is $CO_2R_7$, $OSO_2R_9$, $SO_2R_8$, $OCH_3$, $SCH_3$ or $OCF_2H$.

Also, sulfonamides of Formula (VI) in Equations 3 and 7 can be oxidized to corresponding dihydrobenzo[b]thiophene-1-oxides or 1,1-dioxides by general methods described above by one skilled in the art, wherein $R_4$ and $R_5$ are other than $SCH_3$. Similarly, sulfonamides of Formula (VII) in Equation 4 can be oxidized to corresponding 1,1-dioxides, wherein $R_4$ and $R_5$ are other than $SCH_3$.

The 4- and 7-amino-benzofurans, -benzo[b]thiophenes and -benzo[b]thiophene-1,1-dioxides of Formula (X) in Equation 6, where $R_6$ or $R_6'$ is Cl or Br, can be prepared by halogenation reactions by obvious methods. Thus, the compounds are prepared by (a) heating an appropriate 4- or 7-acetamido-benzofuran, -benzo[b]thiophene or -benzo[b]thiophene-1,1-dioxide with chlorine or bromine at about 10° to 60° C. for 0.5 to 5 hours in an inert solvent such as chloroform or acetic acid, followed by (b) deacetylation of the resulting halogenated product by one of the methods described previously in Equation 10.

It will also be apparent that the amines of Formula (V) in Equations 1, 2, 3a and 4a are important intermediates for preparing the compounds of this invention.

The pyrimidines and triazines of Formula (Va) to (Ve) below are either known or can be prepared by obvious methods by one skilled in the art. For instance, the synthesis of pyrimidines and triazines of the general formula Va has been reviewed in "The Chemistry of Heterocyclic Compounds", a series published by Interscience Publishers, Inc., New York and London. 2-Aminopyrimidines are described by D. J. Brown in "The Pyrimidines", Vol. 16 of this series. 2-Amino-1,3,5-triazines are reviewed by E. M. Smolin and L. Rapaport in "s-Triazines and Derivatives", Vol. 13 of the same series. The synthesis of triazines is also described by F. C. Schaefer, U.S. Pat. No. 3,154,547 and by K. R. Huffman and F. C. Schaefer, J. Org. Chem., 28, 1812 (1963). The synthesis of the bicyclic amines of the general formulae (Vc) and (Vd) are described in European Patent Application No. 80-300,505.7 and that of the general formula (Vb) in European Patent Publication No. 46,677. Aminopyrimidines substituted by an acetal group, i.e.,

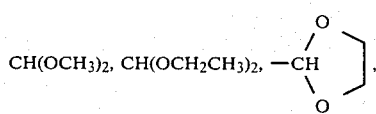

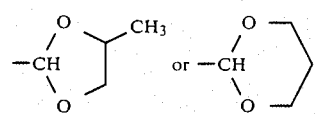

can be prepared by the general methods, or suitable modifications thereof which are known to those skilled in the art, taught in European Patent Application No. 82-306,492.8 and W. Braker et al., J. Am. Chem. Soc., 69, 3072 (1947). Aminopyrimidines and -triazines substituted by halogenoalkoxy or halogenalkylthio groups, i.e., $OCH_2CH_2Cl$, $OCH_2CH_2Br$, $OCH_2CH_2F$, $OCH_2CF_3$ or $GCF_2T$, wherein G and T are as defined above, can be prepared by the general methods, or suitable modifications thereof which are known to those skilled in the art, taught in South African patent application Nos. 825,045 and 825,671. Triazines of the general formula (Ve) are described in U.S.S.N. 377,371.

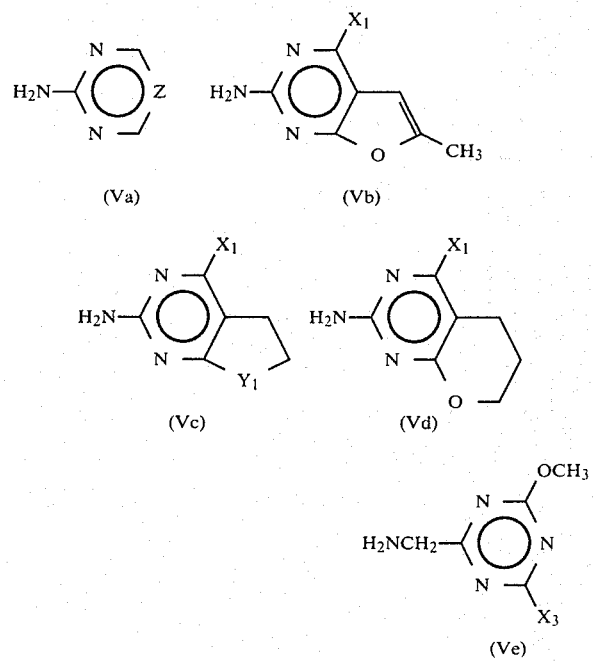

Triazines of Formula (Vf) may be prepared according to the methods outlined in Equations 24 and 25.

Equation 24

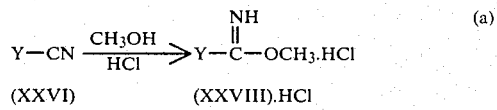

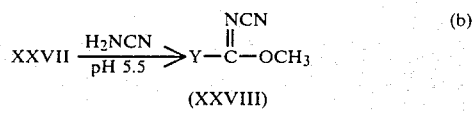

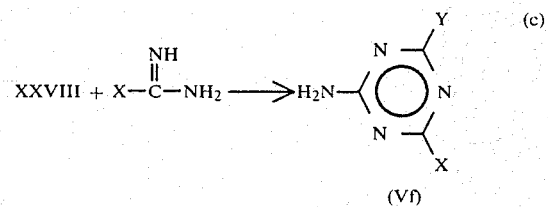

wherein
X is $CH_3$ or $OCH_3$; and

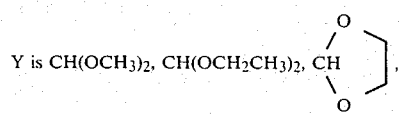

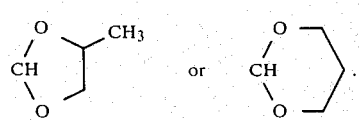

Equation 25

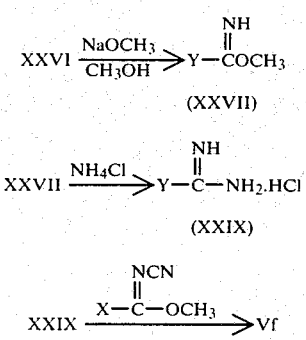

wherein

X and Y are as defined in Equation 24.

The reaction of Equation 24a is carried out according to the teachings of J. M. McElvain and R. L. Clarke, J. Amer. Chem. Soc., 69, 2657 (1947), in which the preparation of ethyl diethoxyiminoacetate is described. The intermediate N-cyanoimidate of Formula (XXVIII) may be prepared according to the teaching of D. Lwowski in Synthesis, 1971, 263, by reacting XXVII with cyanamide at pH 5.5, and this may be condensed according to reaction 24c with either acetamidine or O-methyl isourea in an alcoholic solvent at 25° to 80° C. to provide the appropriate triazines. Alternatively, the reaction of Equation 25a, described for substituted acetonitriles by F. C. Schaefer and G. A. Peters in J. Org. Chem., 26, 412 (1961), may be used to convert nitrile of Formula (XXVI) to the corresponding iminoester. The free base may be carried on through reactions 25b and 25c, or, alternatively, converted to the amidinium hydrochloride salt XXIX as described in the aforementioned reference, and condensed with either methyl N-cyanoacetimidate or with dimethyl N-cyano imidocarbonate in the presence of one equivalent of sodium methoxide to provide the triazines of Formula (Vf).

Preparations of 3-amino-1,2,4-triazoles of Formula (V) in Equations 1, 2, 3a and 4a are known in the art and 1,2,4-triazoles are reviewed in The Chemistry of Heterocyclic Compounds "Triazoles 1,2,4" (John Wiley and Sons, New York, 1981). Commonly used starting materials containing nitrogen are N-aminoguanidine, hydrazine, alkylhydrazines, cyanamide, ethyl cyanoacetimidate, dimethyl cyanodithioimidocarbonate, dimethyl cyanoimidocarbonate, ethoxymethylenecyanamide, and acylhydrazines. Some literature synthesis are illustrated below. Using these techniques or suitable modifications that would be apparent to one skilled in the art, the 3-amino-1,2,4-triazole intermediates can be readily prepared.

Heating equimolar amounts of ethyl propionimidate hydrochloride and N-aminoguanidine nitrate in pyridine gives 3-amino-5-ethyltriazole; German Pat. No. 1,073,499 (1960); Berichte, 96, 1064 (1963).

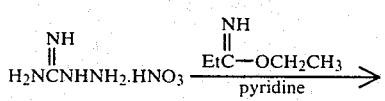

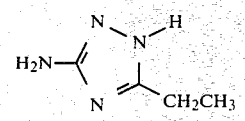

Condensation of hydrazine with ethyl N-cyanoacetimidate yields 3-amino-5-methyltriazole; Journal of Organic Chemistry, 28, 1816 (1963).

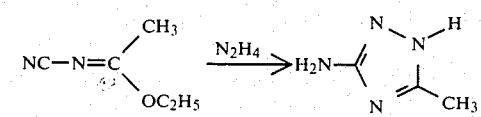

U.S. Pat. No. 2,835,581 (1958) teaches the preparation of 3-amino-5-(hydroxymethyl)triazole from N-aminoguanidine and glycolic acid and British Pat. No. 736,568 (1955) describes the synthesis of 3-amino-5-mercaptotriazole.

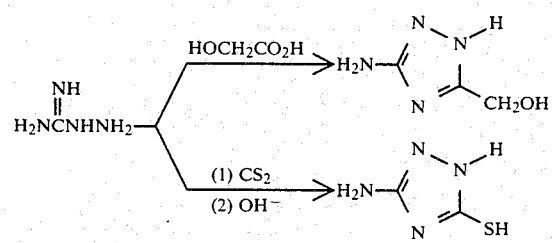

Condensing hydrazine with dimethyl cyanodithioimidocarbonate in acetonitrile gives 3-amino-5-methylthio-1,2,4-triazole while reaction of hydrazine with dimethyl-N-cyanoimidocarbonate produces 3-amino-5-methoxy-1,2,4-triazole; Journal of Organic Chemistry, 39, 1522 (1974).

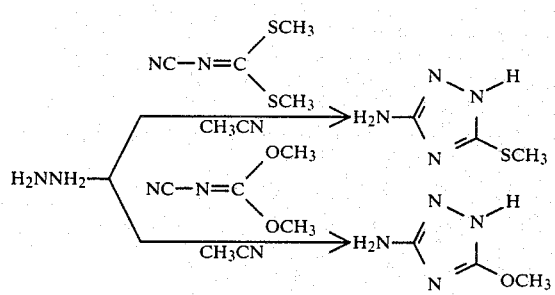

Reaction of substituted hydrazines with N-cyanothioimidocarbonates (prepared according to the procedure given in D. M. Wieland, Ph.D. Thesis, 1971, pp. 123–124) yields disubstituted aminotriazoles as shown below.

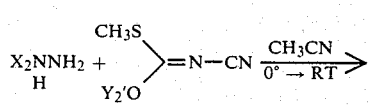

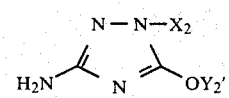

-continued ($Y_2' = CH_3$ or $C_2H_5$)

Many of the aminoheterocyclic intermediates of Formula (V) where $R_{12}$ is methyl may be prepared by a two-step procedure analogous to that described for Vg in Equation 27 by one skilled in the art.

Equation 27

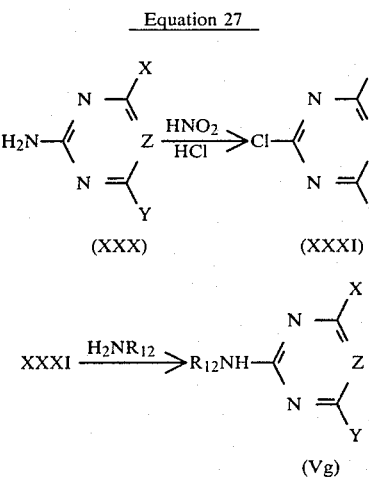

wherein

X, Y and Z are as originally defined and $R_{12}$ is $CH_3$.

A solution of the amine XXX in concentrated hydrochloric acid is treated with sodium nitrite solution and the chloro compound XXXI is isolated in the usual manner by filtration of the acidic solution. A representative procedure is described by Bee and Rose in J. Chem. Soc. C, 2031 (1966), for the case in which Z=CH, and X=Y=OCH$_3$. Displacement of the chlorine of XXXI may be accomplished by heating with an excess of methylamine in water to obtain the methylamino heterocycle Vg.

Equation 28 below illustrates the preparation of the required methyl pyrimidinyl carbamates and methyl triazinyl carbamates of Formula (VIII) in Equations 3 and 4. By obvious modifications, other methyl carbamates of Formula (VIII) may be prepared by this method.

Equation 28

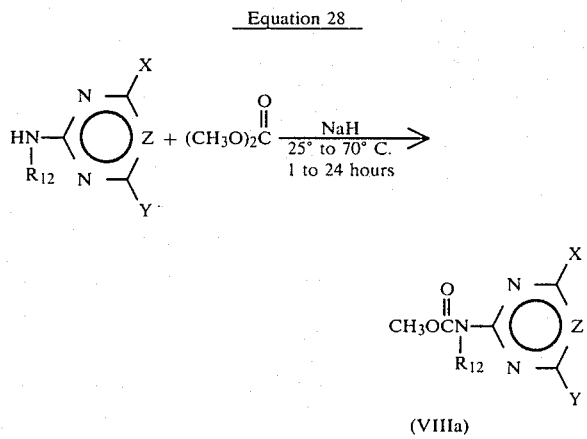

wherein

X, Y, Z and $R_{12}$ are as originally defined, except Y is not $NH_2$ or $NHCH_3$.

According to Equation 28, a heterocyclic amine is reacted with two equivalents of sodium hydride and excess dimethyl carbonate to form VIIIa. The reaction is run in an inert solvent such as tetrahydrofuran at 25° C. to reflux for 1 to 24 hours. The product is isolated by (a) adding about two equivalents of concentrated hydrochloric acid under nitrogen of 0° to 30° C.; (b) filtering; and (c) separating out the organic phase, then drying (sodium sulfate and/or magnesium sulfate) and concentrating to dryness in vacuo. The product VIIIa may be purified further by recrystallization or chromatography procedures.

Agriculturally suitable salts of compounds of Formulae (I), (I'), (II) and (II') are also useful herbicides and can be prepared by a number of ways known to the art. For example, metal salts can be made by treating compounds of Formulae (I), (I'), (II) or (II') with a solution of alkali or alkaline earth metal salt having a sufficiently basic anion (e.g., hydroxide, alkoxide, carbonate or hydride). Quaternary amine salts can be made by similar techniques.

Salts of compounds of Formulae (I), (I'), (II) and (II') can also be prepared by exchange of one cation to another. Cationic exchange can be effected by direct treatment of an aqueous solution of a salt of a compound of Formulae (I), (I'), (II) or (II') (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formulae (I), (I'), (II) or (II') (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water soluble, e.g., a potassium, sodium or calcium salt.

Acid addition salts, useful in this invention, can be obtained by reacting a compound of Formulae (I), (I'), (II) or (II') with a suitable acid, e.g, p-toluenesulfonic acid, trichloroacetic acid or the like.

In the following examples all parts are by weight and temperature in °C. unless otherwise indicated.

EXAMPLE 1

2,3-Dihydro-2,2-dimethyl-7-benzofuransulfonyl chloride

A diazonium salt was prepared by adding 13.8 g of sodium nitrite to a suspension of 32.6 g of 7-amino-2,3-dihydro-2,2-dimethylbenzofuran and 40 ml of concentrated sulfuric acid in 200 ml water cooled 0° to 5° C. After stirring for about 0.4 hour at 0° to 5° C., the diazonium salt suspension was poured in one portion into a mixture consisting of 170 ml of acetic acid, 40 ml of concentrated hydrochloric acid, 17 g of cupric chloride dehydrate and 30 ml of sulfur dioxide and cooled at 10° C. by an ice-water bath. The mixture was stirred about 1 hour at 15° to 25° C. Then 400 ml of 1-chlorobutane and 200 ml of water was added and the mixture was stirred and heated at 35° C. for 5 hours. After cooling to room temperature, the organic layer was separated, washed with saturated aqueous NaHCO$_3$ and water, and dried over sodium sulfate for 0.5 hour. The solvent was evaporated under reduced pressure at less than 45° C. to give 26 g of crude 2,3-dihydro-2,2-dimethyl-7-benzofuransulfonyl chloride as an oil.

EXAMPLE 2

2,3-Dihydro-2,2-dimethyl-7-benzofuransulfonamide

A solution of 26 g of 2,3-dihydro-2,2-dimethyl-7-benzofuransulfonyl chloride prepared in Example 1, in 130 ml of tetrahydrofuran, was cooled in an ice-water bath while about 30 ml of concentrated aqueous ammonium hydroxide was added portionwise at 10° to 30° C. The resulting suspension was stirred at room temperature for 3 hours, then the solvent was evaporated under reduced pressure. The residue was stirred in 150 ml of water for 0.5 hour, then filtered. The crude, wet solid was dissolved in chloroform and dried over sodium sulfate. The solvent was evaporated under reduced pressure to give a dry solid. The solid was washed once with about 100 ml of hot toluene to give 20 g of 2,3-dihydro-2,2-dimethyl-7-benzofuransulfonamide, m.p. 163°–165° C.

Anal. Calcd. for $C_{10}H_{13}NO_3S$: C, 52.8; H, 5.8; N, 6.2; Found: C, 52.5; H, 5.7; N, 6.1.

EXAMPLE 3

N-(Butylaminocarbonyl)-2,3-dihydro-2,2-dimethyl-7-benzofuransulfonamide

A solution of 19 g of 2,3-dihydro-2,2-dimethyl-7-benzofuransulfonamide prepared in Example 2 and 9.9 g of n-butyl isocyanate in 200 ml of 2-butanone was refluxed with 11.5 g of anhydrous potassium carbonate for 7 hours. The resulting mixture was concentrated to dryness in vacuo. The residue was taken up in 400 ml of water and extracted once with 100 ml of ethyl ether. The aqueous layer was acidified with 2N HCl and the resulting mixture was filtered and suction dried. The still slightly wet solid was washed once with 100 ml of hot acetonitrile, then suction dried an additional 8 hours to give 23 g of N-(butylaminocarbonyl)-2,3-dihydro-2,2-dimethyl-7-benzofuransulfonamide, m.p. 200°–203° C.

Anal. Calcd. for $C_{15}H_{22}N_2O_4S$: C, 55.2; H, 6.8; N, 8.6; Found: C, 54.8; H, 6.6; N, 8.5.

EXAMPLE 4

2,3-Dihydro-2,2-dimethyl-7-benzofuransulfonyl isocyanate

A suspension of 22 g of the N-(n-butylaminocarbonyl)-2,3-dihydro-2,2-dimethyl-7-benzofuransulfonamide prepared in Example 3, in 125 ml of xylene containing 0.3 g of DABCO was heated at 130°–135° C. while 5.3 ml of phosgene was added portionwise at a rate to maintain a reflux temperature of 130°–135° C. The mixture was refluxed for an additional 1.5 hours, cooled under nitrogen, and concentrated to dryness in vacuo. A sample of the crude oily product displayed a characteristic sulfonyl isocyanate band in the IR at 2200 $cm^{-1}$.

EXAMPLE 5

N-[(4,6-Dimethylpyrimidin-2-yl)aminocarbonyl]-2,3-dihydro-2,2-dimethyl-7-benzofuransulfonamide To a solution of 1.2 g of 2-amino-4,6-dimethylpyrimidine in 25 ml of tetrahydrofuran was added 2.5 g of 2,3-dihydro-2,2-dimethyl-7-benzofuransulfonyl isocyanate prepared above. After a slight exotherm the solution was stirred at room temperature for 4 hours. The solution was concentrated in vacuo to give a viscous oil that precipitated a solid from 10 ml of acetonitrile. The solid was recrystallized from acetonitrile to give 2 g of N-[(4,6-dimethylpyrimidin-2-yl)aminocarbonyl]-2,3-dihydro-2,2-dimethyl-7-benzofuransulfonamide, m.p. 203°–206° C. The IR spectrum showed a carbonyl absorption at 1680 $cm^{-1}$ indicative of a sulfonylurea.

Anal. Calcd. for $C_{17}H_{20}N_4O_4S$: C, 54.2; H, 5.4; N, 14.9; Found: C, 54.3; H, 5.4; N, 15.2.

EXAMPLE 6

Methyl (4-methoxy-6-methylpyrimidin-2-yl)carbamate

To a suspension of 50 g of 2-amino-4-methoxy-6-methylpyrimidine in 1000 ml of tetrahydrofuran was added portionwise, under a nitrogen atmosphere, 42.8 g of 50% sodium hydride while cooling the reaction flask in an ice-water bath. After stirring one hour at 25° C., 58.5 g of dimethylcarbonate was added dropwise at 5° to 25° C. The suspension was stirred about 16 hours at ambient temperature, then 80 ml of concentrated hydrochloric acid was added dropwise while maintaining a reaction temperature of 20° to 25° C. with external ice-bath cooling. The suspension was stirred 0.5 hour, filtered, and the filtrate was dried over sodium sulfate and then concentrated in vacuo. The residue was recrystallized from hexane to yield 54 g of the title compound, m.p. 89°–92.5° C.

EXAMPLE 7

7-Amino-2,3-dihydro-2-methylbenzo[b]thiophene (2-Aminophenyl)allylsulfide (80 g) was heated at 250°–280° C. for 3 hours, cooled, then subjected to spinning band distillation through a 20 cm column using a 5:1 reflux ratio. The fraction distilling at 80°–82° at 0.25 mm of mercury was collected (18.0 g) and shown by NMR spectrum analysis to be the title compound in approximately 90% purity.

NMR ($CDCl_3$)δ: 7.0–6.3 (m, 3H, ArH); 3.9 (m, 1H, CH); 3.5 (broad, 2H, $NH_2$); 3.5–2.6 (m, 2H, $CH_2$); and 1.35 (d, 3H, $CH_3$).

EXAMPLE 8

7-Acetamido-2,3-dihydro-2-methylbenzo[b]thiophene

To a solution of 18.0 g of 7-amino-2,3-dihydro-2-methylbenzo[b]thiophene (Example 7) in 100 ml of 1-chlorobutane was added a solution of 13.0 ml of acetic anhydride in 20 ml of 1-chlorobutane. After the exothermic reaction subsided, the mixture was refluxed for 0.3 hour, cooled in an ice-bath and filtered. The isolated solid was washed with 1-chlorobutane to yield 15.2 g of the title compound; m.p. 125°–127° C.

NMR ($CDCl_3$)δ: 7.8–6.7 (m, 4H, ArH+NH); 4.0 (m, 1H, CH); 3.6–2.8 (m, 2H, $CH_2$); 2.2 (s, 3H, $CH_3$); and 1.4 (d, 3H, $CH_3$).

EXAMPLE 9

7-Acetamido-2,3-dihydro-2-methylbenzo[b]thiophene-1,1-dioxide

To a solution of 24.7 g of 7-acetamido-2,3-dihydro-2-methylbenzo[b]thiophene (Example 8) in 100 ml of glacial acetic acid was added dropwise 60 ml of a 30% aqueous solution of hydrogen peroxide. The reaction temperature rose to 65° C. during the addition. The mixture was heated at 65°–75° C. for one hour, cooled to 25° C., diluted with water and extracted with methylene chloride. The extract was washed with water saturated with sodium bisulfite, dried over magnesium sulfate and concentrated in vacuo. The oily residue was crystallized from 1-chlorobutane to yield 14.3 g of the title compound as light yellow crystals; m.p. 115°–117° C.

NMR (CDCl$_3$)δ: 8.4–7.0 (m, 4H, ArH+NH); 3.8–2.7 (m, 3H, CH$_2$+CH); 2.2 (s, 3H, CH$_3$); and 1.5 (d, 3H, CH$_3$).

EXAMPLE 10

2,3-Dihydro-2-methyl-7-benzo[b]thiophenesulfonamide-1,1-dioxide

A. A solution of 18.6 g of 7-acetamido-2,3-dihydro-2-methylbenzo[b]thiophene-1,1-dioxide (Example 9) in 100 ml of concentrated hydrochloric acid was refluxed for one hour to yield a suspension containing the hydrochloride salt of 7-amino-2,3-dihydro-2-methylbenzo[b]thiophene-1,1-dioxide.

B. This suspension was diluted with 25 ml of glacial acetic acid, cooled to −5° C. and treated with a solution of 6.4 g of sodium nitrite in 10 ml of water such that the temperature did not rise above 5° C. The mixture was stirred for 0.5 hour at 0° C., then added in one portion to a suspension cooled at −7° C. and containing 50 ml of concentrated hydrochloric acid, 50 ml of glacial acetic acid, 2.0 g cupric chloride dihydrate and 10 ml of liquified sulfur dioxide. The mixture was stirred at 20° C. for two hours then diluted with excess water to yield a precipitate. The mixture was filtered and the solid residue was washed with water to yield 2-methyl-2,3-dihydro-7-benzo[b]thiophenesulfonyl chloride 1,1-dioxide as a crude solid.

C. This solid was dissolved in methylene chloride and contacted with 7 ml of liquified ammonia at −10° C. The mixture was stirred at 20° C. for 16 hours, then filtered and the solids were washed with water and ether. The wet, solid residue was suspended in benzene and refluxed under a Dean-Stark trap until no more water distilled from the suspension. The suspension was cooled and filtered to yield 11.4 g of the title compound; m.p. 167°–169° C.

NMR (CDCl$_3$+DMSO)δ: 8.1–7.5 (m, 3H, Ar); 7.1 (broad, 2H, NH$_2$); 3.8–2.5 (m, 3H, CH$_2$+CH); and 1.5 (d, 3H, CH$_3$).

IR (nujol): 3300, 3200 cm$^{-1}$ (NH$_2$).

EXAMPLE 11

N-[(4-Methoxy-6-methylpyrimidin-2-yl)aminocarbonyl]-2,3-dihydro-2-methyl-7-benzo[b]thiophenesulfonamide-1,1-dioxide A suspension of 1.15 g 2,3-dihydro-2-methyl-7-benzo[b]thiophenesulfonamide-1,1-dioxide (Example 10) in 20 ml of dry methylene chloride was purged with nitrogen. To the slurry was added carefully 3.0 ml of a 20% toluene solution of trimethyl aluminum (Aldrich Chemicals) while cooling the flask at 10° to 30° C. After stirring for 0.2 hour, 0.9 g of methyl (4-methoxy-6-methylpyrimidin-2-yl)carbamate (Example 6) was added in one portion, and the suspension was refluxed under nitrogen atmosphere for 24 hours. The suspension was cooled in an ice-water bath while 20 ml of 1N hydrochloric acid was slowly added. After several minutes of stirring, the organic layer was separated, washed with water followed by water saturated with sodium chloride (brine), then dried over magnesium sulfate and concentrated in vacuo. The residue was triturated with chloroform and methylene chloride to yield 0.3 g of the title compound; m.p. 224°–226° C.

NMR (CDCl$_3$+DMSO)δ: 10.3 (broad, 1H, NH); 8.2–7.6 (m, 3H, Ar); 6.3 (s, 1H, CH); 4.0 (s, 3H, OCH$_3$); 3.7–2.8 (m, 3H, CH$_2$+CH); 2.5 (s, 3H, CH$_3$); and 1.5 (d, 3H, CH$_3$).

IR (nujol): 1700 cm$^{-1}$ (c=o)

EXAMPLE 12

N-t-Butyl-2-(2-methyl-2-propenylthio)benzenesulfonamide

To an ice-cooled solution of 42.6 g of N-t-butylbenzenesulfonamide in 800 ml of dry tetrahydrofuran under a nitrogen atmosphere was added dropwise 262 ml of a 1.6M solution of n-butyl lithium in hexane. The mixture was stirred for 2 hours at 20° C. during which time a precipitate formed. The suspension was cooled to 0° C. and 6.4 g of elemental sulfur was added in one portion. The mixture was warmed to 20° C. and stirred for one hour, then cooled at 0° C. while 20.5 ml of methallyl chloride was added slowly. The mixture was stirred at 20° C. for 16 hours, then 100 ml of 10% hydrochloric acid was added. After stirring several minutes, the organic layer was separated, washed with water and brine, dried over magnesium sulfate and concentrated in vacuo. The residue was slurried in 20% ether in hexane for several minutes and filtered to yield 47 g of the title compound; m.p. 104°–107° C.

NMR (CDCl$_3$)δ: 8.2–7.2 (m, 4H, Ar); 5.6 (broad, 1H, NH); 4.9 (broad, 2H, vinyl); 3.7 (s, 2H, CH$_2$); 1.9 (m, 3H, CH$_3$); and 1.2 (s, 9H, t-butyl).

EXAMPLE 13

N-t-Butyl-2,3-dihydro-2,2-dimethyl-7-benzo[b]thiophenesulfonamide

A solution of 37 g of N-t-butyl-2-(2-methyl-2-propenylthio)benzenesulfonamide (Example 12) in 40 ml of quinoline was heated at 220° C. for one hour, then cooled to 25° C. and diluted with ether. The ether suspension was washed well with 10% hydrochloric acid followed by water and brine, then dried over magnesium sulfate and concentrated in vacuo. The oily residue was chromatographed on 300 g of silica gel, packed and eluted with 20% ether in hexane, to give a major band which was concentrated in vacuo to yield a solid. The solid was slurried in 20% ether in hexane and filtered to yield 14.2 g of the title compound; m.p. 103°–105° C.

NMR (CDCl$_3$)δ: 7.9–7.0 (m, 3H, Ar); 5.0 (broad, 1H, NH); 3.15 (s, 2H, CH$_2$); 1.6 (m, 6H, CH$_3$); and 1.2 (s, 9H, t-butyl). IR (nujol): 3200 cm$^{-1}$ (NH).

EXAMPLE 14

2,3-Dihydro-2,2-dimethyl-7-benzo[b]thiophenesulfonamide

A solution of 17.2 g of N-t-butyl-2,3-dihydro-2,2-dimethyl-7-benzo[b]thiophenesulfonamide (Example 13) in 100 ml of trifluoroacetic acid was stirred at 20° C. for 16 hours. The solution was concentrated in vacuo, 100 ml of fresh trifluoroacetic acid was added and the mixture stirred at 20° C. for four more hours. After concentrating the solution in vacuo, the residue was dissolved in methylene chloride and the solution was washed with saturated aqueous sodium bicarbonate followed by brine, then dried over magnesium sulfate and concentrated in vacuo. The solid residue was slurried in 50% ether in hexane for several minutes then filtered to yield 8.4 g of the title compound; m.p. 102°-104° C.

NMR (CDCl$_3$)δ: 8.9-7.0 (m, 3H, Ar); 5.1 (broad, 2H, NH$_2$); 3.2 (s, 2H, CH$_2$); and 1.6 (s, 6H, CH$_3$). IR (nujol): 3300 cm$^{-1}$ (NH).

EXAMPLE 15

2,3-Dihydro-2,2-dimethyl-7-benzo[b]thiophenesulfonylisocyanate

To a refluxing solution of 8.6 g of 2,3-dihydro-2,2-dimethyl-7-benzo[b]thiophenesulfonamide (Example 14), 4.0 ml of n-butylisocyanate and 0.1 g of DABCO in 100 ml of xylenes was added 3.0 ml of phosgene at such a rate that the reaction temperature did not drop below 135° C. The mixture was refluxed for 1.5 hours, then the excess phosgene was purged with a stream of dry nitrogen. The mixture was cooled, filtered and concentrated in vacuo to yield the title compound as an oil. The crude yield was assumed to be near quantitative. IR (neat) 2220 cm$^{-1}$ (NCO).

The oil was diluted to a volume of 88 ml with dry acetonitrile for use as a stock solution in subsequent reactions.

EXAMPLE 16

N-[(4,6-Dimethoxypyrimidin-2-yl)aminocarbonyl]-2,3-dihydro-2,2-dimethyl-7-benzo[b]thiophenesulfonamide To 22 ml of the sulfonylisocyanate stock solution prepared in the previous Example (15) was added 0.78 g of 2-amino-4,6-dimethoxypyrimidine in one portion. The mixture was heated to reflux and stirred for 16 hours at 20° C. during which time a precipitate formed. The suspension was filtered and the solid washed with ether to yield 1.4 g of the title compound; m.p. 190°-192° C.

NMR (CDCl$_3$)δ: 12.7 (broad, 1H, NH); 8.0-7.0 (m, 4H, Ar+NH); 5.8 (s, 1H, CH); 4.0 (s, 6H, OCH$_3$); 3.15 (s, 2H, CH$_2$); and 1.5 (s, 6H, CH$_3$). IR (nujol): 1700 cm$^{-1}$ (c=o).

EXAMPLE 17

7-Nitrobenzo[b]thiophene 1,1-dioxide

To a solution of 24.8 g of 7-nitrobenzo[b]thiophene in 200 ml of glacial acetic acid pre-heated to 100° C. was added 90 ml of a 30% aqueous solution of hydrogen peroxide at such a rate that the temperature remained between 100° to 105° C. The solution was refluxed for one hour, then 200 ml of water was added and the mixture was cooled in an ice-bath and filtered. The solid residue was washed sequentially with water, ethanol and ether to yield 20 g of the title compound; m.p. 195°-197° C.

NMR (CDCl$_3$+DMSO)δ: 8.5 (m, 1H, Ar); 8.0 (m, 2H, Ar); 7.6 (m, 1H, Ar); and 7.2 (m, 1H, Ar). IR (nujol): 1540 and 1300 cm$^{-1}$.

EXAMPLE 18

7-Amino-2,3-dihydrobenzo[b]thiophene 1,1-dioxide

7-Nitrobenzo[b]thiophene-1,1-dioxide (19 g, Example 17) was hydrogenated in 200 ml of ethyl acetate over 1.0 g of 10% palladium-on-charcoal catalyst at 500 pounds-per-square-inch of pressure and 100° C. until no more hydrogen gas was absorbed. The mixture was filtered through celite, and the filtrate was concentrated in vacuo. The solid residue was recrystallized from 1-chlorobutane to yield 13.2 g of the title compound; m.p. 117°-119° C.

NMR (CDCl$_3$+DMSO)δ: 7.3-6.7 (m, 3H, Ar); 5.1 (broad, 2H, NH$_2$); and 3.4 (m, 4H, CH$_2$). IR (nujol): 3400, 3300, 1630 and 1590 cm$^{-1}$.

EXAMPLE 19

2,3-Dihydro-7-benzo[b]thiophenesulfonamide 1,1-dioxide

A. A diazonium salt was prepared by adding a solution of 5.3 g of sodium nitrite in 10 ml of water to a suspension containing 12.8 g of 7-amino-2,3-dihydrobenzo[b]thiophene-1,1-dioxide (Example 18), 25 ml of glacial acetic acid and 75 ml of concentrated hydrochloric acid, cooled at −5° to 5° C. during the addition. After stirring for 0.5 hour at 0° C., the diazonium salt suspension was added dropwise to a mixture consisting of 75 ml of concentrated hydrochloric acid, 50 ml of glacial acetic acid, 1.0 g of cupric chloride dihydrate and 8.0 ml of liquified sulfur dioxide, cooled at −5° C. during the addition. The mixture was stirred at 0° C. for one hour and at 20° C. for two hours, then diluted with excess water and stirred to yield a precipitate. The mixture was filtered and the solid residue was washed with water to yield crude 2,3-dihydro-7-benzo[b]thiophenesulfonyl chloride-1,1-dioxide.

B. The above sulfonyl chloride was dissolved in methylene chloride and dried over magnesium sulfate. The dried solution was contacted with 5.0 ml of liquified ammonia at −70° C., then stirred at 20° C. for 18 hours. The suspension was concentrated in vacuo, and the residue was slurried in 100 ml of 10% hydrochloric acid, then filtered. The solid residue was washed with water and ether to yield 11.5 g of the title compound; m.p. 215°-217° C.

NMR (CDCl$_3$+DMSO)δ: 8.1-7.6 (m, 3H, Ar); 7.0 (broad, 2H, NH$_2$); and 3.8-3.3 (m, 4H, CH$_2$). IR (nujol): 3300, 3200 and 1350 cm$^{-1}$.

EXAMPLE 20

N-[(4-Methoxy-6-methylpyrimidin-2-yl)aminocarbonyl]-2,3-dihydro-7-benzo[b]thiophene 1,1-dioxide A slurry of 1.0 g of 2,3-dihydro-7-benzo[b]thiophenesulfonamide 1,1-dioxide (Example 19) in 20 ml of dry methylene chloride was treated with 2.5 ml of a 20% solution of trimethylaluminum in toluene (Aldrich Chemicals) under a blanket of dry nitrogen. After stirring at 20° C. for 0.25 hour, 1.0 g of methyl (4-methoxy-6-methylpyrimidin-2-yl)carbamate (Example 6) was added in one portion and the resulting solution was stirred at 20° C. for 60 hours followed by refluxing for 24 hours. The mixture was cooled in an ice-bath, then treated with 10 ml of 10% hydrochloric acid and filtered. The solid residue was heated in tetrahydrofuran and filtered hot to yield 0.45 g of the title compound; m.p. 227°-229° C.

NMR (CDCl$_3$+DMSO)δ: 13.7 (broad, 1H, NH); 10.1 (broad, 1H, NH); 8.2-7.7 (m, 3H, Ar); 6.3 (s, 1H, CH); 4.0 (s, 3H, OCH$_3$); 3.5 (m, 4H, CH$_2$); and 2.4 (s, 3H, CH$_3$). IR (nujol): 3200 (NH), 1710 (c=o) cm$^{-1}$.

Using the techniques described in Equations 1–28 and Examples 4 and 15, or simple modifications thereof, the following compounds in Tables I and Ia can be made by one skilled in the art.

TABLE I

![Structure with R2, R1, R3, Q, R4, R5 on benzene ring with SO2NCO]

| R1 | R2 | R3 | R4 | R5 | Q | IR (cm⁻¹) |
|---|---|---|---|---|---|---|
| H | H | H | H | H | O | |
| CH₃ | H | H | H | H | O | 2200 |
| CH₃ | CH₃ | H | H | H | O | 2200 |
| C₂H₅ | H | H | H | H | O | |
| CH₃ | H | CH₃ | H | H | O | 2240 |
| C₂H₅ | H | CH₃ | H | H | O | |
| H | H | H | H | H | S | |
| CH₃ | H | H | H | H | S | |
| CH₃ | CH₃ | H | H | H | S | 2220 |
| C₂H₅ | H | H | H | H | S | |
| CH₃ | H | CH₃ | H | H | S | |
| H | H | H | H | H | SO₂ | |
| CH₃ | H | H | H | H | SO₂ | |
| CH₃ | CH₃ | H | H | H | SO₂ | |
| H | C₂H₅ | H | H | H | SO₂ | |
| CH₃ | H | CH₃ | H | H | SO₂ | |
| n-C₃H₇ | H | H | H | H | O | |
| CH₃ | H | H | Cl | H | O | 2220 |
| CH₃ | H | H | Br | H | O | |
| CH₃ | H | H | F | H | O | |
| CH₃ | H | H | CH₃ | H | O | 2220 |
| CH₃ | H | H | H | OCH₃ | O | |
| CH₃ | H | H | H | CH₃ | O | |
| CH₃ | H | H | H | OSO₂CH₃ | O | |
| CH₃ | H | H | H | OSO₂C₂H₅ | O | |
| CH₃ | H | H | Cl | H | SO₂ | |
| CH₃ | H | H | Br | H | SO₂ | |
| CH₃ | H | H | F | H | SO₂ | |
| CH₃ | H | H | CH₃ | H | SO₂ | |
| CH₃ | H | CH₃ | Cl | H | O | |

TABLE I-continued

| R1 | R2 | R3 | R4 | R5 | Q | IR (cm⁻¹) |
|---|---|---|---|---|---|---|
| n-butyl | H | H | H | H | O | |
| H | n-C₃H₇ | H | H | H | SO₂ | |
| H | n-butyl | H | H | H | SO₂ | |

TABLE Ia

![Structure with R6, R'6, Q1 on vinyl group attached to benzene ring with SO2NCO]

| R6 | R'6 | Q1 | IR (cm⁻¹) |
|---|---|---|---|
| H | H | O | |
| CH₃ | H | O | |
| CH₃ | CH₃ | O | |
| H | H | S | |
| CH₃ | H | S | |
| CH₃ | H | SO₂ | |

Using the techniques described in Equations 1–28 and Examples 5, 11, 16 and 20, or simple modifications thereof, the following compounds in Tables II–Vd can be made by one skilled in the art.

TABLE II

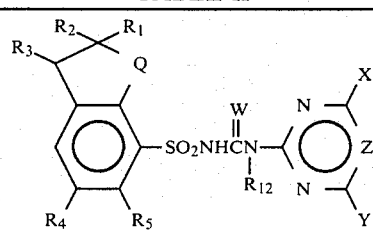

| R1 | R2 | R3 | R4 | R5 | R12 | W | Q | X | Y | Z | m.p. (°C.) |
|---|---|---|---|---|---|---|---|---|---|---|---|
| CH₃ | H | H | H | H | H | O | O | OCH₃ | OCH₃ | CH | 182–186° |
| CH₃ | H | H | H | H | H | O | O | OCH₃ | CH₃ | CH | 195–198° |
| CH₃ | H | H | H | H | H | O | O | CH₃ | CH₃ | CH | 178–182° |
| CH₃ | H | H | H | H | H | O | O | OCH₃ | OCH₃ | N | 164–167° |
| CH₃ | H | H | H | H | H | O | O | OCH₃ | CH₃ | N | 155–159° |
| CH₃ | H | H | H | H | H | O | O | CH₃ | CH₃ | N | 176–182° |
| CH₃ | H | H | H | H | H | O | O | Cl | OCH₃ | CH | 199–202° |
| CH₃ | CH₃ | H | H | H | H | O | O | OCH₃ | OCH₃ | CH | 198–200° |
| CH₃ | CH₃ | H | H | H | H | O | O | OCH₃ | CH₃ | CH | 170–172° |
| CH₃ | CH₃ | H | H | H | H | O | O | CH₃ | CH₃ | CH | 203–206° |
| CH₃ | CH₃ | H | H | H | H | O | O | OCH₃ | OCH₃ | N | 164–168° |
| CH₃ | CH₃ | H | H | H | H | O | O | OCH₃ | CH₃ | N | 162–165° |
| CH₃ | CH₃ | H | H | H | H | O | O | CH₃ | CH₃ | N | 172–176° |
| CH₃ | CH₃ | H | H | H | H | O | O | Cl | OCH₃ | CH | 164–168° |
| C₂H₅ | H | H | H | H | H | O | O | OCH₃ | OCH₃ | CH | |
| C₂H₅ | H | H | H | H | H | O | O | OCH₃ | CH₃ | CH | |
| C₂H₅ | H | H | H | H | H | O | O | CH₃ | CH₃ | CH | |
| C₂H₅ | H | H | H | H | H | O | O | OCH₃ | OCH₃ | N | |
| C₂H₅ | H | H | H | H | H | O | O | OCH₃ | CH₃ | N | |
| C₂H₅ | H | H | H | H | H | O | O | CH₃ | CH₃ | N | |
| C₂H₅ | H | H | H | H | H | O | O | Cl | OCH₃ | CH | |
| H | H | H | H | H | H | O | O | OCH₃ | OCH₃ | CH | |
| H | H | H | H | H | H | O | O | CH₃ | OCH₃ | CH | |

TABLE II-continued

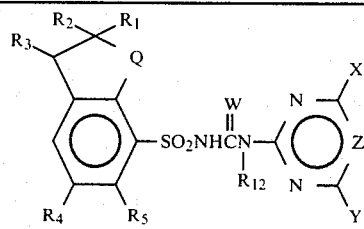

| R₁ | R₂ | R₃ | R₄ | R₅ | R₁₂ | W | Q | X | Y | Z | m.p. (°C.) |
|---|---|---|---|---|---|---|---|---|---|---|---|
| H | H | H | H | H | H | O | O | CH₃ | CH₃ | CH | |
| H | H | H | H | H | H | O | O | OCH₃ | OCH₃ | N | |
| H | H | H | H | H | H | O | O | OCH₃ | CH₃ | N | |
| H | H | H | H | H | H | O | O | CH₃ | CH₃ | N | |
| H | H | H | H | H | H | O | O | Cl | OCH₃ | CH | |
| CH₃ | H | CH₃ | H | H | H | O | O | OCH₃ | OCH₃ | CH | 162–165° |
| CH₃ | H | CH₃ | H | H | H | O | O | OCH₃ | CH₃ | CH | 166–170° |
| CH₃ | H | CH₃ | H | H | H | O | O | CH₃ | CH₃ | CH | 175–179° |
| CH₃ | H | CH₃ | H | H | H | O | O | OCH₃ | OCH₃ | N | 141–143° |
| CH₃ | H | CH₃ | H | H | H | O | O | OCH₃ | CH₃ | N | |
| CH₃ | H | CH₃ | H | H | H | O | O | CH₃ | CH₃ | N | 154–156° |
| CH₃ | H | CH₃ | H | H | H | O | O | Cl | OCH₃ | CH | 165–167° |
| n-C₃H₇ | H | H | H | H | H | O | O | OCH₃ | OCH₃ | CH | |
| n-C₃H₇ | H | H | H | H | H | O | O | OCH₃ | CH₃ | CH | |
| n-C₃H₇ | H | H | H | H | H | O | O | CH₃ | CH₃ | CH | |
| n-C₃H₇ | H | H | H | H | H | O | O | OCH₃ | OCH₃ | N | |
| n-C₃H₇ | H | H | H | H | H | O | O | OCH₃ | CH₃ | N | |
| n-C₃H₇ | H | H | H | H | H | O | O | Cl | OCH₃ | CH | |
| CH₃ | H | H | H | H | CH₃ | O | O | OCH₃ | OCH₃ | N | |
| CH₃ | H | H | H | H | CH₃ | O | O | OCH₃ | OCH₃ | CH | 166–167° |
| CH₃ | CH₃ | H | H | H | CH₃ | O | O | OCH₃ | OCH₃ | N | 151–152° |
| CH₃ | H | H | H | H | H | O | S | OCH₃ | OCH₃ | CH | 177–179° |
| CH₃ | H | H | H | H | H | O | S | OCH₃ | CH₃ | CH | 220–223° |
| CH₃ | H | H | H | H | H | O | S | CH₃ | CH₃ | CH | |
| CH₃ | H | H | H | H | H | O | S | OCH₃ | OCH₃ | N | 167–169° |
| CH₃ | H | H | H | H | H | O | S | OCH₃ | CH₃ | N | 145–147° |
| CH₃ | H | H | H | H | H | O | S | CH₃ | CH₃ | N | |
| CH₃ | H | H | H | H | H | O | S | Cl | OCH₃ | CH | |
| CH₃ | CH₃ | H | H | H | H | O | S | OCH₃ | OCH₃ | CH | 190–192° |
| CH₃ | CH₃ | H | H | H | H | O | S | OCH₃ | CH₃ | CH | 210–212° |
| CH₃ | CH₃ | H | H | H | H | O | S | CH₃ | CH₃ | CH | |
| CH₃ | CH₃ | H | H | H | H | O | S | OCH₃ | OCH₃ | N | 146–149° |
| CH₃ | CH₃ | H | H | H | H | O | S | OCH₃ | CH₃ | N | 183–185° |
| CH₃ | CH₃ | H | H | H | H | O | S | Cl | OCH₃ | CH | |
| C₂H₅ | H | H | H | H | H | O | S | OCH₃ | OCH₃ | CH | |
| C₂H₅ | H | H | H | H | H | O | S | OCH₃ | CH₃ | CH | |
| C₂H₅ | H | H | H | H | H | O | S | CH₃ | CH₃ | CH | |
| C₂H₅ | H | H | H | H | H | O | S | OCH₃ | OCH₃ | N | |
| C₂H₅ | H | H | H | H | H | O | S | OCH₃ | CH₃ | N | |
| C₂H₅ | H | H | H | H | H | O | S | Cl | OCH₃ | CH | |
| n-C₃H₇ | H | H | H | H | H | O | S | OCH₃ | OCH₃ | CH | |
| n-C₃H₇ | H | H | H | H | H | O | S | OCH₃ | CH₃ | N | |
| CH₃ | H | CH₃ | H | H | H | O | S | OCH₃ | OCH₃ | CH | |
| CH₃ | H | CH₃ | H | H | H | O | S | OCH₃ | CH₃ | CH | |
| H | H | H | H | H | H | O | S | OCH₃ | OCH₃ | CH | |
| H | H | H | H | H | H | O | S | OCH₃ | CH₃ | CH | |
| H | H | H | H | H | H | O | S | CH₃ | CH₃ | CH | |
| H | H | H | H | H | H | O | S | OCH₃ | OCH₃ | N | |
| H | H | H | H | H | H | O | S | OCH₃ | CH₃ | N | |
| H | H | H | H | H | H | O | S | Cl | OCH₃ | CH | |
| CH₃ | H | H | H | H | CH₃ | O | S | OCH₃ | OCH₃ | N | |
| CH₃ | H | H | H | H | CH₃ | O | S | OCH₃ | OCH₃ | CH | |
| CH₃ | CH₃ | H | H | H | CH₃ | O | S | OCH₃ | OCH₃ | N | |
| CH₃ | H | H | H | H | H | O | SO₂ | OCH₃ | OCH₃ | CH | 234–236° |
| CH₃ | H | H | H | H | H | O | SO₂ | OCH₃ | CH₃ | CH | 238–240° |
| CH₃ | H | H | H | H | H | O | SO₂ | CH₃ | CH₃ | CH | 214–216° |
| CH₃ | H | H | H | H | H | O | SO₂ | OCH₃ | OCH₃ | N | 160–170° |
| CH₃ | H | H | H | H | H | O | SO₂ | OCH₃ | CH₃ | N | 214–216° |
| CH₃ | H | H | H | H | H | O | SO₂ | CH₃ | CH₃ | N | |
| CH₃ | H | H | H | H | H | O | SO₂ | Cl | OCH₃ | CH | 223–226° |
| CH₃ | CH₃ | H | H | H | H | O | SO₂ | OCH₃ | OCH₃ | CH | 236–238° |
| CH₃ | CH₃ | H | H | H | H | O | SO₂ | OCH₃ | CH₃ | CH | 228–229° |
| CH₃ | CH₃ | H | H | H | H | O | SO₂ | CH₃ | CH₃ | CH | 228–230° |
| CH₃ | CH₃ | H | H | H | H | O | SO₂ | OCH₃ | OCH₃ | N | 214–216° |
| CH₃ | CH₃ | H | H | H | H | O | SO₂ | OCH₃ | CH₃ | N | 205–207° |
| CH₃ | CH₃ | H | H | H | H | O | SO₂ | CH₃ | CH₃ | N | 208–211° |
| CH₃ | CH₃ | H | H | H | H | O | SO₂ | Cl | OCH₃ | CH | 226–228° |
| C₂H₅ | H | H | H | H | H | O | SO₂ | OCH₃ | OCH₃ | CH | 221–223° |
| C₂H₅ | H | H | H | H | H | O | SO₂ | OCH₃ | CH₃ | CH | 215–217° |

TABLE II-continued

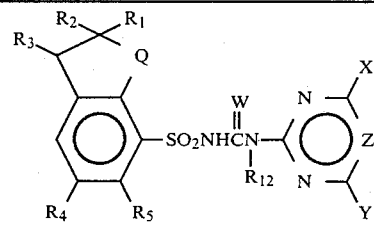

| R₁ | R₂ | R₃ | R₄ | R₅ | R₁₂ | W | Q | X | Y | Z | m.p. (°C.) |
|---|---|---|---|---|---|---|---|---|---|---|---|
| $C_2H_5$ | H | H | H | H | H | O | $SO_2$ | $CH_3$ | $CH_3$ | CH | |
| $C_2H_5$ | H | H | H | H | H | O | $SO_2$ | $OCH_3$ | $OCH_3$ | N | |
| $C_2H_5$ | H | H | H | H | H | O | $SO_2$ | $OCH_3$ | $CH_3$ | N | |
| $C_2H_5$ | H | H | H | H | H | O | $SO_2$ | Cl | $OCH_3$ | $CH_3$ | |
| $n\text{-}C_3H_7$ | H | H | H | H | H | O | $SO_2$ | $OCH_3$ | $OCH_3$ | CH | |
| $n\text{-}C_3H_7$ | H | H | H | H | H | O | $SO_2$ | $OCH_3$ | $CH_3$ | N | |
| H | H | H | H | H | H | O | $SO_2$ | $OCH_3$ | $OCH_3$ | CH | 247–249° |
| H | H | H | H | H | H | O | $SO_2$ | $CH_3$ | $OCH_3$ | CH | 227–229° |
| H | H | H | H | H | H | O | $SO_2$ | $CH_3$ | $CH_3$ | CH | 230–232° |
| H | H | H | H | H | H | O | $SO_2$ | $OCH_3$ | $OCH_3$ | N | 208–210° |
| H | H | H | H | H | H | O | $SO_2$ | $OCH_3$ | $CH_3$ | N | 210–213° |
| H | H | H | H | H | H | O | $SO_2$ | Cl | $OCH_3$ | CH | |
| H | H | $CH_3$ | H | H | H | O | $SO_2$ | $OCH_3$ | $OCH_3$ | CH | 232–235° |
| H | H | $CH_3$ | H | H | H | O | $SO_2$ | $OCH_3$ | $CH_3$ | CH | 221–223° |
| H | H | $CH_3$ | H | H | H | O | $SO_2$ | $CH_3$ | $CH_3$ | CH | 199–203° |
| H | H | $CH_3$ | H | H | H | O | $SO_2$ | $OCH_3$ | $OCH_3$ | N | 200–204° |
| H | H | $CH_3$ | H | H | H | O | $SO_2$ | $OCH_3$ | $CH_3$ | N | 211–213° |
| $CH_3$ | H | $CH_3$ | H | H | H | O | $SO_2$ | $OCH_3$ | $OCH_3$ | CH | |
| $CH_3$ | H | $CH_3$ | H | H | H | O | $SO_2$ | $OCH_3$ | $CH_3$ | CH | |
| $CH_3$ | H | $CH_3$ | H | H | H | O | $SO_2$ | $CH_3$ | $CH_3$ | CH | |
| $CH_3$ | H | $CH_3$ | H | H | H | O | $SO_2$ | $OCH_3$ | $CH_3$ | N | |
| $CH_3$ | H | H | H | H | $CH_3$ | O | $SO_2$ | $OCH_3$ | $OCH_3$ | CH | 208–211° |
| $CH_3$ | H | H | H | H | $CH_3$ | O | $SO_2$ | $OCH_3$ | $OCH_3$ | N | 160–163° |
| $CH_3$ | $CH_3$ | H | H | H | $CH_3$ | O | $SO_2$ | $OCH_3$ | $OCH_3$ | N | 182–184° |
| $CH_3$ | H | H | H | H | H | O | SO | $OCH_3$ | $OCH_3$ | CH | |
| $CH_3$ | H | H | H | H | H | O | SO | $OCH_3$ | $CH_3$ | N | |
| $CH_3$ | $CH_3$ | H | Br | H | H | O | O | $CH_3$ | $OCH_3$ | N | |
| $CH_3$ | H | H | Cl | H | H | O | O | $OCH_3$ | $OCH_3$ | CH | 225–226° |
| $CH_3$ | H | H | $CH_3$ | H | H | O | O | $OCH_3$ | $OCH_3$ | CH | 233–240° |
| $CH_3$ | H | H | $CF_3$ | H | H | O | O | $OCH_3$ | $OCH_3$ | CH | |
| $CH_3$ | H | H | $OCH_3$ | H | H | O | O | $OCH_3$ | $CH_3$ | CH | |
| $CH_3$ | H | H | $CH_3$ | H | H | O | S | $OCH_3$ | $OCH_3$ | CH | |
| $CH_3$ | H | H | $CH_3$ | H | H | O | $SO_2$ | $OCH_3$ | $OCH_3$ | CH | |
| $CH_3$ | H | H | H | H | H | S | O | $OCH_3$ | $OCH_3$ | CH | |
| $CH_3$ | $CH_3$ | H | H | H | H | S | O | $OCH_3$ | $CH_3$ | N | |
| $CH_3$ | H | H | H | H | H | S | S | $OCH_3$ | $OCH_3$ | CH | |
| $CH_3$ | H | H | H | H | H | S | S | $CH_3$ | $OCH_3$ | N | |
| $CH_3$ | H | H | H | H | H | S | $SO_2$ | $CH_3$ | $CH_3$ | N | |
| $CH_3$ | H | H | H | H | H | S | $SO_2$ | $OCH_3$ | $OCH_3$ | CH | |
| $CH_3$ | H | H | H | $CH_3$ | H | O | $SO_2$ | $OCH_3$ | $OCH_3$ | CH | |
| $CH_3$ | H | H | H | $OCH_3$ | H | O | O | $OCH_3$ | $OCH_3$ | CH | |
| $CH_3$ | $CH_3$ | H | H | Cl | H | O | S | $OCH_3$ | $CH_3$ | CH | |
| $CH_3$ | H | H | H | Br | H | O | O | $OCH_3$ | $CH_3$ | N | |
| $CH_3$ | H | H | H | $NO_2$ | H | O | O | $OCH_3$ | $OCH_3$ | CH | |
| $CH_3$ | H | H | H | $CO_2CH_3$ | H | O | O | $CH_3$ | $OCH_3$ | N | |
| $CH_3$ | H | H | H | $CO_2C_2H_5$ | H | O | $SO_2$ | $OCH_3$ | $OCH_3$ | CH | |
| $CH_3$ | H | H | H | $CO_2CH_2CH_2CH_3$ | H | O | O | $OCH_3$ | $OCH_3$ | CH | |
| $CH_3$ | $CH_3$ | H | H | $CO_2CH(CH_3)_2$ | H | O | S | $OCH_3$ | $OCH_3$ | CH | |
| $CH_3$ | H | H | H | $CO_2CH_2CH=CH_2$ | H | O | O | $OCH_3$ | $OCH_3$ | CH | |
| $CH_3$ | H | H | H | $CO_2CH_2CH_2OCH_3$ | H | O | O | $OCH_3$ | $OCH_3$ | CH | |
| $CH_3$ | H | H | H | $CO_2CH_2CH_2Cl$ | H | O | O | $OCH_3$ | $OCH_3$ | CH | |
| $CH_3$ | $CH_3$ | H | H | $SO_2CH_3$ | H | O | O | $CH_3$ | $OCH_3$ | N | |
| $CH_3$ | $CH_3$ | H | H | $SO_2C_2H_5$ | H | O | O | $OCH_3$ | $CH_3$ | CH | |
| $CH_3$ | H | H | H | $SO_2CH_2CH_2CH_3$ | H | O | O | $OCH_3$ | $OCH_3$ | CH | |
| $CH_3$ | H | H | H | $SO_2CH(CH_3)_2$ | H | O | O | $OCH_3$ | $OCH_3$ | CH | |
| $CH_3$ | H | H | H | H | H | O | O | Cl | $N(CH_3)_2$ | CH | |
| $CH_3$ | H | H | H | $OSO_2CH_3$ | H | O | $SO_2$ | $OCH_3$ | $CH_3$ | CH | |
| $CH_3$ | H | H | H | $OSO_2C_2H_5$ | H | O | O | $OCH_3$ | $OCH_3$ | CH | |
| $CH_3$ | H | H | H | $OSO_2CH_2CH_2CH_3$ | H | O | O | $OCH_3$ | $OCH_3$ | CH | |
| $CH_3$ | H | H | H | $OSO_2CH(CH_3)_2$ | H | O | S | $CH_3$ | $OCH_3$ | CH | |
| $CH_3$ | $CH_3$ | H | H | $OSO_2CF_3$ | H | O | O | $CH_3$ | $OCH_3$ | N | |
| $CH_3$ | H | H | H | $SO_2N(CH_3)_2$ | H | O | O | $CH_3$ | $CH_3$ | CH | |
| $CH_3$ | H | H | H | $SO_2N(CH_3)C_2H_5$ | H | O | O | $OCH_3$ | $OCH_3$ | CH | |
| $CH_3$ | H | H | H | H | H | O | O | $CH_3$ | $CH_3$ | CCl |
| $CH_3$ | H | H | H | H | H | O | S | H | $CH_3$ | CCl |
| $CH_3$ | H | H | H | H | H | O | O | H | $CH_3$ | CBr |
| $CH_3$ | $CH_3$ | H | H | H | H | O | S | H | $OCH_3$ | CCl |
| $CH_3$ | $CH_3$ | H | H | H | H | O | O | H | $OCH_3$ | CBr |
| $CH_3$ | $CH_3$ | H | H | H | H | O | $SO_2$ | $CH_3$ | $CH_3$ | CBr |

TABLE II-continued

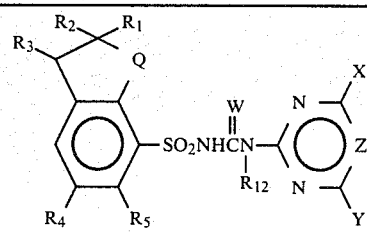

| R1 | R2 | R3 | R4 | R5 | R12 | W | Q | X | Y | Z | m.p. (°C.) |
|---|---|---|---|---|---|---|---|---|---|---|---|
| CH3 | H | H | H | H | H | O | O | H | CH3 | CCH3 | |
| CH3 | H | H | H | H | H | O | O | OCH3 | CH3 | CC2H5 | |
| CH3 | CH3 | H | H | H | H | O | S | OCH3 | OC2H5 | N | |
| CH3 | H | H | H | H | H | O | O | OCH3 | OC2H5 | CH | |
| CH3 | H | H | H | H | H | O | SO2 | OCH3 | CH2OCH3 | N | |
| CH3 | H | H | H | H | H | O | O | OCH3 | CH2OCH3 | CH | 146–149° |
| CH3 | CH3 | H | H | H | H | O | O | OCH3 | OCH2CF3 | N | |
| CH3 | CH3 | H | H | H | H | O | S | CH3 | OCH2CF3 | CH | |
| CH3 | H | H | H | H | H | O | O | OCH3 | N(CH3)2 | N | |
| CH3 | H | H | H | H | H | O | O | OCH3 | N(CH3)2 | CH | |
| CH3 | H | H | H | H | H | O | O | OCH3 | NHCH3 | N | |
| CH3 | H | H | H | H | H | O | O | CH3 | C2H5 | CH | |
| CH3 | H | H | H | H | H | O | O | CH3 | OC2H5 | CH | 166–167° |
| CH3 | H | H | H | H | H | O | SO2 | CH3 | OC2H5 | N | 178–180° |
| H | CH3 | H | H | H | H | O | O | CH3 | OCH2CF3 | N | 181–183° |
| CH3 | CH3 | H | H | H | H | O | O | CH3 | OCH2CH=CH2 | N | |
| CH3 | H | H | H | H | H | O | O | CH3 | OCH2C≡CH | N | |
| CH3 | H | H | H | H | H | O | O | Cl | NH2 | CH | |
| CH3 | H | H | H | H | H | O | O | Cl | NHCH3 | CH | |
| CH3 | CH3 | H | H | H | H | O | S | OCH3 | CH(OCH3)2 | CH | |
| CH3 | H | H | H | H | H | O | O | CH3 | CH(OCH3)2 | N | |
| CH3 | H | H | H | H | H | O | O | CH3 | CH(OCH3)2 | CH | 148–150° |
| CH3 | H | H | H | H | H | O | O | OCH3 | NH2 | CH | |
| CH3 | H | H | H | H | H | O | SO2 | CH3 | CF3 | CH | |
| CH3 | H | H | H | H | H | O | O | OCH3 | NHCH3 | CH | |
| CH3 | H | H | H | H | H | O | O | CH3 | ![1,3-dioxolan-2-yl] | CH | |
| CH3 | H | H | H | H | H | O | SO2 | OCH3 | CH(OCH3)2 | CH | 111–113° |
| CH(CH3)2 | H | H | H | H | H | O | O | OCH3 | OCH3 | CH | |
| H | H | CH3 | H | H | H | O | SO2 | CH3 | CH3 | N | 203–206° |
| H | H | H | H | H | H | O | SO2 | CH3 | CH3 | N | |
| CH3 | CH3 | H | H | H | H | O | S | CH3 | CH3 | N | |
| CH3 | H | H | H | H | H | O | O | OCH3 | CH(OCH3)2 | CH | |
| CH3 | H | H | H | H | H | O | O | OCH3 | ![1,3-dioxolan-2-yl] | CH | 171–174° |
| CH3 | CH3 | H | H | H | H | O | O | OCH3 | ![1,3-dioxolan-2-yl] | CH | 179–183° |
| CH3 | CH3 | H | H | H | H | O | O | CH3 | ![1,3-dioxolan-2-yl] | CH | |
| CH3 | H | H | H | H | H | O | O | OCH3 | SCH3 | N | |
| CH3 | CH3 | H | H | H | H | O | O | OCH3 | SCH3 | N | |
| CH3 | H | H | H | H | H | O | O | OCH3 | SCH3 | CH | |
| CH3 | H | H | H | H | H | O | SO2 | OCH3 | SCH3 | N | 180–183° |
| CH3 | CH3 | H | H | H | H | O | O | OCH3 | SCH3 | CH | |
| CH3 | H | H | H | H | H | O | O | CH3 | SCH3 | CH | |
| H | CH3 | H | H | H | CH3 | O | SO2 | CH3 | OCH3 | CH | 220–222° |
| H | CH3 | H | H | H | CH3 | O | SO2 | CH3 | OCH3 | N | 175–178° |
| CH3 | H | H | H | H | H | O | SO2 | CH3 | OCH2CF3 | N | 168–173° |
| CH3 | CH3 | H | H | H | CH3 | O | SO2 | CH3 | CH2OCH3 | N | 203–206° |
| CH3 | CH3 | H | H | H | H | O | SO2 | OCH3 | OCH3 | CH | 204–206° |
| CH3 | CH3 | H | H | H | H | O | SO2 | CH3 | CH2OCH3 | CH | 179–181° |
| CH3 | CH3 | H | H | H | H | O | SO2 | CH3 | OCH2CF3 | N | 158–160° |
| CH3 | CH3 | H | H | H | H | O | SO | OCH3 | OCH3 | CH | 189–191° |

TABLE II-continued

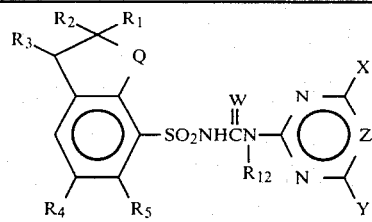

| R₁ | R₂ | R₃ | R₄ | R₅ | R₁₂ | W | Q | X | Y | Z | m.p. (°C.) |
|---|---|---|---|---|---|---|---|---|---|---|---|
| CH₃ | CH₃ | H | H | H | H | O | SO | CH₃ | OCH₃ | CH | 138–140° |
| CH₃ | CH₃ | H | H | H | H | O | SO | CH₃ | OCH₃ | N | 185–187° |
| CH₃ | CH₃ | H | H | H | H | O | SO | OCH₃ | OCH₃ | N | 190–192° |
| H | CH₃ | H | Cl | H | H | O | O | CH₃ | OCH₃ | CH | 209–211° |
| H | CH₃ | H | Cl | H | H | O | O | CH₃ | CH₃ | CH | 206–207° |
| H | CH₃ | H | Cl | H | H | O | O | OCH₃ | OCH₃ | N | 191–192° |
| H | CH₃ | H | Cl | H | H | O | O | CH₃ | OCH₃ | N | 199–200° |
| CH₃ | H | H | Cl | H | H | O | O | Cl | OCH₃ | CH | 201–203° |
| CH₃ | H | H | Cl | H | H | O | O | CH₃ | CH₃ | N | 199–201° |
| H | CH₃ | H | CH₃ | H | H | O | O | Cl | CH₃ | CH | 208–211° |
| CH₃ | H | H | CH₃ | H | H | O | O | CH₃ | OCH₃ | CH | 225–226° |
| CH₃ | H | H | CH₃ | H | H | O | O | CH₃ | CH₃ | CH | 212–214° |
| CH₃ | H | H | CH₃ | H | H | O | O | OCH₃ | OCH₃ | N | 206–240° |
| CH₃ | H | H | CH₃ | H | H | O | O | CH₃ | CH₃ | N | 208–211° |
| CH₃ | H | H | CH₃ | H | H | O | O | CH₃ | OCH₃ | N | 211–213° |
| CH₃ | H | H | H | H | H | O | O | CH₃ | CH₂OCH₃ | CH | 129–134° |
| CH₃ | H | H | H | H | CH₃ | O | O | CH₃ | OCH₃ | CH | 163–164° |
| CH₃ | H | H | H | H | CH₃ | O | O | CH₃ | OCH₃ | N | 180–182° |
| CH₃ | CH₃ | H | H | H | H | O | O | CH₃ | OC₂H₅ | CH | 173–177° |
| CH₃ | CH₃ | H | H | H | H | O | O | CH₃ | CH(OCH₃)₂ | CH | 145–149° |
| CH₃ | CH₃ | H | H | H | H | O | O | OCH₃ | OCH₃ | CH | 157–163° |
| CH₃ | CH₃ | H | H | H | CH₃ | O | O | CH₃ | OCH₃ | CH | 187–191° |
| CH₃ | CH₃ | H | H | H | CH₃ | O | O | CH₃ | OCH₃ | N | 175–178° |
| CH₃ | H | H | H | H | H | O | O | F | OCH₃ | CH | |
| H | CH₃ | H | H | H | H | O | SO₂ | F | OCH₃ | CH | |
| CH₃ | H | H | Cl | H | H | O | O | OCH₃ | CH(OC₂H₅)₂ | CH | |
| CH₃ | H | H | H | H | H | O | SO₂ | OCH₃ | CH(OC₂H₅)₂ | CH | |
| CH₃ | H | H | H | H | H | O | O | OCH₃ | C₂H₅ | CH | |
| CH₃ | H | H | H | H | H | O | SO₂ | OCH₃ | C₂H₅ | CH | |
| CH₃ | H | H | H | H | H | O | O | OCH₃ | 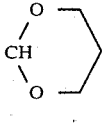 | CH | |
| CH₃ | H | H | H | H | H | O | SO₂ | OCH₃ | 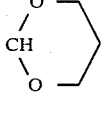 | CH | |
| CH₃ | H | H | H | H | H | O | O | OCH₃ | 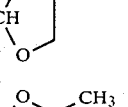 | CH | |
| CH₃ | H | H | H | H | H | O | SO₂ | OCH₃ | 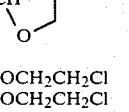 | CH | |
| CH₃ | H | H | H | H | H | O | SO₂ | OCH₃ | OCH₂CH₂Cl | CH | |
| CH₃ | H | H | H | H | H | O | O | OCH₃ | OCH₂CH₂Cl | N | |
| CH₃ | H | H | H | H | H | O | SO₂ | OCH₃ | OCH₂CH₂Br | CH | |
| CH₃ | H | H | H | H | H | O | O | OCH₃ | OCH₂CH₂Br | N | |
| CH₃ | H | H | H | H | H | O | SO₂ | OCH₃ | OCH₂CH₂F | CH | |
| CH₃ | H | H | H | H | H | O | O | OCH₃ | OCH₂CH₂F | N | |
| CH₃ | H | H | H | H | H | O | SO₂ | OCH₃ | CN | CH | |
| CH₃ | H | H | H | H | H | O | O | OCH₃ | CN | N | |
| CH₃ | H | H | H | H | H | O | SO₂ | OCH₃ | CH₂OCH₂CH₃ | CH | |
| CH₃ | CH₃ | H | H | H | H | O | SO₂ | OCH₃ | CH₂OCH₂CH₃ | CH | |
| CH₃ | H | H | H | H | H | O | SO₂ | OCH₃ | OCH₂CH₂OCH₃ | CH | |
| CH₃ | H | H | H | H | H | O | O | OCH₃ | OCH₂CH₂OCH₃ | CH | |
| CH₃ | CH₃ | H | H | H | H | O | SO₂ | CH₃ | OCF₂H | CH | 206–208° |
| CH₃ | H | H | H | H | H | O | SO₂ | CH₃ | OCF₂H | CH | |
| CH₃ | H | H | Cl | H | H | O | O | CH₃ | OCF₂H | CH | |
| CH₃ | H | H | H | H | H | O | O | CH₃ | OCF₂H | CH | |

TABLE II-continued

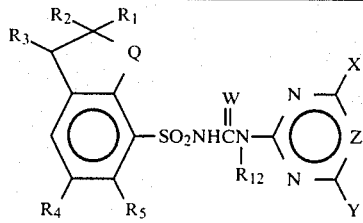

| R₁ | R₂ | R₃ | R₄ | R₅ | R₁₂ | W | Q | X | Y | Z | m.p. (°C.) |
|---|---|---|---|---|---|---|---|---|---|---|---|
| CH₃ | CH₃ | H | H | H | H | O | SO₂ | OCH₃ | OCF₂H | CH | 215–218° |
| CH₃ | H | H | H | H | H | O | SO₂ | OCH₃ | OCF₂H | CH | |
| CH₃ | H | H | Cl | H | H | O | O | OCH₃ | OCF₂H | CH | |
| CH₃ | H | H | H | H | H | O | O | OCH₃ | OCF₂H | CH | 197–200° |
| CH₃ | H | H | H | H | H | O | SO₂ | CH₃ | SCF₂H | CH | |
| CH₃ | CH₃ | H | H | H | H | O | SO₂ | CH₃ | SCF₂H | CH | |
| CH₃ | H | H | Cl | H | H | O | O | CH₃ | SCF₂H | CH | |
| CH₃ | CH₃ | H | H | H | H | O | SO₂ | OCH₃ | SCF₂H | CH | |
| CH₃ | H | H | H | H | H | O | SO₂ | OCH₃ | SCF₂H | CH | |
| H | CH₃ | H | H | H | H | O | O | SCF₂H | OCH₃ | CH | |
| H | CH₃ | H | Cl | H | H | O | O | SCF₂H | OCH₃ | CH | |
| CH₃ | H | H | H | H | H | O | SO₂ | CH₃ | OCF₂CHFCl | CH | |
| CH₃ | H | H | H | H | H | O | O | OCH₃ | OCF₂CHFCl | N | |
| CH₃ | H | H | H | H | H | O | SO₂ | CH₃ | OCF₂CHFBr | CH | |
| CH₃ | H | H | H | H | H | O | SO₂ | OCH₃ | OCH₂CHFBr | CH | |
| CH₃ | H | H | H | H | H | O | O | CH₃ | OCF₂CF₂H | CH | |
| CH₃ | H | H | H | H | H | O | SO₂ | OCH₃ | OCF₂CF₂H | CH | |
| CH₃ | H | H | H | H | H | O | O | CH₃ | OCF₂CHFCF₃ | CH | |
| CH₃ | H | H | H | H | H | O | SO₂ | OCH₃ | OCF₂CHFCF₃ | CH | |
| CH₃ | CH₃ | H | H | H | H | O | SO₂ | OCF₂H | OCF₂H | CH | |
| CH₃ | H | H | H | H | H | O | SO₂ | OCF₂H | OCF₂H | CH | |
| CH₃ | H | H | Cl | H | H | O | O | OCF₂H | OCF₂H | CH | |
| CH₃ | H | H | H | H | H | O | O | OCF₂H | OCF₂H | CH | |
| CH₃ | H | H | H | H | H | O | SO₂ | OCF₂H | SCF₂H | CH | |
| CH₃ | H | H | H | H | H | O | SO₂ | SCF₂H | SCF₂H | CH | |
| CH₃ | H | H | H | H | H | O | SO₂ | OCF₂H | CH(OCH₃)₂ | CH | |
| CH₃ | CH₃ | H | H | H | H | O | SO₂ | OCF₂H | CH(OCH₃)₂ | CH | |
| CH₃ | H | H | H | H | H | O | O | OCF₂H | CH(OCH₃)₂ | CH | |
| CH₃ | H | H | Cl | H | H | O | O | OCF₂H | CH(OCH₃)₂ | CH | |
| CH₃ | H | H | H | H | H | O | SO₂ | CH₃ | OCF₂H | N | |
| CH₃ | H | H | H | H | H | O | O | OCH₃ | OCF₂H | N | |
| CH₃ | H | H | H | H | H | O | SO₂ | CH₃ | SCF₂H | N | |
| CH₃ | H | H | H | H | H | O | O | OCH₃ | SCF₂H | N | |
| CH₃ | H | H | H | H | H | O | SO₂ | CH₃ | OCF₂CHFCl | N | |
| CH₃ | H | H | H | H | H | O | SO₂ | OCH₃ | OCF₂CHFCl | N | |
| CH₃ | H | H | H | H | H | O | SO₂ | CH₃ | OCF₂CHFBr | N | |
| CH₃ | H | H | H | H | H | O | SO₂ | OCH₃ | OCH₂CHFBr | N | |
| CH₃ | H | H | H | H | H | O | SO₂ | CH₃ | OCF₂CF₂H | N | |
| CH₃ | H | H | H | H | H | O | O | OCH₃ | OCF₂CF₂H | N | |
| CH₃ | H | H | H | H | H | O | SO₂ | CH₃ | OCF₂CHFCF₃ | N | |
| CH₃ | H | H | H | H | H | O | SO₂ | OCH₃ | OCF₂CHFCF₃ | N | |
| CH₃ | H | H | H | H | H | O | SO₂ | OCF₂H | OCF₂H | N | |
| CH₃ | H | H | H | H | H | O | SO₂ | OCH₃ | OCH₂CF₃ | N | |
| CH₃ | CH₃ | H | H | H | H | O | SO₂ | OCH₃ | OCH₂CF₃ | N | |
| CH₃ | H | H | H | H | H | O | SO₂ | CH₃ | OCH₂CF₃ | N | |
| CH₃ | CH₃ | H | H | H | H | O | SO₂ | CH₃ | OCH₂CF₃ | N | |
| CH₃ | H | H | H | H | H | O | O | OCH₃ | OCH₂CF₃ | N | |
| CH₃ | H | H | Cl | H | H | O | O | OCH₃ | OCH₂CF₃ | N | |
| CH₃ | H | H | Cl | H | H | O | O | CH₃ | OCH₂CF₃ | N | |
| CH₃ | H | H | CH₃ | H | H | O | O | OCH₃ | OCH₂CF₃ | N | |
| CH₃ | H | H | CH₃ | H | H | O | O | CH₃ | OCH₂CF₃ | N | |
| CH₃ | H | H | F | H | H | O | O | OCH₃ | OCH₃ | CH | |
| CH₃ | H | H | F | H | H | O | O | CH₃ | OCH₃ | CH | |
| CH₃ | H | H | F | H | H | O | O | OCH₃ | CH₃ | CH | |
| CH₃ | H | H | F | H | H | O | O | OCH₃ | CH₃ | N | |
| CH₃ | H | H | F | H | H | O | O | OCH₃ | OCH₃ | N | |
| CH₃ | H | H | F | H | H | O | O | Cl | OCH₃ | CH | |
| CH₃ | H | H | F | H | H | O | O | OCH₃ | CH₃ | N | |
| CH₃ | H | H | F | H | H | O | O | OCH₃ | OCH₂CF₃ | N | |
| CH₃ | H | H | F | H | H | O | O | OCH₃ | CH(OCH₃)₂ | CH | |
| CH₃ | H | H | F | H | H | O | O | OCH₃ | OCF₂H | CH | |
| CH₃ | H | H | F | H | H | O | SO₂ | OCH₃ | OCH₃ | CH | |
| CH₃ | H | H | SCH₃ | H | H | O | O | OCH₃ | OCH₃ | CH | |
| CH₃ | H | H | SCH₃ | H | H | O | SO₂ | OCH₃ | OCH₃ | CH | |
| CH₃ | H | H | OCF₂H | H | H | O | O | OCH₃ | OCH₃ | CH | |
| CH₃ | H | H | OCF₂H | H | H | O | SO₂ | OCH₃ | OCH₃ | CH | |
| CH₃ | H | H | H | F | H | O | O | OCH₃ | OCH₃ | CH | |
| CH₃ | H | H | H | CF₃ | H | O | O | OCH₃ | OCH₃ | CH | |
| H | CH₃ | H | H | SCH₃ | H | O | O | OCH₃ | OCH₃ | CH | |

TABLE II-continued

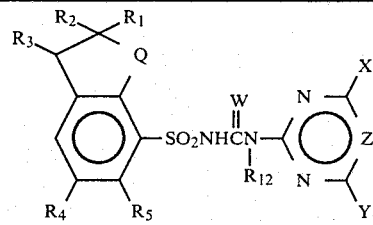

| R₁ | R₂ | R₃ | R₄ | R₅ | R₁₂ | W | Q | X | Y | Z | m.p. (°C.) |
|---|---|---|---|---|---|---|---|---|---|---|---|
| H | CH₃ | H | H | SO₂N(OCH₃)CH₃ | H | O | O | OCH₃ | OCH₃ | CH | |
| CH₃ | H | H | H | OCF₂H | H | O | O | OCH₃ | OCH₃ | CH | |
| CH₃ | H | H | H | OCF₂H | H | O | SO₂ | OCH₃ | OCH₃ | CH | |
| n-butyl | H | H | H | H | H | O | O | OCH₃ | OCH₃ | CH | |
| H | C₂H₅ | H | H | H | H | O | SO₂ | CH₃ | CH₃ | CH | |
| H | C₂H₅ | H | H | H | H | O | SO₂ | OCH₃ | CH₃ | N | |
| H | C₂H₅ | H | H | H | H | O | SO₂ | OCH₃ | OCH₃ | CH | |
| H | n-C₃H₇ | H | H | H | H | O | SO₂ | OCH₃ | OCH₃ | CH | |
| H | n-butyl | H | H | H | H | O | SO₂ | OCH₃ | OCH₃ | CH | |
| CH₃ | H | H | H | H | H | O | SO₂ | Cl | OCF₂H | CH | |
| CH₃ | CH₃ | H | H | H | H | O | SO₂ | Cl | OCF₂H | CH | |
| CH₃ | H | H | H | H | H | O | O | Cl | OCF₂H | CH | |
| CH₃ | H | H | Cl | H | H | O | O | Cl | OCF₂H | CH | |
| CH₃ | H | H | Cl | H | H | O | SO₂ | OCH₃ | OCH₃ | CH | |
| CH₃ | H | H | Cl | H | H | O | SO₂ | OCH₃ | CH₃ | CH | |
| CH₃ | H | H | Cl | H | H | O | SO₂ | CH₃ | CH₃ | CH | |
| CH₃ | H | H | Cl | H | H | O | SO₂ | OCH₃ | CH₃ | N | |
| CH₃ | H | H | Cl | H | H | O | SO₂ | OCH₃ | OCH₃ | N | |
| CH₃ | H | H | Cl | H | H | O | SO₂ | Cl | OCH₃ | CH | |
| CH₃ | H | H | CH₃ | H | H | O | SO₂ | OCH₃ | OCH₃ | CH | |
| CH₃ | H | H | CH₃ | H | H | O | SO₂ | OCH₃ | CH₃ | CH | |
| CH₃ | H | H | CH₃ | H | H | O | SO₂ | CH₃ | CH₃ | CH | |
| CH₃ | H | H | CH₃ | H | H | O | SO₂ | OCH₃ | CH₃ | N | |
| CH₃ | H | H | CH₃ | H | H | O | SO₂ | OCH₃ | OCH₃ | N | |
| CH₃ | H | H | CH₃ | H | H | O | SO₂ | Cl | OCH₃ | CH | |

TABLE IIa

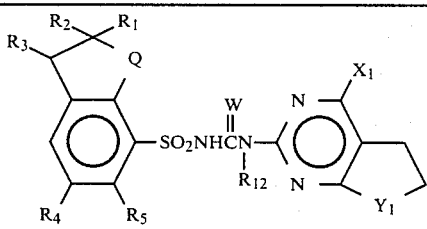

| R₁ | R₂ | R₃ | R₄ | R₅ | R₁₂ | W | Q | Y₁ | X₁ | m.p. (°C.) |
|---|---|---|---|---|---|---|---|---|---|---|
| CH₃ | CH₃ | H | H | H | H | O | O | O | CH₃ | 207–208° |
| CH₃ | CH₃ | H | H | H | H | O | O | O | OCH₃ | |
| CH₃ | CH₃ | H | H | H | H | O | O | O | OC₂H₅ | |
| CH₃ | H | H | H | H | H | O | O | O | CH₃ | 201–202° |
| CH₃ | H | H | H | H | H | O | O | O | OCH₃ | |
| C₂H₅ | H | H | H | H | H | O | O | O | CH₃ | |
| C₂H₅ | H | H | H | H | H | O | O | O | OCH₃ | |
| n-C₃H₇ | H | H | H | H | H | O | O | O | CH₃ | |
| n-C₃H₇ | H | H | H | H | H | O | O | O | OCH₃ | |
| H | H | H | H | H | H | O | O | O | CH₃ | |
| H | H | H | H | H | H | O | O | O | OCH₃ | |
| CH₃ | H | CH₃ | H | H | H | O | O | O | CH₃ | |
| CH₃ | H | CH₃ | H | H | H | O | O | O | OCH₃ | |
| CH₃ | H | H | H | H | H | O | O | CH₂ | OCH₃ | |
| CH₃ | H | H | H | H | H | O | O | CH₂ | CH₃ | |
| CH₃ | CH₃ | H | H | H | H | O | O | CH₃ | OC₂H₅ | |
| CH₃ | CH₃ | H | H | H | H | O | O | CH₂ | OCH₃ | |
| CH₃ | CH₃ | H | H | H | H | O | O | CH₂ | CH₃ | |
| CH₃ | H | H | H | H | CH₃ | O | O | O | OCH₃ | |
| CH₃ | H | H | H | H | H | O | S | O | CH₃ | |
| CH₃ | CH₃ | H | H | H | H | O | S | O | CH₃ | |
| CH₃ | H | H | H | H | H | O | S | CH₂ | CH₃ | |
| CH₃ | CH₃ | H | H | H | H | O | S | CH₂ | OCH₃ | |
| CH₃ | H | H | H | H | H | O | SO₂ | O | CH₃ | 208–210° |
| CH₃ | CH₃ | H | H | H | H | O | SO₂ | O | CH₃ | 198–201° |
| CH₃ | H | H | H | H | H | O | SO₂ | O | OCH₃ | |
| CH₃ | CH₃ | H | H | H | H | O | SO₂ | O | OCH₃ | |

TABLE IIa-continued

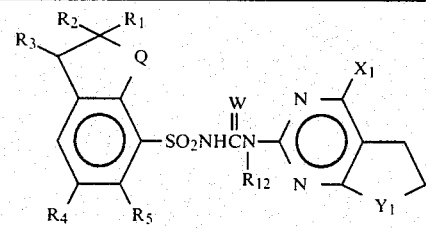

| R₁ | R₂ | R₃ | R₄ | R₅ | R₁₂ | W | Q | Y₁ | X₁ | m.p. (°C.) |
|---|---|---|---|---|---|---|---|---|---|---|
| CH₃ | H | H | H | H | H | O | S | O | OCH₃ | |
| CH₃ | CH₃ | H | H | H | H | O | S | O | OCH₃ | |
| CH₃ | H | H | H | H | H | O | SO₂ | CH₂ | CH₃ | |
| CH₃ | CH₃ | H | H | H | H | O | SO₂ | CH₂ | OCH₃ | |
| C₂H₅ | H | H | H | H | H | O | SO₂ | O | CH₃ | |
| CH₃ | CH₃ | H | H | H | H | S | O | O | CH₃ | |
| CH₃ | H | H | H | H | H | S | O | O | CH₃ | |
| CH₃ | CH₃ | H | H | H | H | S | SO₂ | O | CH₃ | |
| CH₃ | H | H | H | H | H | S | S | O | CH₃ | |
| H | H | H | H | H | H | O | SO₂ | O | CH₃ | |
| H | H | H | H | H | H | O | SO₂ | O | OCH₃ | |
| H | H | H | H | H | H | O | SO₂ | CH₂ | OCH₃ | |
| CH₃ | H | H | H | H | H | O | O | CH₂ | OCF₂H | |
| CH₃ | H | H | H | H | H | O | O | O | OCF₂H | |
| CH₃ | H | H | Cl | H | H | O | O | O | OCF₂H | |
| CH₃ | H | H | H | H | H | O | SO₂ | O | OCF₂H | |
| CH₃ | H | H | H | H | H | O | SO | O | OCF₂H | |
| CH₃ | CH₃ | H | H | H | H | O | SO₂ | O | OCF₂H | |
| CH₃ | H | H | Cl | H | H | O | O | O | CH₃ | |
| n-butyl | H | H | H | H | H | O | O | O | CH₃ | |
| H | C₂H₅ | H | H | H | H | O | SO₂ | O | CH₃ | |
| H | n-C₃H₇ | H | H | H | H | O | SO₂ | O | CH₃ | |
| H | n-butyl | H | H | H | H | O | SO₂ | O | CH₃ | |

TABLE IIb

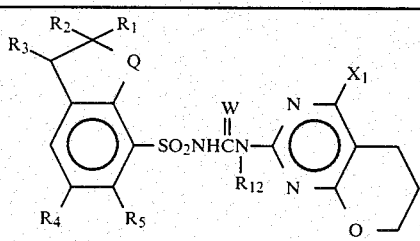

| R₁ | R₂ | R₃ | R₄ | R₅ | R₁₂ | W | Q | X₁ | m.p. (°C.) |
|---|---|---|---|---|---|---|---|---|---|
| CH₃ | CH₃ | H | H | H | H | O | O | CH₃ | |
| CH₃ | H | H | H | H | H | O | O | CH₃ | |
| CH₃ | CH₃ | H | H | H | H | O | O | OCH₃ | |
| CH₃ | H | H | H | H | H | O | O | OCH₃ | |
| CH₃ | H | H | H | H | H | O | S | OCH₃ | |
| CH₃ | H | H | H | H | H | O | SO₂ | OCH₃ | |
| CH₃ | CH₃ | H | H | H | H | O | O | OC₂H₅ | |
| CH₃ | H | H | H | H | H | O | O | OC₂H₅ | |
| CH₃ | CH₃ | H | H | H | H | O | S | OCH₃ | |
| CH₃ | CH₃ | H | H | H | H | O | SO₂ | OCH₃ | |
| CH₃ | H | H | H | H | H | O | S | CH₃ | |
| CH₃ | CH₃ | H | H | H | H | O | S | CH₃ | |
| CH₃ | H | H | H | H | H | O | SO₂ | CH₃ | |
| CH₃ | CH₃ | H | H | H | H | O | SO₂ | CH₃ | |
| H | H | H | H | H | H | O | SO₂ | OCH₃ | |
| H | H | H | H | H | H | O | SO₂ | CH₃ | |
| H | H | H | H | H | H | O | O | CH₃ | |
| H | H | H | H | H | H | O | O | OCH₃ | |
| CH₃ | H | CH₃ | H | H | H | O | O | CH₃ | |
| CH₃ | H | H | H | H | H | O | O | OCF₂H | |
| CH₃ | H | H | H | H | H | O | SO₂ | OCF₂H | |
| CH₃ | CH₃ | H | H | H | H | O | SO₂ | OCF₂H | |

TABLE IIc

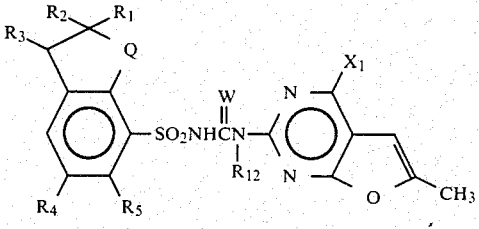

| R₁ | R₂ | R₃ | R₄ | R₅ | R₁₂ | W | Q | X₁ | m.p. (°C.) |
|---|---|---|---|---|---|---|---|---|---|
| CH₃ | CH₃ | H | H | H | H | O | O | CH₃ | |
| CH₃ | H | H | H | H | H | O | O | CH₃ | |
| CH₃ | H | CH₃ | H | H | H | O | O | CH₃ | |
| CH₃ | H | H | H | H | H | O | SO₂ | CH₃ | 219–221° |
| H | H | H | H | H | H | O | SO₂ | CH₃ | |
| CH₃ | CH₃ | H | Cl | H | H | O | O | CH₃ | |
| CH₃ | CH₃ | H | H | H | H | O | O | OCH₃ | |
| CH₃ | H | H | H | H | H | O | O | OCH₃ | |
| CH₃ | H | H | H | H | H | O | SO₂ | OCH₃ | |
| CH₃ | CH₃ | H | H | H | H | O | SO₂ | OCH₃ | |
| CH₃ | CH₃ | H | H | H | H | O | O | OC₂H₅ | |
| CH₃ | H | H | H | H | H | O | O | OC₂H₅ | |
| CH₃ | CH₃ | H | H | H | H | O | SO₂ | CH₃ | 230–232° |
| H | H | H | H | H | H | O | SO₂ | OCH₃ | |
| CH₃ | H | H | H | H | H | O | S | CH₃ | |
| CH₃ | CH₃ | H | H | H | H | O | S | OCH₃ | |
| CH₃ | H | CH₃ | H | H | H | O | O | OCH₃ | |
| CH₃ | H | H | H | H | H | S | O | CH₃ | |
| CH₃ | H | H | Cl | H | H | O | O | CH₃ | |
| CH₃ | H | H | H | H | H | O | O | OCF₂H | |
| CH₃ | H | H | H | H | H | O | SO₂ | OCF₂H | |
| CH₃ | CH₃ | H | H | H | H | O | SO₂ | OCF₂H | |
| CH₃ | H | H | H | H | CH₃ | O | O | CH₃ | |

TABLE IId

| R₁ | R₂ | R₃ | R₄ | R₅ | R₁₂ | W | Q | X₂ | Y₂ | m.p. (°C.) |
|---|---|---|---|---|---|---|---|---|---|---|
| CH₃ | CH₃ | H | H | H | H | O | O | CH₃ | OCH₃ | |
| CH₃ | H | H | H | H | H | O | O | CH₃ | OCH₃ | 195–198° |
| CH₃ | H | CH₃ | H | H | H | O | O | CH₃ | OCH₃ | |
| H | H | H | H | H | H | O | O | CH₃ | OCH₃ | |
| C₂H₅ | H | H | H | H | H | O | O | CH₃ | OCH₃ | |
| n-C₃H₇ | H | H | H | H | H | O | O | CH₃ | OCH₃ | |
| CH₃ | CH₃ | H | H | H | H | O | O | CH₃ | SCH₃ | |
| CH₃ | H | H | H | H | H | O | O | CH₃ | SCH₃ | |
| CH₃ | H | CH₃ | H | H | H | O | O | CH₃ | SCH₃ | |
| H | H | H | H | H | H | O | O | CH₃ | SCH₃ | |
| C₂H₅ | H | H | H | H | H | O | O | CH₃ | SCH₃ | |
| n-C₃H₇ | H | H | H | H | H | O | O | CH₃ | SCH₃ | |
| CH₃ | H | H | H | H | H | O | O | CH₃ | OC₂H₅ | |
| CH₃ | CH₃ | H | H | H | H | O | O | CH₃ | OC₂H₅ | |
| CH₃ | H | H | H | H | H | O | O | CH₃ | SC₂H₅ | |
| CH₃ | CH₃ | H | H | H | H | O | O | CH₃ | SC₂H₅ | |
| CH₃ | H | H | H | H | H | O | O | CH₃ | C₂H₅ | |
| CH₃ | CH₃ | H | H | H | H | O | O | CH₃ | C₂H₅ | |
| CH₃ | H | H | H | H | H | O | O | CH₃ | CH₃ | |
| CH₃ | CH₃ | H | H | H | H | O | O | CH₃ | CH₃ | |
| CH₃ | H | H | H | H | H | O | O | C₂H₅ | OCH₃ | |
| CH₃ | CH₃ | H | H | H | H | O | O | C₂H₅ | SCH₃ | |
| CH₃ | H | H | H | H | H | O | O | CH₂CF₃ | OCH₃ | |
| CH₃ | H | H | H | H | H | O | O | CH₂CF₃ | SCH₃ | |
| CH₃ | H | H | H | H | H | S | O | CH₃ | OCH₃ | |
| CH₃ | CH₃ | H | H | H | H | S | O | CH₃ | OCH₃ | |
| CH₃ | CH₃ | H | H | H | H | O | SO₂ | CH₃ | OCH₃ | |
| CH₃ | H | H | H | H | H | O | SO₂ | CH₃ | OCH₃ | 204–206° |
| CH₃ | H | CH₃ | H | H | H | O | SO₂ | CH₃ | OCH₃ | |
| H | H | H | H | H | H | O | SO₂ | CH₃ | OCH₃ | |
| C₂H₅ | H | H | H | H | H | O | SO₂ | CH₃ | OCH₃ | |
| n-C₃H₇ | H | H | H | H | H | O | SO₂ | CH₃ | OCH₃ | |
| CH₃ | CH₃ | H | H | H | H | O | SO₂ | CH₃ | SCH₃ | |
| CH₃ | H | H | H | H | H | O | SO₂ | CH₃ | SCH₃ | |
| CH₃ | H | CH₃ | H | H | H | O | SO₂ | CH₃ | SCH₃ | |
| H | H | H | H | H | H | O | SO₂ | CH₃ | SCH₃ | |
| C₂H₅ | H | H | H | H | H | O | SO₂ | CH₃ | SCH₃ | |
| n-C₃H₇ | H | H | H | H | H | O | SO₂ | CH₃ | SCH₃ | |
| CH₃ | CH₃ | H | H | H | H | O | S | CH₃ | OCH₃ | |
| CH₃ | H | H | H | H | H | O | S | CH₃ | OCH₃ | |
| H | H | H | H | H | H | O | S | CH₃ | OCH₃ | |
| C₂H₅ | H | H | H | H | H | O | S | CH₃ | OCH₃ | |
| CH₃ | CH₃ | H | H | H | H | O | S | CH₃ | SCH₃ | |
| CH₃ | H | H | H | H | H | O | S | CH₃ | SCH₃ | |
| H | H | H | H | H | H | O | S | CH₃ | SCH₃ | |
| C₂H₅ | H | H | H | H | H | O | S | CH₃ | SCH₃ | |
| CH₃ | H | CH₃ | H | H | H | O | S | CH₃ | OCH₃ | |
| CH₃ | H | H | H | H | H | O | SO₂ | C₂H₅ | OCH₃ | |
| CH₃ | CH₃ | H | H | H | H | O | S | C₂H₅ | SCH₃ | |
| CH₃ | CH₃ | H | H | H | H | O | SO₂ | CH₂CF₃ | OCH₃ | |
| CH₃ | H | H | H | H | H | O | S | CH₂CF₃ | SCH₃ | |
| CH₃ | CH₃ | H | H | H | H | O | SO₂ | CH₃ | OC₂H₅ | |
| CH₃ | CH₃ | H | H | H | H | O | S | CH₃ | SC₂H₅ | |
| CH₃ | H | H | H | H | H | O | SO₂ | CH₃ | C₂H₅ | |
| CH₃ | H | H | H | H | H | O | S | CH₃ | CH₃ | |
| CH₃ | CH₃ | H | H | H | H | S | S | CH₃ | OCH₃ | |
| CH₃ | CH₃ | H | H | H | CH₃ | O | O | CH₃ | OCH₃ | |
| CH₃ | H | H | H | H | H | O | SO | CH₃ | OCH₃ | |
| CH₃ | H | H | CH₃ | H | H | O | O | CH₃ | OCH₃ | |
| CH₃ | H | H | H | Cl | H | O | O | CH₃ | OCH₃ | |
| CH₃ | H | H | Cl | H | H | O | O | CH₃ | OCH₃ | |
| n-butyl | H | H | H | H | H | O | O | CH₃ | OCH₃ | |
| H | C₂H₅ | H | H | H | H | O | SO₂ | CH₃ | OCH₃ | |
| H | n-C₃H₇ | H | H | H | H | O | SO₂ | CH₃ | OCH₃ | |
| H | n-butyl | H | H | H | H | O | SO₂ | CH₃ | OCH₃ | |

TABLE IIe

Structure: phenyl ring substituted with R4, R5, and a CR1R2R3-Q- group, bearing -SO2NHC(=W)N(R12)- linked to a pyrimidine with OCH3 and X3 substituents.

| R1 | R2 | R3 | R4 | R5 | R12 | W | Q | X3 | m.p. (°C.) |
|---|---|---|---|---|---|---|---|---|---|
| CH3 | H | H | H | H | H | O | O | CH3 | |
| H | CH3 | H | H | H | H | O | O | OCH3 | |
| H | CH3 | H | H | H | H | O | SO2 | CH3 | |
| H | CH3 | H | H | H | H | O | SO2 | OCH3 | |
| CH3 | CH3 | H | H | H | H | O | SO2 | CH3 | |
| CH3 | CH3 | H | H | H | H | O | SO2 | OCH3 | |
| CH3 | H | CH3 | H | H | H | O | O | OCH3 | |
| CH3 | H | H | Cl | H | H | O | O | CH3 | |
| CH3 | H | H | Cl | H | H | O | O | OCH3 | |
| CH3 | CH3 | H | H | H | H | O | SO | OCH3 | |
| CH3 | H | H | H | H | H | O | S | OCH3 | |
| CH3 | H | H | H | H | CH3 | O | O | OCH3 | |

TABLE III

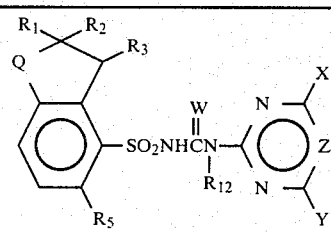

| R1 | R2 | R3 | R5 | R12 | W | Q | X | Y | Z | m.p. (°C.) |
|---|---|---|---|---|---|---|---|---|---|---|
| H | H | H | H | H | O | O | OCH3 | OCH3 | CH | 177–180° |
| H | H | H | H | H | O | O | OCH3 | CH3 | N | |
| H | H | H | H | H | O | S | OCH3 | OCH3 | CH | |
| H | H | H | H | H | O | S | OCH3 | CH3 | N | |
| H | H | H | H | H | O | SO2 | OCH3 | OCH3 | CH | |
| H | H | H | H | H | O | SO2 | OCH3 | CH3 | N | |
| CH3 | H | CH3 | H | H | O | SO2 | OCH3 | OCH3 | CH | |
| CH3 | H | CH3 | H | H | O | SO2 | OCH3 | CH3 | CH | |
| H | H | H | H | H | S | O | OCH3 | OCH3 | CH | |
| H | H | H | H | CH3 | O | O | OCH3 | OCH3 | CH | |
| H | H | H | H | H | O | SO | OCH3 | OCH3 | CH | |
| H | H | H | H | H | O | O | Cl | OCH3 | CH | |
| H | H | H | H | H | O | O | OCH3 | CH2OCH3 | CH | |
| H | H | H | H | H | O | O | OCH3 | N(CH3)2 | CH | |
| H | H | H | H | H | O | O | OCH3 | OCF2H | CH | |
| H | H | H | H | H | O | O | OCF2H | CH3 | CH | |

TABLE IIIa

Structure: aryl-SO2NHC(=W)N(R12)- linked to fused bicyclic pyrimidine with X1 and Y1.

| R1 | R2 | R3 | R5 | R12 | W | Q | Y1 | X1 | m.p. (°C.) |
|---|---|---|---|---|---|---|---|---|---|
| H | H | H | H | H | O | O | O | CH3 | |
| H | H | H | H | H | O | O | O | OCH3 | |
| H | H | H | H | H | O | O | O | OC2H5 | |
| H | H | H | H | H | O | O | CH2 | CH3 | |
| H | H | H | H | H | O | O | CH2 | OCH3 | |
| H | H | H | H | H | O | O | CH2 | OC2H5 | |
| H | H | H | H | H | O | S | O | CH3 | |

TABLE IIIa-continued

| R1 | R2 | R3 | R5 | R12 | W | Q | Y1 | X1 | m.p. (°C.) |
|---|---|---|---|---|---|---|---|---|---|
| H | H | H | H | H | O | SO2 | O | CH3 | |
| H | H | H | H | H | O | S | O | OCH3 | |
| H | H | H | H | H | O | SO2 | O | OCH3 | |
| H | H | H | H | H | O | S | CH2 | OCH3 | |
| H | H | H | H | H | O | SO2 | CH2 | OCH3 | |
| CH3 | H | CH3 | H | H | O | SO2 | O | OCH3 | |
| CH3 | H | CH3 | H | H | O | SO2 | O | CH3 | |
| H | H | H | H | H | O | O | O | OCF2H | |

TABLE IIIb

Structure with fused pyrimidine containing O in the ring.

| R1 | R2 | R3 | R5 | R12 | Q | X1 | W | m.p. (°C.) |
|---|---|---|---|---|---|---|---|---|
| H | H | H | H | H | O | CH3 | O | |
| H | H | H | H | H | SO2 | CH3 | O | |
| H | H | H | H | H | O | OCH3 | O | |
| CH3 | H | CH3 | H | H | S | OCH3 | O | |
| H | H | H | H | H | SO2 | OCH3 | O | |
| CH3 | H | CH3 | Cl | H | O | OCH3 | O | |
| H | H | H | H | H | O | OC2H5 | O | |
| H | H | H | H | H | S | CH3 | O | |
| H | H | H | H | H | SO | CH3 | O | |
| CH3 | H | CH3 | H | H | O | CH3 | O | |
| H | H | H | H | H | O | CH3 | S | |

TABLE IIIb-continued

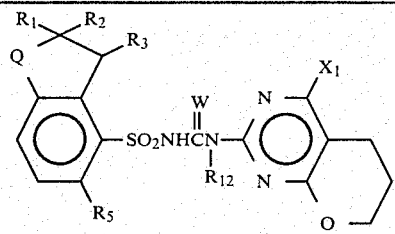

| R<sub>1</sub> | R<sub>2</sub> | R<sub>3</sub> | R<sub>5</sub> | R<sub>12</sub> | Q | X<sub>1</sub> | W | m.p. (°C.) |
|---|---|---|---|---|---|---|---|---|
| H | H | H | H | H | O | OCF$_2$H | O | |

TABLE IIIc

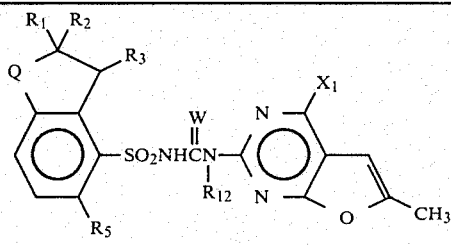

| $R_1$ | $R_2$ | $R_3$ | $R_5$ | $R_{12}$ | Q | $X_1$ | W | m.p. (°C.) |
|---|---|---|---|---|---|---|---|---|
| CH$_3$ | H | CH$_3$ | H | H | O | CH$_3$ | H | |
| H | H | CH$_3$ | H | H | SO$_2$ | CH$_3$ | H | |
| H | H | CH$_3$ | CH$_3$ | H | SO$_2$ | CH$_3$ | H | |
| H | H | CH$_3$ | Cl | H | SO$_2$ | CH$_3$ | H | |
| H | H | H | H | H | O | OCH$_3$ | H | |
| H | H | H | H | H | O | OC$_2$H$_5$ | H | |
| H | H | H | H | H | O | CH$_3$ | O | |
| H | H | H | H | H | S | CH$_3$ | O | |
| H | H | H | H | H | SO$_2$ | CH$_3$ | O | |
| H | H | H | H | H | SO | CH$_3$ | O | |
| H | H | H | H | H | O | CH$_3$ | S | |
| CH$_3$ | H | CH$_3$ | H | H | O | OCH$_3$ | O | |
| H | H | H | H | H | O | OCF$_2$H | O | |

TABLE IIId

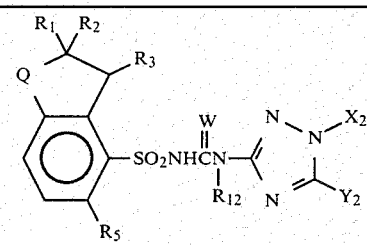

| $R_1$ | $R_2$ | $R_3$ | $R_5$ | $R_{12}$ | W | Q | $X_2$ | $Y_2$ | m.p. (°C.) |
|---|---|---|---|---|---|---|---|---|---|
| H | H | H | H | H | O | O | CH$_3$ | OCH$_3$ | |
| H | H | H | H | H | O | O | CH$_3$ | SCH$_3$ | |
| H | H | H | H | H | O | S | CH$_3$ | OCH$_3$ | |
| H | H | H | H | H | O | SO$_2$ | CH$_3$ | OCH$_3$ | |
| H | H | H | H | H | O | SO | CH$_3$ | OCH$_3$ | |
| H | H | H | H | H | S | O | CH$_3$ | OCH$_3$ | |
| CH$_3$ | H | CH$_3$ | H | H | O | O | CH$_3$ | OCH$_3$ | |
| CH$_3$ | H | CH$_3$ | H | H | O | O | CH$_3$ | SCH$_3$ | |
| H | H | CH$_3$ | Cl | H | O | SO$_2$ | CH$_3$ | OCH$_3$ | |

TABLE IIIe

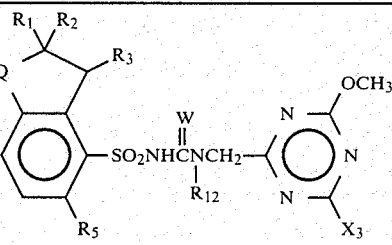

| $R_1$ | $R_2$ | $R_3$ | $R_5$ | $R_{12}$ | W | Q | $X_3$ | m.p. (°C.) |
|---|---|---|---|---|---|---|---|---|
| H | H | H | H | H | O | O | CH$_3$ | |
| H | H | H | H | H | O | O | OCH$_3$ | |
| H | H | H | H | H | O | SO$_2$ | OCH$_3$ | |
| H | H | H | H | H | O | SO | OCH$_3$ | |
| H | H | H | H | H | O | S | OCH$_3$ | |
| CH$_3$ | H | CH$_3$ | H | H | O | O | OCH$_3$ | |
| H | CH$_3$ | CH$_3$ | H | H | O | O | CH$_3$ | |
| H | H | CH$_3$ | H | H | O | O | OCH$_3$ | |

TABLE IV

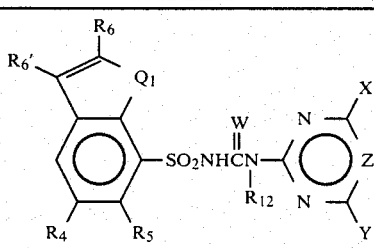

| $R_4$ | $R_5$ | $R_6$ | $R_6'$ | $R_{12}$ | W | $Q_1$ | X | Y | Z | m.p. (°C.) |
|---|---|---|---|---|---|---|---|---|---|---|
| H | H | H | H | H | O | O | OCH$_3$ | OCH$_3$ | CH | |
| H | H | H | H | H | O | O | OCH$_3$ | CH$_3$ | N | |
| H | H | CH$_3$ | H | H | O | O | OCH$_3$ | OCH$_3$ | CH | 188–191° |
| H | H | CH$_3$ | H | H | O | O | OCH$_3$ | CH$_3$ | CH | 208–211° |
| H | H | CH$_3$ | H | H | O | O | CH$_3$ | CH$_3$ | CH | 198–202° |
| H | H | CH$_3$ | H | H | O | O | OCH$_3$ | OCH$_3$ | N | 172–176° |
| H | H | CH$_3$ | H | H | O | O | OCH$_3$ | CH$_3$ | N | 178–181° |
| H | H | CH$_3$ | CH$_3$ | H | O | O | OCH$_3$ | OCH$_3$ | CH | |
| H | H | CH$_3$ | CH$_3$ | H | O | O | OCH$_3$ | CH$_3$ | CH | |
| H | H | CH$_3$ | CH$_3$ | H | O | O | CH$_3$ | CH$_3$ | CH | |
| H | H | CH$_3$ | CH$_3$ | H | O | O | OCH$_3$ | OCH$_3$ | N | |
| H | H | CH$_3$ | CH$_3$ | H | O | O | OCH$_3$ | CH$_3$ | N | |
| H | H | CH$_3$ | H | H | O | O | OCH$_3$ | OCH$_3$ | CH | |
| H | H | CH$_3$ | H | H | O | O | OCH$_3$ | CH$_3$ | N | |
| H | H | CH$_3$ | CH$_3$ | H | O | S | OCH$_3$ | OCH$_3$ | CH | |

TABLE IV-continued

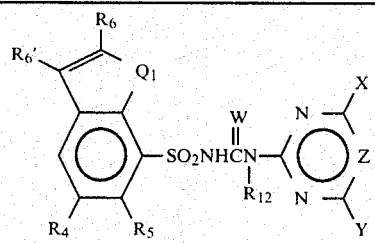

| R4 | R5 | R6 | R6' | R12 | W | Q1 | X | Y | Z | m.p. (°C.) |
|---|---|---|---|---|---|---|---|---|---|---|
| H | H | CH3 | CH3 | H | O | S | OCH3 | CH3 | CH | |
| H | H | CH3 | CH3 | H | O | S | CH3 | CH3 | CH | |
| H | H | CH3 | CH3 | H | O | S | OCH3 | OCH3 | N | |
| H | H | CH3 | CH3 | H | O | S | OCH3 | CH3 | N | |
| H | H | H | CH3 | H | O | S | OCH3 | OCH3 | CH | 216–218° |
| H | H | H | CH3 | H | O | S | OCH3 | CH3 | CH | 218–220° |
| H | H | H | CH3 | H | O | S | CH3 | CH3 | CH | |
| H | H | CH3 | H | H | O | O | CH3 | CH3 | N | 201–204° |
| H | H | H | CH3 | H | O | S | OCH3 | OCH3 | N | |
| H | H | H | CH3 | H | O | S | OCH3 | CH3 | N | |
| H | H | H | H | H | O | S | OCH3 | OCH3 | CH | 204–206° |
| H | H | H | H | H | O | S | OCH3 | CH3 | CH | 195–197° |
| H | H | H | H | H | O | S | OCH3 | OCH3 | N | |
| H | H | H | H | H | O | S | OCH3 | CH3 | N | |
| H | H | H | H | H | O | S | CH3 | CH3 | N | |
| H | H | CH3 | CH3 | H | O | SO2 | OCH3 | OCH3 | CH | 236–239° |
| H | H | CH3 | CH3 | H | O | SO2 | OCH3 | CH3 | CH | 237–239° |
| H | H | CH3 | CH3 | H | O | SO2 | CH3 | CH3 | CH | 249–252° |
| H | H | CH3 | CH3 | H | O | SO2 | OCH3 | OCH3 | N | 226–230° |
| H | H | H | CH3 | H | O | SO2 | OCH3 | CH3 | N | |
| H | H | H | H | H | O | SO2 | OCH3 | OCH3 | CH | |
| H | H | H | H | H | O | SO2 | OCH3 | CH3 | CH | |
| H | H | H | H | H | O | SO2 | OCH3 | OCH3 | N | |
| H | H | H | H | H | O | SO2 | OCH3 | CH3 | N | |
| H | H | CH3 | H | H | O | SO2 | OCH3 | OCH3 | CH | |
| H | H | H | CH3 | H | O | SO2 | OCH3 | CH3 | CH | |
| H | H | H | CH3 | H | O | SO3 | OCH3 | OCH3 | N | |
| H | H | H | CH3 | H | O | SO2 | CH3 | CH3 | CH | |
| H | H | CH3 | H | CH3 | O | O | OCH3 | OCH3 | CH | |
| H | H | CH3 | H | CH3 | O | O | OCH3 | OCH3 | N | |
| H | H | CH3 | CH3 | H | O | O | H | CH3 | OCH3 | |
| H | H | CH3 | CH3 | H | O | O | OCH3 | CH3 | CC2H5 | |
| H | H | H | H | H | O | S | CH3 | CH3 | CCl | |
| H | H | CH3 | CH3 | H | O | O | H | CH3 | CCl | |
| H | H | H | H | H | O | S | H | CH3 | CBr | |
| H | H | CH3 | CH3 | H | O | O | H | OCH3 | CCl | |
| H | H | H | CH3 | H | O | S | CH3 | CH3 | CBr | |
| H | H | CH3 | H | H | O | O | CH3 | NH2 | CH | |
| H | H | CH3 | CH3 | H | O | SO2 | CH3 | CH3 | N | 233–236°, |
| H | H | CH3 | H | H | O | O | CH3 | NHCH3 | CH | |
| H | H | CH3 | CH3 | H | O | O | CH3 | N(CH3)2 | CH | |
| H | H | CH3 | H | H | O | O | H | OCH3 | CBr | |
| H | H | H | H | H | O | S | CH3 | OC2H5 | CH | |
| H | H | CH3 | H | H | O | S | CH3 | OC2H5 | N | |
| H | H | CH3 | H | H | O | O | CH3 | CH2OCH3 | CH | |
| H | H | CH3 | CH3 | H | O | O | Cl | OCH3 | CH | |
| H | CH3 | CH3 | CH3 | H | O | SO2 | OCH3 | OCH3 | CH | |
| H | OCH3 | CH3 | CH3 | H | O | S | OCH3 | CH3 | CH | |
| H | Cl | CH3 | H | H | O | O | OCH3 | CH3 | N | |
| H | Br | CH3 | CH3 | H | O | S | OCH3 | OCH3 | CH | |
| H | NO2 | CH3 | CH3 | H | O | O | OCH3 | OCH3 | CH | |
| H | CO2CH3 | CH3 | CH3 | H | O | O | OCH3 | CH3 | CH | |
| H | CO2CH(CH3)2 | CH3 | CH3 | H | O | S | OCH3 | CH3 | N | |
| H | CO2CH2CH2CH3 | CH3 | CH3 | H | O | SO2 | OCH3 | CH3 | N | |
| H | CO2CH2CH=CH2 | CH3 | CH3 | H | O | O | CH3 | CH3 | CH | |
| H | CO2CH2CH2OCH3 | CH3 | CH3 | H | O | O | CH3 | CH3 | CH | |
| H | CO2CH2CH2Cl | CH3 | CH3 | CH3 | O | O | CH3 | CH3 | CH | |
| H | SO2CH3 | CH3 | CH3 | H | O | O | OCH3 | OCH3 | CH | |
| H | SO2CH(CH3)2 | CH3 | CH3 | H | O | O | OCH3 | CH3 | N | |
| H | SO2CH2CH2CH2CH3 | CH3 | CH3 | H | O | O | OCH3 | OCH3 | CH | |
| H | OSO2CH3 | CH3 | CH3 | H | O | O | OCH3 | CH3 | CH | |
| H | OSO2CH(CH3)2 | CH3 | CH3 | H | O | O | OCH3 | CH3 | N | |
| H | OSO2CH2CH2CH3 | CH3 | CH3 | H | O | O | OCH3 | OCH3 | CH | |
| H | OSO2CF3 | CH3 | CH3 | H | O | SO2 | OCH3 | CH3 | CH | |
| H | SO2N(CH3)2 | CH3 | CH3 | H | O | S | CH3 | OCH3 | CH | |
| H | SO2N(CH3)CH2CH3 | CH3 | CH3 | H | O | O | CH3 | OCH3 | N | |
| H | CO2C2H5 | CH3 | CH3 | H | O | O | CH3 | OCH3 | CH | |

TABLE IV-continued

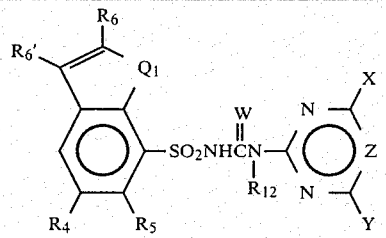

| R4 | R5 | R6 | R6' | R12 | W | Q1 | X | Y | Z | m.p. (°C.) |
|---|---|---|---|---|---|---|---|---|---|---|
| H | SO2C2H5 | CH3 | CH3 | H | O | O | OCH3 | OCH3 | CH | |
| H | OSO2C2H5 | CH3 | CH3 | H | O | O | CH3 | OCH3 | CH | |
| H | H | H | H | H | O | O | OCH3 | CH3 | CH | |
| H | H | H | H | H | O | O | CH3 | CH3 | CH | |
| H | H | H | H | H | O | O | OCH3 | OCH3 | N | |
| H | H | C2H5 | H | H | O | O | OCH3 | OCH3 | CH | |
| H | H | n-C3H7 | H | H | O | O | OCH3 | OCH3 | CH | |
| H | H | CH(CH3)2 | H | H | O | O | OCH3 | OCH3 | CH | |
| H | H | Cl | CH3 | H | O | O | OCH3 | OCH3 | CH | |
| H | H | Br | CH3 | H | O | O | OCH3 | OCH3 | CH | |
| H | H | CH3 | Cl | H | O | O | OCH3 | OCH3 | CH | |
| H | H | CH3 | Br | H | O | O | OCH3 | OCH3 | CH | |
| H | H | CH3 | H | H | O | S | OCH3 | OCH3 | CH | 199–201° |
| H | H | CH3 | H | H | O | S | CH3 | OCH3 | CH | 202–204° |
| H | H | CH3 | H | H | O | S | CH3 | CH3 | CH | |
| H | H | CH3 | H | H | O | S | CH3 | CH3 | N | |
| H | H | CH3 | H | H | O | S | OCH3 | OCH3 | N | |
| H | H | H | H | H | O | SO2 | CH3 | CH3 | CH | |
| H | H | CH3 | H | H | O | SO2 | OCH3 | CH3 | CH | |
| H | H | CH3 | H | H | O | SO2 | CH3 | CH3 | CH | |
| H | H | CH3 | H | H | O | SO2 | OCH3 | OCH3 | N | |
| H | H | CH3 | H | H | O | SO2 | CH3 | CH3 | N | |
| H | H | CH3 | CH3 | H | O | SO2 | OCH2 | CH3 | N | |
| H | H | CH3 | H | H | O | O | Cl | OCH3 | CH | |
| H | H | H | H | H | O | SO2 | Cl | OCH3 | CH | |
| H | H | CH3 | CH3 | H | O | SO2 | OCH3 | CH(OCH3)2 | N | |
| H | H | CH3 | H | H | O | O | CH3 | C2H5 | CH | |
| H | H | CH3 | H | H | O | O | CH3 | CF3 | CH | |
| H | H | H | H | H | O | S | CH3 | OCH2CH=CH2 | N | |
| H | H | CH3 | H | H | O | O | CH3 | OCH2C≡CH | N | |
| H | H | CH3 | H | H | O | O | OCH3 | OCH2CF3 | N | |
| H | H | CH3 | H | H | O | O | CH3 | 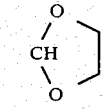 | CH | |
| H | H | H | H | H | O | S | Cl | NH2 | CH | |
| H | H | CH3 | H | H | O | O | Cl | NHCH3 | CH | |
| H | H | CH3 | CH3 | H | O | SO2 | Cl | N(CH3)2 | CH | |
| H | H | CH3 | H | H | S | O | OCH3 | OCH3 | CH | |
| H | H | H | H | H | S | S | OCH3 | OCH3 | CH | |
| H | H | H | H | H | S | SO2 | OCH3 | OCH3 | CH | |
| H | 4-5- or 6- Cl | H | CH3 | H | O | S | CH3 | CH3 | CH | 218–221° |
| H | 4-5- or 6- Cl | H | CH3 | H | O | S | CH3 | OCH3 | CH | 231–233° |
| H | 4-5- or 6- Cl | H | CH3 | H | O | S | OCH3 | OCH3 | CH | 218–221° |
| H | H | CH3 | H | H | O | O | OCH3 | SCH3 | N | |
| H | H | CH3 | H | H | O | S | OCH3 | SCH3 | CH | |
| H | H | H | H | H | O | S | OCH3 | SCH3 | N | |
| H | H | CH3 | H | H | O | O | CH3 | SCH3 | CH | |
| H | H | C2H5 | H | H | O | S | OCH3 | OCH3 | CH | |
| Cl | H | CH3 | H | H | O | O | OCH3 | OCH3 | CH | |
| Cl | H | CH3 | H | H | O | O | OCH3 | OCH3 | CH | |
| Cl | H | CH3 | H | H | O | O | CH3 | CH3 | CH | |
| Cl | H | CH3 | H | H | O | O | OCH3 | OCH3 | N | |
| Cl | H | CH3 | H | H | O | O | CH3 | CH3 | N | |
| Cl | H | CH3 | H | H | O | O | OCH3 | OCH2CF3 | N | |
| Cl | H | CH3 | H | H | O | O | Cl | OCH3 | CH | |
| Cl | H | CH3 | CH3 | H | O | S | OCH3 | OCH3 | CH | |
| Cl | H | CH3 | CH3 | H | O | SO2 | OCH3 | OCH3 | CH | |

TABLE IV-continued

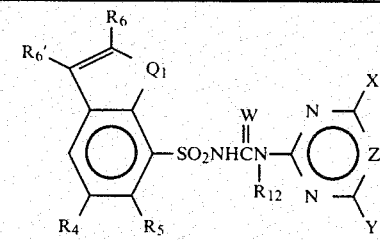

| R4 | R5 | R6 | R6' | R12 | W | Q1 | X | Y | Z | m.p. (°C.) |
|---|---|---|---|---|---|---|---|---|---|---|
| CH3 | H | CH3 | CH3 | H | O | O | OCH3 | OCH3 | CH | |
| CF3 | H | CH3 | H | H | O | O | OCH3 | OCH3 | CH | |
| CF3 | H | CH3 | CH3 | H | O | S | OCH3 | OCH3 | CH | |
| CF3 | H | CH3 | CH3 | H | O | SO2 | OCH3 | OCH3 | CH | |
| OCH3 | H | CH3 | H | H | O | O | OCH3 | OCH3 | CH | |
| Br | H | CH3 | H | H | O | O | OCH3 | OCH3 | CH | |
| Br | H | CH3 | H | H | O | O | CH3 | OCH3 | CH | |
| Br | H | CH3 | H | H | O | O | CH3 | CH3 | N | |
| Br | H | CH3 | H | H | O | O | OCH3 | CH3 | N | |
| Br | H | CH3 | H | H | O | O | OCH3 | OCH3 | N | |
| Br | H | CH3 | H | H | O | O | Cl | OCH3 | CH | |
| Br | H | CH3 | H | H | O | O | OCH3 | OCH2CF3 | CH | |
| F | H | CH3 | H | H | O | O | OCH3 | OCH3 | CH | |
| SCH3 | H | CH3 | H | H | O | O | OCH3 | OCH3 | CH | |
| OCF2H | H | CH3 | CH3 | H | O | O | OCH3 | OCH3 | CH | |
| H | F | CH3 | H | H | O | O | OCH3 | OCH3 | CH | |
| H | CF3 | CH3 | H | H | O | O | OCH3 | OCH3 | CH | |
| H | SCH3 | CH3 | H | H | O | S | OCH3 | OCH3 | CH | |
| H | OCF2H | CH3 | H | H | O | O | OCH3 | OCH3 | CH | |
| H | SO2N(OCH3)CH3 | CH3 | CH3 | H | O | SO2 | OCH3 | OCH3 | CH | |
| H | H | n-butyl | H | H | O | O | OCH3 | OCH3 | CH | |
| H | H | CH3 | H | H | O | O | F | OCH3 | CH | |
| H | H | CH3 | H | H | O | S | F | OCH3 | CH3 | |
| H | H | CH3 | H | H | O | O | OCH3 | CH(OC2H5)2 | CH | |
| H | H | CH3 | H | H | O | S | OCH3 | CH(OC2H5)2 | CH | |
| H | H | CH3 | H | H | O | O | OCH3 | C2H5 | CH | |
| H | H | CH3 | H | H | O | S | OCH3 | C2H5 | CH | |
| H | H | CH3 | H | H | O | O | OCH3 | 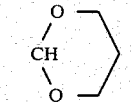 | CH | |
| H | H | CH3 | H | H | O | S | OCH3 | 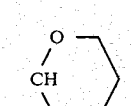 | CH | |
| H | H | H | H | H | O | S | OCH3 | 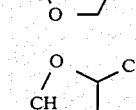 | CH | |
| H | H | CH3 | H | H | O | O | OCH3 | 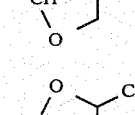 | CH | |
| H | H | CH3 | H | H | O | O | OCH3 | OCH2CH2Cl | CH | |
| H | H | CH3 | H | H | O | S | OCH3 | OCH2CH2Cl | N | |
| H | H | CH3 | H | H | O | S | OCH3 | OCH2CH2Br | CH | |
| H | H | CH3 | H | H | O | O | OCH3 | OCH2CH2Br | N | |
| H | H | CH3 | H | H | O | S | OCH3 | OCH2CH2F | CH | |
| H | H | CH3 | H | H | O | O | OCH3 | OCH2CH2F | N | |
| H | H | CH3 | H | H | O | O | OCH3 | CN | CH | |
| H | H | H | H | H | O | S | OCH3 | CN | N | |
| H | H | CH3 | H | H | O | O | OCH3 | CH2OCH2CH3 | CH | |
| H | H | CH3 | H | H | O | S | OCH3 | CH2OCH2CH3 | CH | |
| H | H | CH3 | H | H | O | O | OCH3 | OCH2CH2OCH3 | CH | |
| H | H | CH3 | H | H | O | S | OCH3 | OCH2CH2OCH3 | CH | |
| H | H | CH3 | H | H | O | O | CH3 | OCF2H | CH | |
| H | H | CH3 | H | H | O | O | OCH3 | OCF2H | CH | |
| H | H | CH3 | H | H | O | S | CH3 | SCF2H | CH | |
| H | H | CH3 | H | H | O | O | OCH3 | SCF2H | CH | |

TABLE IV-continued

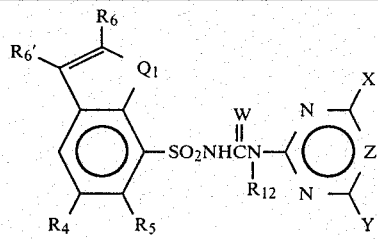

| R4 | R5 | R6 | R6' | R12 | W | Q1 | X | Y | Z | m.p. (°C.) |
|---|---|---|---|---|---|---|---|---|---|---|
| H | H | CH3 | H | H | O | O | SCF2H | OCH3 | CH | |
| H | H | H | H | H | O | S | CH3 | OCF2CHFCl | CH | |
| H | H | CH3 | H | H | O | O | OCH3 | OCF2CHFCl | CH | |
| H | H | CH3 | H | H | O | O | CH3 | OCF2CHFBr | CH | |
| H | H | CH3 | H | H | O | S | OCH3 | OCF2CHFBr | CH | |
| H | H | CH3 | H | H | O | O | CH3 | OCF2CF2H | CH | |
| H | H | CH3 | H | H | O | O | OCH3 | OCF2CF2H | CH | |
| H | H | CH3 | H | H | O | SO2 | CH3 | OCF2CHFCF3 | CH | |
| H | H | CH3 | H | H | O | O | OCH3 | OCF2CHFCF3 | CH | |
| H | H | CH3 | H | H | O | O | OCF2H | OCF2H | CH | |
| H | H | CH3 | H | H | O | O | OCF2H | SCF2H | CH | |
| H | H | CH3 | H | H | O | O | SCF2H | SCF2H | CH | |
| H | H | CH3 | H | H | O | O | OCF2H | CH(OCH3)2 | CH | |
| H | H | CH3 | H | H | O | O | CH3 | OCF2H | N | |
| H | H | CH3 | H | H | O | O | OCH3 | OCF2H | N | |
| H | H | CH3 | H | H | O | S | CH3 | SCF2H | N | |
| H | H | CH3 | H | H | O | O | OCH3 | SCF2H | N | |
| H | H | CH3 | H | H | O | O | OCH3 | OCF2CF2H | N | |
| H | H | CH3 | H | H | O | S | OCH3 | OCF2CHFCl | N | |
| H | H | CH3 | H | H | O | O | OCH3 | OCF2CHFCF3 | N | |
| H | H | CH3 | H | H | O | O | Cl | OCF2H | CH | |

TABLE IVa

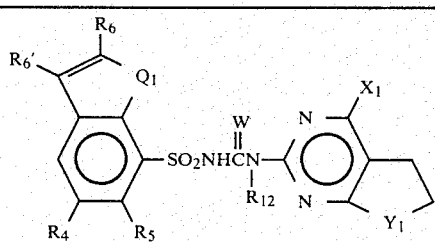

| R4 | R5 | R6 | R6' | R12 | W | Q1 | Y1 | X1 | m.p. (°C.) |
|---|---|---|---|---|---|---|---|---|---|
| H | H | CH3 | H | H | O | O | O | CH3 | |
| H | H | CH3 | H | H | O | O | O | OCH3 | |
| H | H | CH3 | H | H | O | O | O | OC2H5 | |
| H | H | H | H | H | O | O | O | CH3 | |
| H | H | CH3 | CH3 | H | O | O | O | CH3 | |
| H | H | CH3 | H | H | O | O | CH2 | OCH3 | |
| H | H | CH3 | H | H | O | O | CH2 | CH3 | |
| H | H | CH3 | H | H | O | O | CH2 | OC2H5 | |
| H | H | H | H | H | O | S | O | CH3 | |
| H | H | H | H | H | O | SO2 | O | CH3 | |
| H | H | CH3 | CH3 | H | O | SO2 | O | CH3 | |
| H | H | CH3 | H | H | O | S | O | CH3 | |
| H | H | CH3 | H | H | S | O | O | CH3 | |
| H | Cl | CH3 | H | H | O | O | O | CH3 | |
| H | H | CH3 | H | CH3 | O | O | O | CH3 | |
| H | H | CH3 | H | H | O | O | CH2 | OCF2H | |
| H | H | CH3 | H | H | O | O | O | OCF2H | |
| H | H | CH3 | H | H | O | S | CH2 | OCF2H | |
| H | H | CH3 | H | H | O | S | O | OCF2H | |
| Cl | H | CH3 | H | H | O | O | O | OCF2H | |
| Cl | H | CH3 | H | H | O | O | CH2 | CH3 | |

TABLE IVb

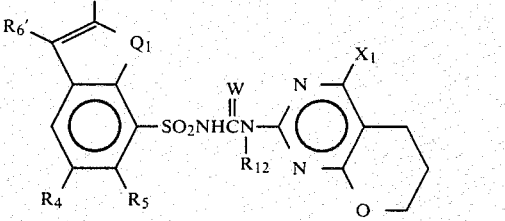

| R4 | R5 | R6 | R6' | R12 | W | Q1 | X1 | m.p. (°C.) |
|---|---|---|---|---|---|---|---|---|
| H | H | CH3 | H | H | O | O | CH3 | |
| H | H | CH3 | H | H | O | O | OCH3 | |
| H | H | CH3 | H | H | O | O | OC2H5 | |
| H | H | CH3 | CH3 | H | O | O | CH3 | |
| H | H | H | H | H | O | O | CH3 | |
| H | H | CH3 | H | H | O | S | CH3 | |
| H | H | CH3 | H | CH3 | O | O | CH3 | |
| H | H | CH3 | CH3 | H | O | SO2 | CH3 | |
| H | H | H | H | H | O | S | CH3 | |
| H | H | H | H | H | O | S | OCH3 | |
| H | H | H | H | H | O | SO2 | OCH3 | |
| H | Cl | CH3 | H | H | O | O | CH3 | |
| H | H | CH3 | H | H | O | O | OCF2H | |
| H | H | CH3 | H | H | O | S | OCF2H | |

TABLE IVc

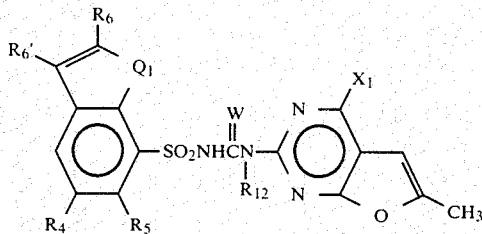

| R4 | R5 | R6 | R6' | R12 | W | Q1 | X1 | m.p. (°C.) |
|---|---|---|---|---|---|---|---|---|
| H | H | CH3 | CH3 | H | O | O | CH3 | |
| H | H | CH3 | H | H | O | O | CH3 | |
| H | H | H | H | H | O | O | CH3 | |
| H | H | CH3 | CH3 | H | O | SO2 | CH3 | |
| H | H | H | H | H | O | S | CH3 | |
| H | H | CH3 | H | H | O | SO2 | CH3 | |
| H | H | CH3 | H | H | O | S | CH3 | |
| H | H | CH3 | CH3 | H | O | O | OCH3 | |
| H | H | CH3 | H | H | O | O | OCH3 | |
| H | H | CH3 | CH3 | H | O | S | OCH3 | |
| H | H | CH3 | CH3 | H | O | SO2 | OCH3 | |
| H | H | H | H | H | O | S | OCH3 | |
| H | H | CH3 | H | H | O | S | OCH3 | |
| H | H | CH3 | H | H | O | O | OC2H5 | |
| H | H | CH3 | H | CH3 | O | O | CH3 | |
| H | Cl | CH3 | H | H | O | O | CH3 | |
| H | H | CH3 | H | H | S | O | CH3 | |
| H | H | CH3 | H | H | O | O | OCF2H | |
| H | H | CH3 | H | H | O | S | OCF2H | |
| Cl | H | CH3 | H | H | O | O | CH3 | |

TABLE IVd

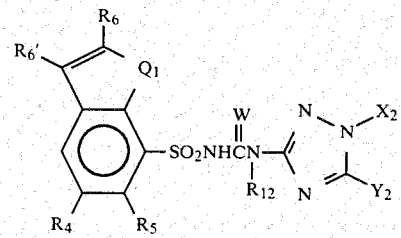

| R4 | R5 | R6 | R6' | R12 | W | Q1 | X2 | Y2 | m.p. (°C.) |
|---|---|---|---|---|---|---|---|---|---|
| H | H | CH3 | H | H | O | O | CH3 | OCH3 | |
| H | H | CH3 | CH3 | H | O | O | CH3 | OCH3 | |
| H | H | H | H | H | O | O | CH3 | OCH3 | |
| H | H | CH3 | H | H | O | O | CH3 | SCH3 | |
| H | H | CH3 | CH3 | H | O | O | CH3 | SCH3 | |
| H | H | H | H | H | O | O | CH3 | SCH3 | |
| H | H | H | H | H | O | S | CH3 | OCH3 | |
| H | H | H | H | H | O | S | CH3 | SCH3 | |
| H | H | CH3 | H | H | O | SO2 | CH3 | OCH3 | |
| H | H | CH3 | CH3 | H | O | SO2 | CH3 | SCH3 | |
| H | H | CH3 | H | CH3 | O | O | CH3 | OCH3 | |
| H | Cl | CH3 | H | H | O | O | CH3 | OCH3 | |
| H | H | CH3 | H | H | S | O | CH3 | OCH3 | |
| H | H | H | H | H | S | S | CH3 | OCH3 | |
| H | H | CH3 | CH3 | H | S | SO2 | CH3 | OCH3 | |
| H | H | H | H | H | O | S | C2H5 | OCH3 | |
| H | H | CH3 | H | H | O | O | CH2CF3 | OCH3 | |
| H | H | CH3 | CH3 | H | O | SO2 | CH3 | OC2H5 | |
| H | H | CH3 | H | H | O | O | CH3 | SC2H5 | |
| H | H | CH3 | H | H | O | O | CH3 | C2H5 | |
| H | H | CH3 | H | H | O | O | CH3 | CH3 | |
| Cl | H | CH3 | H | H | O | O | CH3 | OCH3 | |

TABLE IVe

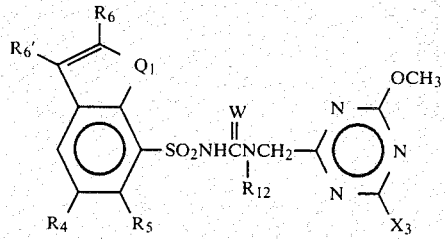

| R4 | R5 | R6 | R6' | R12 | W | Q1 | X3 | m.p. (°C.) |
|---|---|---|---|---|---|---|---|---|
| H | H | CH3 | H | H | O | O | CH3 | |
| H | H | CH3 | H | H | O | O | OCH3 | |
| Cl | H | CH3 | H | H | O | O | OCH3 | |
| Cl | H | CH3 | H | H | O | O | CH3 | |
| H | H | CH3 | CH3 | H | O | O | OCH3 | |
| H | H | CH3 | H | H | O | S | OCH3 | |
| H | H | H | H | H | O | S | OCH3 | |
| H | H | CH3 | H | CH3 | O | O | OCH3 | |
| H | H | CH3 | H | H | S | O | OCH3 | |
| H | H | CH3 | H | H | O | SO2 | OCH3 | |

TABLE V

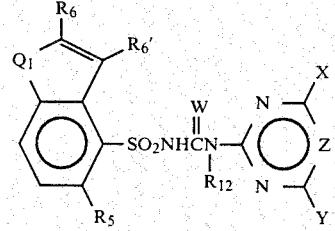

| R5 | R6 | R6' | R12 | W | Q1 | X | Y | Z | m.p. (°C.) |
|---|---|---|---|---|---|---|---|---|---|
| H | H | H | H | O | O | OCH3 | OCH3 | CH | |
| H | H | H | H | O | O | OCH3 | CH3 | N | |
| H | H | CH3 | H | O | O | OCH3 | OCH3 | CH | |
| H | H | CH3 | H | O | O | OCH3 | CH3 | N | |
| H | H | H | H | S | O | OCH3 | OCH3 | CH | |
| H | H | CH3 | H | O | S | OCH3 | OCH3 | CH | |
| H | H | CH3 | H | O | SO2 | OCH3 | OCH3 | CH | |
| H | H | CH3 | H | O | SO2 | OCH3 | CH3 | N | |
| H | CH3 | CH3 | H | O | O | OCH3 | OCH3 | CH | |
| H | H | H | H | O | O | OCH3 | OCF2H | CH | |
| H | H | H | H | O | S | OCH3 | OCF2H | CH | |

TABLE Va

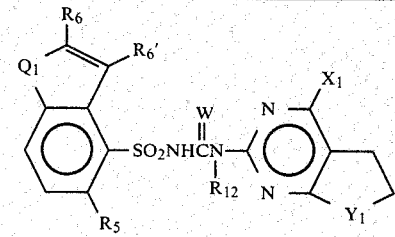

| R5 | R6 | R6' | R12 | W | Q1 | Y1 | X1 | m.p. (°C.) |
|---|---|---|---|---|---|---|---|---|
| H | H | CH3 | H | O | O | O | CH3 | |
| H | CH3 | CH3 | H | O | O | O | OCH3 | |
| H | H | CH3 | H | O | O | O | OC2H5 | |
| H | H | H | H | O | S | O | CH3 | |
| H | H | CH3 | H | O | SO2 | O | CH3 | |
| H | H | CH3 | H | O | O | CH2 | CH3 | |
| H | H | H | H | O | S | CH2 | OCH3 | |
| H | H | H | H | O | SO2 | CH2 | OC2H5 | |
| H | H | CH3 | H | S | O | O | CH3 | |
| Cl | H | CH3 | H | O | O | O | CH3 | |
| H | H | H | H | O | S | O | OCF2H | |

TABLE Va-continued

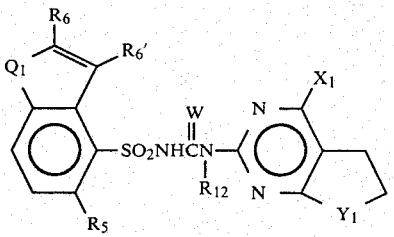

| R5 | R6 | R6' | R12 | W | Q1 | Y1 | X1 | m.p. (°C.) |
|----|----|-----|-----|---|----|----|----|-----------|
| H | H | H | H | O | O | O | OCF2H | |
| H | H | H | H | O | O | CH2 | OCF2H | |

TABLE Vb

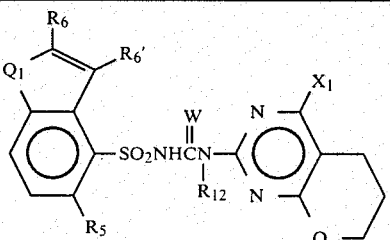

| R5 | R6 | R6' | R12 | W | Q1 | X1 | m.p. (°C.) |
|----|----|-----|-----|---|----|----|-----------|
| H | H | CH3 | H | O | O | CH3 | |
| H | H | CH3 | H | O | S | CH3 | |
| Cl | H | CH3 | H | O | O | CH3 | |
| H | H | CH3 | H | O | SO2 | CH3 | |
| H | CH3 | CH3 | H | O | O | OCH3 | |
| H | H | CH3 | H | O | S | OCH3 | |
| H | H | CH3 | CH3 | O | S | OCH3 | |
| H | H | CH3 | H | O | S | OCH3 | |
| H | H | H | H | O | O | OCH3 | |
| H | H | CH3 | H | O | O | OC2H5 | |
| H | H | H | H | S | O | CH3 | |
| H | H | CH3 | H | O | O | OCF2H | |
| H | H | CH3 | H | O | S | OCF2H | |

TABLE Vc

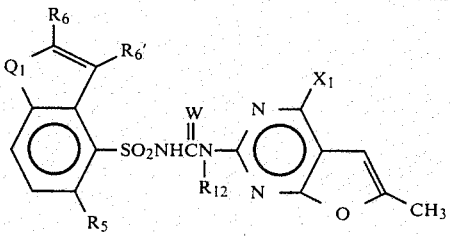

| R5 | R6 | R6' | R12 | W | Q1 | X1 | m.p. (°C.) |
|----|----|-----|-----|---|----|----|-----------|
| H | CH3 | CH3 | H | O | O | CH3 | |
| H | H | CH3 | H | O | S | CH3 | |
| H | H | CH3 | H | O | SO2 | CH3 | |
| H | H | CH3 | H | O | O | OCH3 | |
| H | H | CH3 | H | O | S | OCH3 | |
| H | CH3 | CH3 | H | O | SO2 | OCH3 | |
| H | H | CH3 | H | O | SO2 | OCH3 | |
| H | H | H | H | O | O | OC2H5 | |
| H | H | H | H | S | O | CH3 | |
| H | H | CH3 | H | S | SO2 | CH3 | |
| Cl | H | CH3 | H | O | O | CH3 | |
| H | H | H | H | O | O | OCF2H | |
| H | H | H | H | O | S | OCF2H | |

TABLE Vd

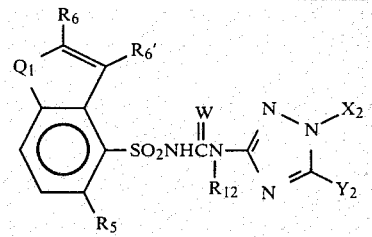

| R5 | R6 | R6' | R12 | W | Q1 | X2 | Y2 | m.p. (°C.) |
|----|----|-----|-----|---|----|----|----|-----------|
| H | H | CH3 | H | O | O | CH3 | OCH3 | |
| H | H | CH3 | H | O | O | CH3 | SCH3 | |
| H | CH3 | CH3 | H | O | O | CH3 | OCH3 | |
| H | H | CH3 | H | S | O | CH3 | OCH3 | |
| H | CH3 | CH3 | H | O | S | CH3 | OCH3 | |
| H | H | H | H | O | SO2 | CH3 | OCH3 | |
| Cl | H | CH3 | H | O | O | CH3 | OCH3 | |

TABLE Ve

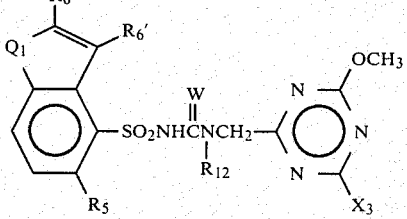

| R5 | R6 | R6' | R12 | W | Q1 | X3 | m.p. (°C.) |
|----|----|-----|-----|---|----|----|-----------|
| H | H | H | H | O | O | CH3 | |
| H | H | H | H | O | O | OCH3 | |
| H | H | H | H | O | S | CH3 | |
| H | H | H | H | O | S | OCH3 | |
| H | H | CH3 | H | O | O | OCH3 | |
| H | CH3 | CH3 | H | O | O | CH3 | |
| H | H | H | H | O | SO2 | CH3 | |

Formulations

Useful formulations of the compounds of Formulae I, I', II and II' can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE VI

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength | 90-99 | 0-10 | 0-2 |

TABLE VI-continued

| Compositions | Active Ingredient | Weight Percent* Diluent(s) | Surfactant(s) |
| --- | --- | --- | --- |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 21

| Wettable Powder | |
| --- | --- |
| N—[(4,6-dimethylpyrimidin-2-yl)aminocarbonyl]-2,3-dihydro-2-methyl-7-benzothiophenesulfonamide, 1,1-dioxide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 22

| Oil Suspension | |
| --- | --- |
| N—[(4-methoxy-6-methylpyrimidin-2-yl)aminocarbonyl]-2,3-dihydro-2-methyl-7-benzothiophenesulfonamide, 1,1-dioxide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 23

| Wettable Powder | |
| --- | --- |
| N—[(4,6-dimethoxypyrimidin-2-yl)aminocarbonyl]-2,3-dihydro-2-methyl-7-benzothiophenesulfonamide, 1,1-dioxide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 24

| Low Strength Granule | |
| --- | --- |
| N—[(4,6-dimethyl-1,3,5-triazin-2-yl)aminocarbonyl]-2,3-dihydro-2-methyl-7-benzothiophenesulfonamide, 1,1-dioxide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 25

| Granule | |
| --- | --- |
| N—[(4-methoxy-6-methyl-1,3,5-triazin-2-yl)aminocar- | 80% |

-continued

| Granule | |
|---|---|
| bonyl]-2,3-dihydro-2-methyl-7-benzofuransulfonamide 1,1-dioxide | |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 26

| High Strength Concentrate | |
|---|---|
| N—[(4,6-dimethoxy-1,3,5-triazin-2-yl)aminocarbonyl]-2,3-dihydro-2-methyl-7-benzothiophenesulfonamide 1,1-dioxide | 99% |
| silica aerogel | 0.5% |
| synthetic amorphous silica | 0.5% |

The ingredients are blended and ground in a hammermill to produce a material essentially all passing a U.S.S. No. 50 screen (0.3 mm opening). The concentrate may be formulated further if necessary.

Utility

The compounds of the present invention are effective herbicides. They have utility for broadspectrum pre- and/or post-emergence weed control in areas where complete control of all vegetation is desired, such as around fuel storage tanks, ammunition depots, industrial storage areas, parking lots, drive-in theaters, around billboards, highway and railroad structures, or on fallow land.

The rates of application for the compounds of the invention are determined by a number of factors, including the types of weeds to be controlled, weather and climate, formulations selected, mode of application, amount of foliage present, etc. In general terms, the subject compounds should be applied at levels of around 0.005 to 5 kg/ha, the lower rates being suggested for use on lighter soils and/or those having a low organic matter content, or for situations where only short-term persistence is required.

The compounds of the invention may be used in combination with any other commercial herbicide examples of which are those of the triazine, triazole, uracil, urea, amide, diphenylether, carbamate, acetanilide, bipyridylium, dinitroaniline and phenolic types.

The herbicidal properties of the subject compounds were discovered in a number of greenhouse tests. The test procedure and results follow.

Test A

Seeds of crabgrass (*Digitaria* sp.), barnyardgrass (*Echinocholoa crusgalli*), wild oats (*Avena fatua*), sicklepod (*Cassia obtusifolia*), morningglory (*Ipomoea* sp.), cocklebur (*Xanthium pensylvanicum*), sorghum, corn, soybean, sugar beet, rice, wheat and purple nutsedge (*Cyperus rotundus*) tubers were planted and treated pre-emergence with the chemicals dissolved in a non-phytotoxic solvent. At the same time, these crop and weed species, along with cotton and bush bean, were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

A=growth acceleration;
C=chlorosis/necrosis;
D=defoliation;
E=emergence inhibition;
G=growth retardation;
H=formative effects;
U=unusual pigmentation;
X=axillary stimulation; and
6Y=abscised buds or flowers.

It will be seen that the compounds have high pre- and post-emergence activity at the low rates of application selected for this evaluation. A few compounds, e.g., Compounds 26, 29, 46, 47 and 52, have low activity at the very low rates of application selected for this test. It is reasonable to assume that these compounds would exhibit higher activity at higher use rates.

Table A Structures

-continued
Table A Structures
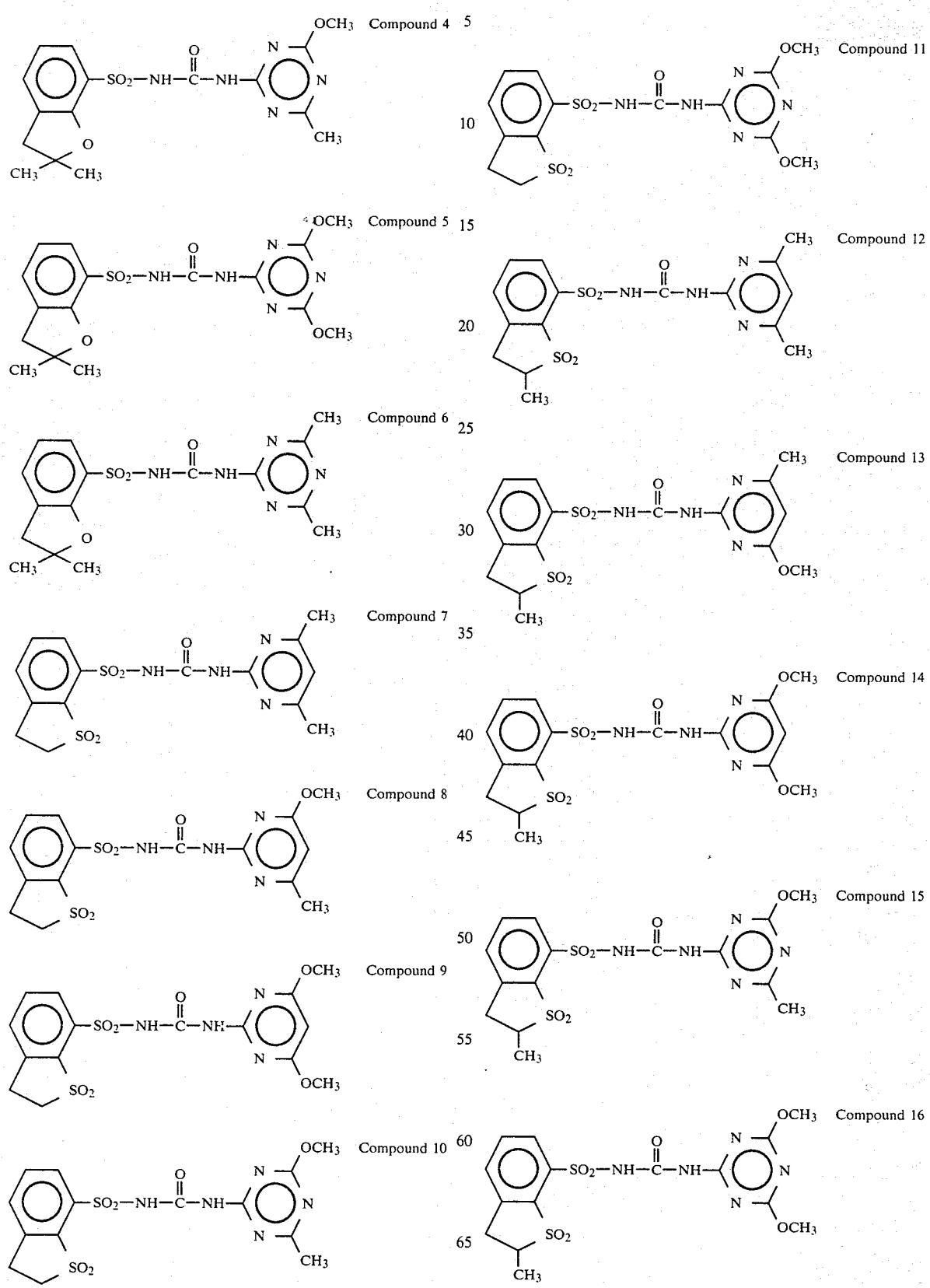

-continued
Table A Structures
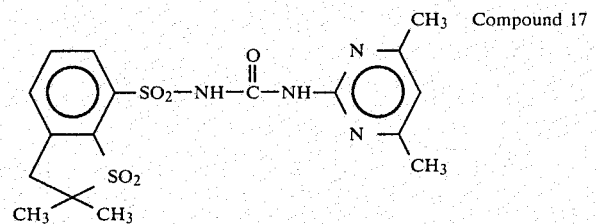
Compound 17
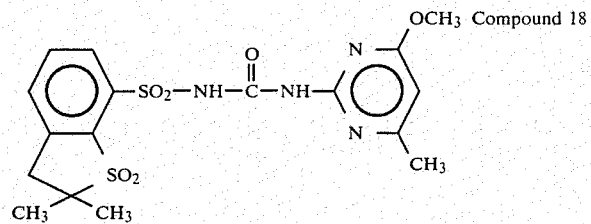
Compound 18
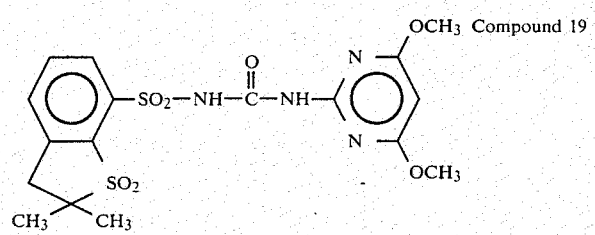
Compound 19
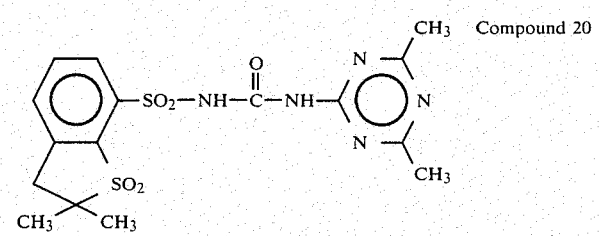
Compound 20
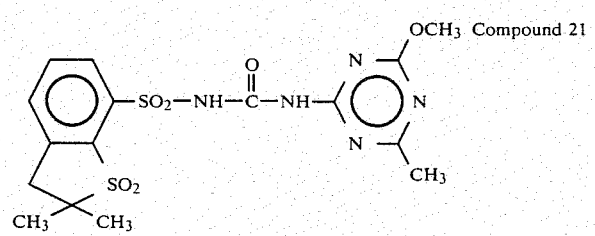
Compound 21
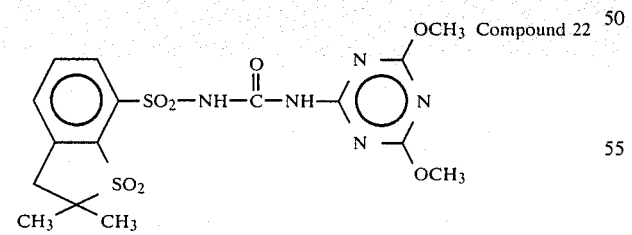
Compound 22
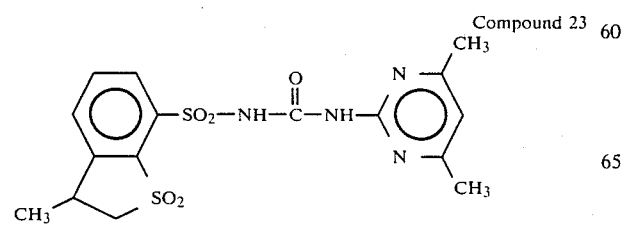
Compound 23
-continued
Table A Structures
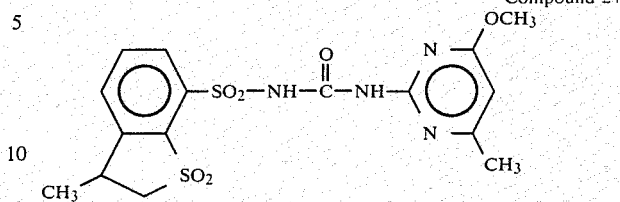
Compound 24
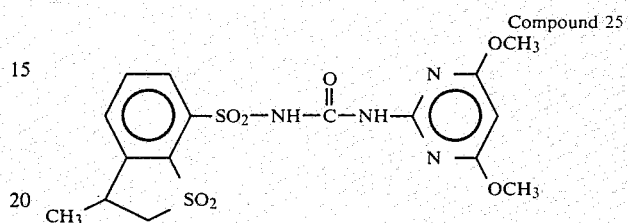
Compound 25
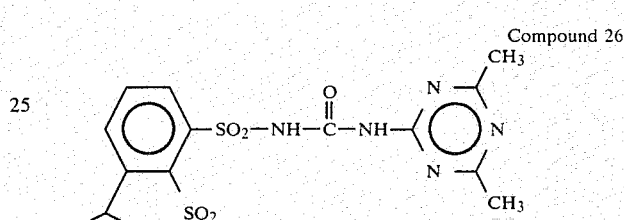
Compound 26
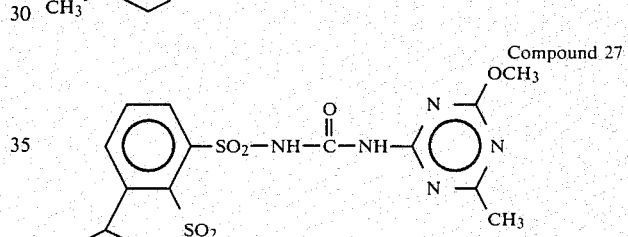
Compound 27
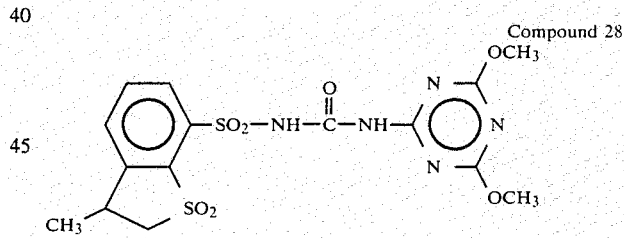
Compound 28
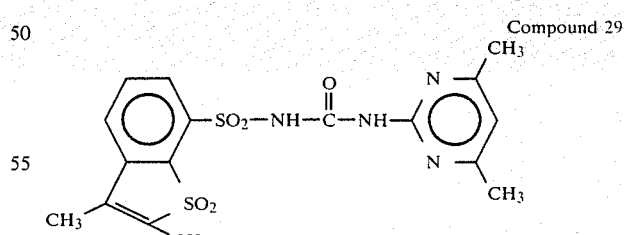
Compound 29
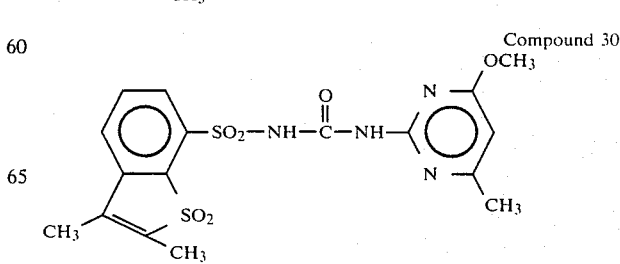
Compound 30

-continued
Table A Structures
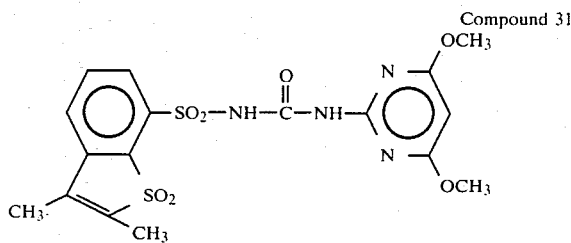
Compound 31
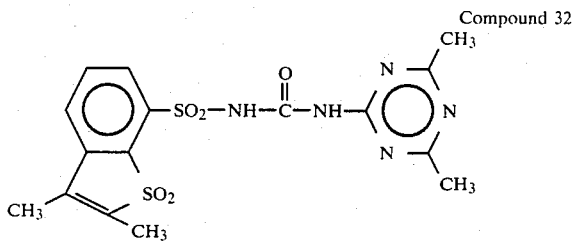
Compound 32
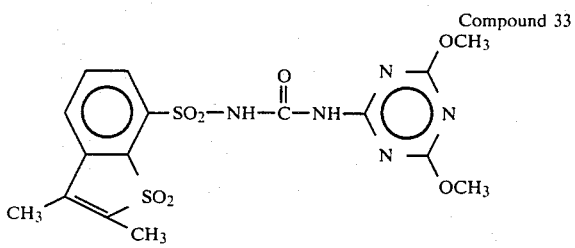
Compound 33
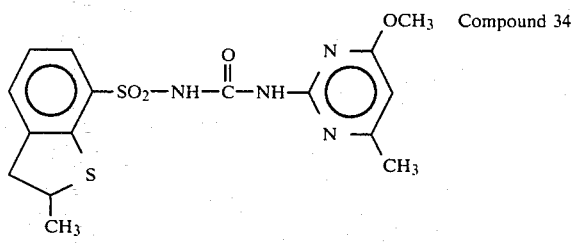
Compound 34
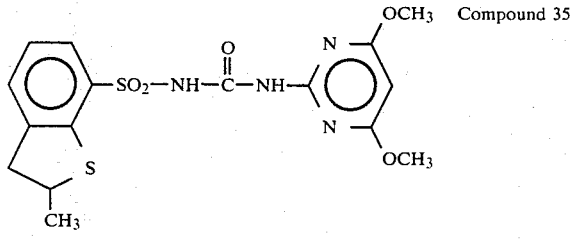
Compound 35
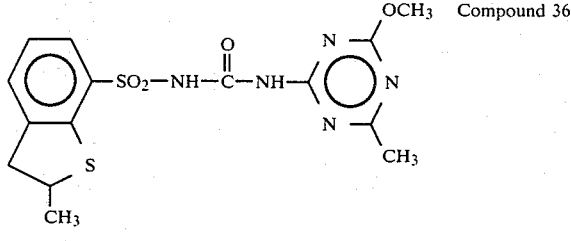
Compound 36
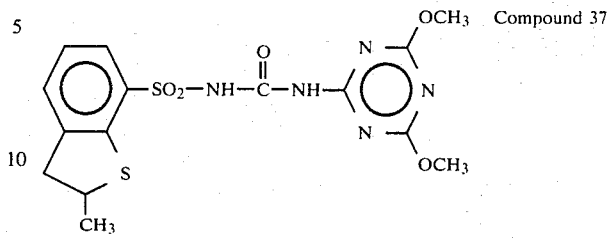
Compound 37
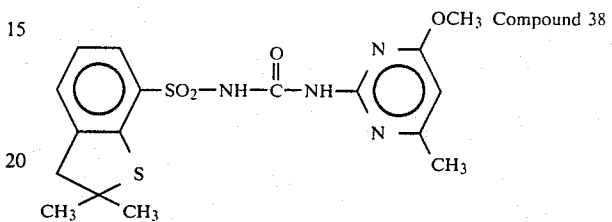
Compound 38
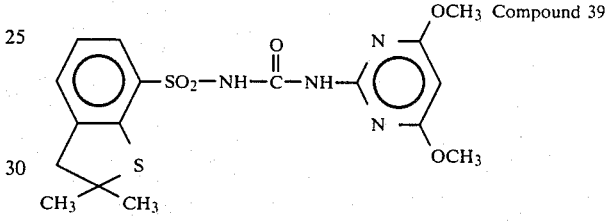
Compound 39
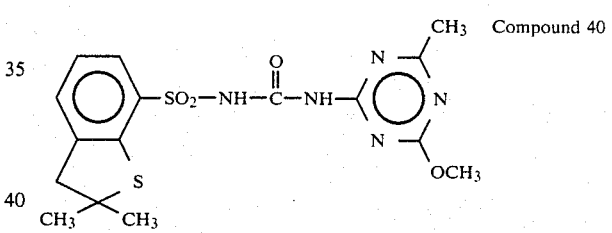
Compound 40
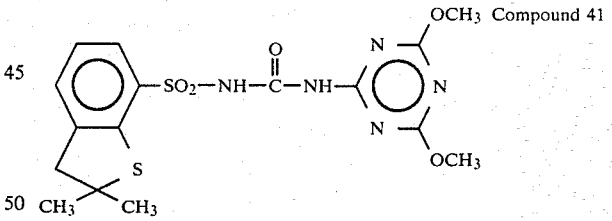
Compound 41
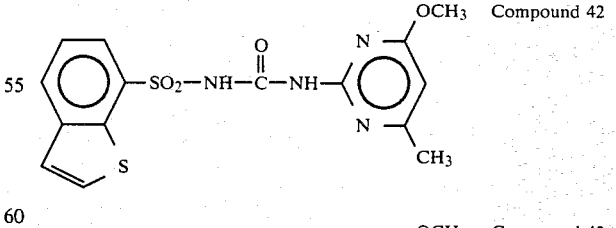
Compound 42
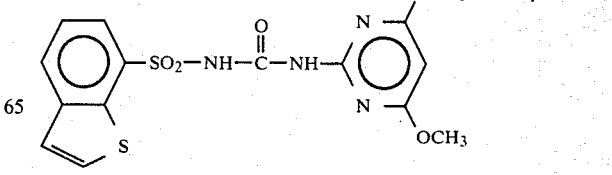
Compound 43

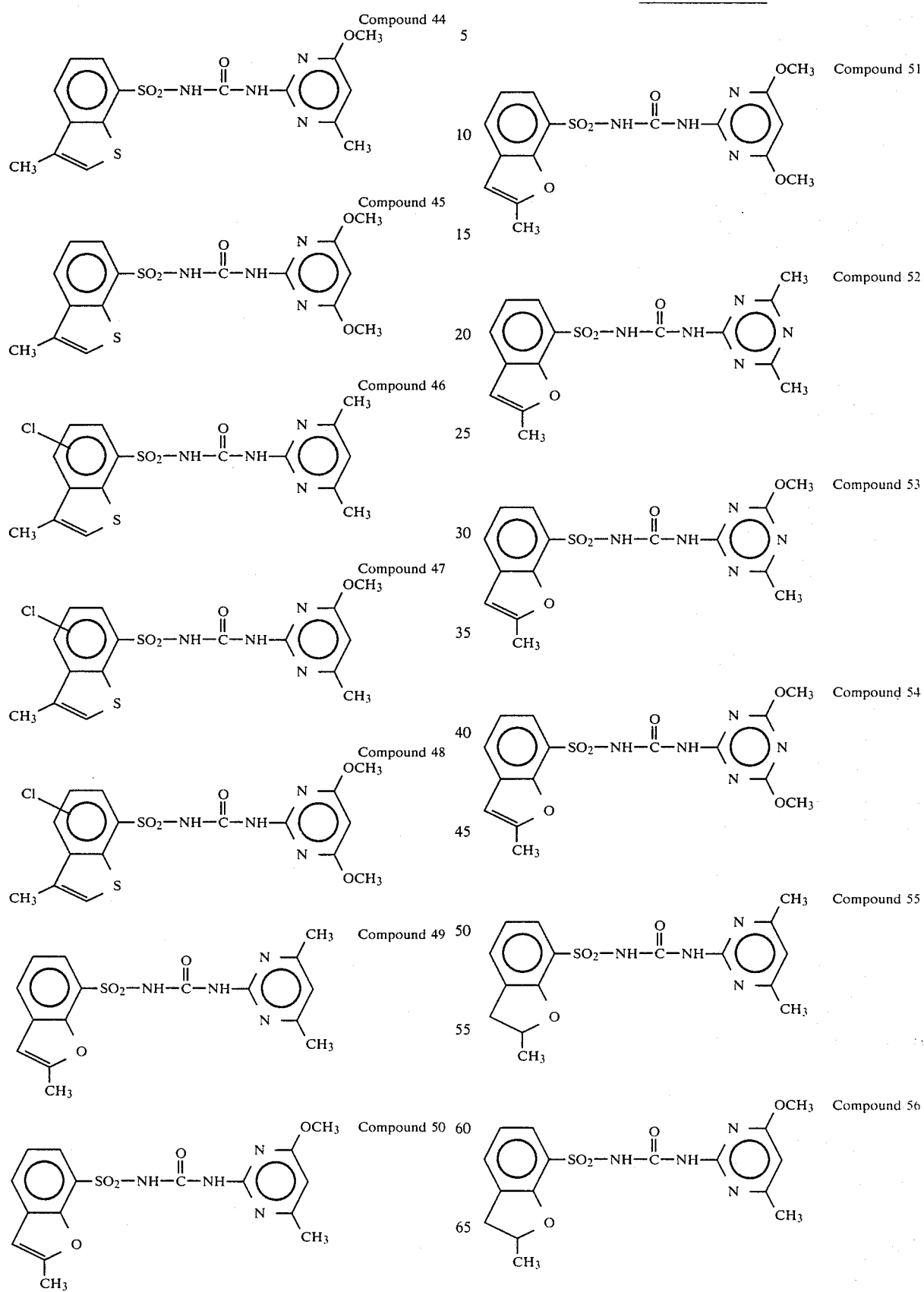

-continued
Table A Structures
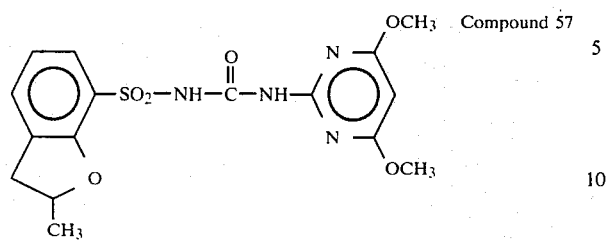
Compound 57
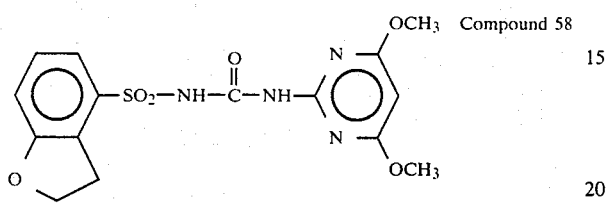
Compound 58

TABLE A

| | Structure No. | | | | | | | | | | | | | Cmpd. |
|---|---|---|---|---|---|---|---|---|---|---|---|---|---|---|
| | 1 | 2 | 3 | 4 | 5 | 6 | Cmpd. 7 | Compound 8 | Compound 9 | Compound 10 | Cmpd. 11 | Cmpd. 12 | Cmpd. 13 | 14 |
| Rate kg/ha | 0.05 | 0.05 | 0.05 | 0.05 | 0.05 | 0.05 | 0.05 | 0.4 | 0.05 | 0.4 | 0.05 | 0.4 | 0.05 | 0.05 | 0.05 |
| | | | | | | | POST-EMERGENCE | | | | | | | | |
| Bush bean | 3C,8G,6Y | 6C,9G | 6C,9G,6Y | 9C | 9C | 3C,9G,6Y | 5C,9G,6Y | 9C | 6C,9G,6Y | 6C,9G,6Y | 4C,9G | 9C | 5C,9G | 9C |
| Cotton | 3C,3H,9G | 6C,9G | 6C,9G | 6C,9G | 9C | 2C,5G | 5C,9G | 9C | 10C | 5C,9G | 9C | 4C,8G | 6C,9G | 5C,9G |
| Morningglory | 2C,9G | 3C,9H | 6C,9G | 10C | 9C | 2C | 4C,9G | 10C | 10C | 4C,8G | 9C | 9C | 9C | 9C |
| Cocklebur | 5G | 10C | 9C | 9C | 10C | 2C | 3C,8G | 9C | 9C | 3C,7G | 9C | 5C,9G | 9C | 10C |
| Sicklepod | 1C,5G | 6C,9G | 4C,8H | 4C,7H | 2C,8H | 2A | 9G | 9C | 9G | 0 | 4C,9G | 4C,8G | 9C | 6C,9G |
| Nutsedge | 4G | 6C,9G | 2C,8G | 7X | 3C,6G | 0 | 4C,9G | 7C,9G | 9G | 2C,8G | 7G | 5C,9G | 9C | 7C,9G |
| Crabgrass | 4G | 6C,9G | 2C,7G | 3C,8G | 2C,8G | 2C,7H | 9C | 6C,9G | 7C,9G | 4C,9G | 4C,9G | 5C,9G | 6C,9H | 9C |
| Barnyardgrass | 2C,9H | 10C | 10C | 9C | 9C | 1C | 9C | 7C,9G | 6C,9G | 9C | 6C,9G | 9C | 9C | 9C |
| Wild Oats | 2C,6G | 7C,9G | 6C,6G | 6C,9G | 10C | 0 | 9C | 6C,9G | 6C,9G | 6C,9G | 4C,9G | 9C | 10C | 9C |
| Wheat | 2C,8H | 2C,9G | 9C | 9C | 9C | 2C,8H | 4U,9C | 3U,9C | 9C | 4U,9G | 3C,9G | 9C | 9C | 6C,9G |
| Corn | 3C,9G,5X | 10C | 10C | 10C | 6C,9G | 2C,5H | 4C,9G | 5C,9G | 9C | 3C,7G | 5C,9G | 5C,9G | 10C | 9C |
| Soybean | 2C,9H | 5C,9G | 4C,9G | 6C,9G | 6C,9G | 6G | 5C,9G | 5C,9G | 5C,9G | 4C,9G | 2C,9G | 5U,9C | 6C,9G | 9C |
| Rice | 3C,9H | 5C,9G | 9G | 9C | 10C | 2C,8H | 9C | 4C | 9C | 2C,9G | 9C | 5U,9C | 9C | 9C |
| Sorghum | | | | | | | | | | | | | | |
| Sugar beet | | | | | | | | | | | | | | |

| | Compound 15 | Compound 16 | Compound 17 | Cmpd. 18 | Cmpd. 19 | Compound 20 | Cmpd. 21 | Cmpd. 22 | Compound 23 | Cmpd. 24 | Cmpd. 25 | Compound 26 |
|---|---|---|---|---|---|---|---|---|---|---|---|---|
| Rate kg/ha | 0.4 | 0.05 | 0.05 | 0.05 | 0.05 | 0.05 | 0.4 | 0.05 | 0.4 | 0.05 | 0.05 | 0.05 | 0.05 | 2.0 | 0.05 |
| | | | | | POST-EMERGENCE | | | | | | | |
| Bush bean | 9C | 9C | 6C,9G,6Y | 6C,9G,6Y | 1C | 10D,9G,6Y | 9D,9G,6Y | 0 | 0 | 4C,9G,6Y | 6C,8G,6Y | 0 | 3C,9G,6Y | 3C,9G,6Y | 7C,9G,6Y | 0 |
| Cotton | 4C,9G | 5C,9G | 4C,9G | 4C,9G | 1C,2H | 4C,9C | 4C,9G | 0 | 3C,4G | 4C,8G | 4C,8G | 0 | 3C,4H,9G | 4C,4H,9G | 0 |
| Morningglory | 9C | 4C,8G | 4C,9G | 10C | 2C,3G | 2C,8H | 5C,9G | 0 | 5C,8H | 4C,9H | 0 | 3C,9G | 3C,8G | 3C,8G | 0 |
| Cocklebur | 9C | 4C,9H | 5C,9G | 9C | 2G | 2C,8H | 3C,9G | 0 | 5C,9H | 4C,8H | 0 | 2C,5G | 3C,3H | 0 |
| Sicklepod | 9C | 3C,9G | 2C,8G | 4C,7H | 0 | 2C,3H | 3C,8G | 0 | 2C,4H | 3C,3H | 0 | 3G | 3G | 0 |
| Nutsedge | 9C | 4C,8G | 2C,8G | 3C,8G | 3G | 2C | 2G | 0 | 2C | 0 | 0 | 2G | 0 | 0 |
| Crabgrass | 9C | 9C | 9C | 9C | 0 | 3C,9G | 1C,3G | 0 | 2C,7G | 2C,8G | 0 | 2C,5H | 2H | 0 |
| Barnyardgrass | 9C | 9C | 9C | 9C | 0 | 2C,9G | 10C | 0 | 9C | 9C | 0 | 2G | 6H | 0 |
| Wild Oats | 9C | 7U,9C | 9C | 9C | 0 | 10C | 6C,9G | 0 | 8C | 9C | 0 | 8G | 0 | 0 |
| Wheat | 9C | 5C,9G | 7U,9C | 10C | 5G | 5U,9G | 10C | 0 | 9C | 10C | 0 | 3C,9G | 4G | 0 |
| Corn | 10C | 9C | 5C,9G | 9C | 1C | 9C | 5U,9C | 0 | 7U,9C | 9C | 0 | 3C,9G | 2C,9G | 0 |
| Soybean | 6C,9G | 5C,9G | 6C,9G | 5C,9G | 2G | 5C,9G | 9C | 0 | 4C,8G,5X | 2C,9G | 0 | 3C,9G | 3H,9G | 0 |
| Rice | 9C | 9C | 9C | 9C | 1C | 9C | 5C,9G | 0 | 6C,9G | 5C,9G | 0 | 3C,9G | 6C,9G | 0 |
| Sorghum | 9C | 6C,9G | 9C | 6C,9G | 5G | 5C,9G | 9C | 0 | 5U,9G | 9C | 0 | 3C,9G | 9G | 0 |
| Sugar beet | 9G,7X | 9C | 4G,5X | 9C | 2G | 2C,8H | 9C | 0 | 5C,9G | 9C | 0 | — | — | — |

| | Compound 27 | Compound 28 | Cmpd. 29 | Cmpd. 30 | Cmpd. 31 | Cmpd. 32 | Cmpd. 33 | Cmpd. 34 | Cmpd. 35 | Cmpd. 36 | Cmpd. 37 | Cmpd. 38 | Cmpd. 39 |
|---|---|---|---|---|---|---|---|---|---|---|---|---|---|
| Rate kg/ha | 0.4 | 0.05 | 0.05 | 0.4 | 0.05 | 0.4 | 0.05 | 0.05 | 0.05 | 0.05 | 2.0 | 0.05 | 0.05 | 0.05 | 0.05 |
| | | | | POST-EMERGENCE | | | | | | | | | |
| Bush bean | 5C,9G,6Y | 2C,2H | 6C,9G,6Y | 1C,3G | 1C | 4C,9G,6Y | 9D,9G,6Y | 0 | 4C,9G,6Y | 4C,9G,6Y | 3C,5G,6Y | 5C,9G,6Y | 5C,9G,6Y | 4C,6G,6Y | 5C,9G,6Y |
| Cotton | 4C,8G | 1C | 4C,9G | 1C | 1C | 5C,9G | 5C,9G | 0 | 5C,9G | 4C,9G | 4C,8G | 4C,8G | 4C,8H | 4C,7H | 4C,9G |
| Morningglory | 3C | 1C | 5C,9G | 1C | 1C | 4C,8H | 4C,6H | 0 | 2C | 9C | 4C,8G | 4C,7G | 9C | 4C | 3C,8G |
| Cocklebur | 2C,5H | 1C | 5C,9H | 1C | 0 | 5C,9H | 3C,9G | 0 | 2C | 9C | 4C,9G | 10C | 10C | 3C,8G | 9C |
| Sicklepod | 3C | 1C | 5C,9H | 1C | 0 | 2C,3H | 3C,8G | 0 | 2C | 5C,9G | 3G | 4C,8G | 5C,9G | 2C | 4C,6H |
| Nutsedge | 2G | 0 | 2C,8G | 1C | 2G | 2G | 2G | 0 | 2C,7G | 2G | 2G | 2G | 2G | 2G | 4C,9G |
| Crabgrass | 2G | 0 | 9C | 2G | 1C | 4G | 1C,3G | 0 | 9C | 1C,3G | 0 | 1C,3G | 1C | 2C,8G | 9C |
| Barnyardgrass | 2C,7H | 0 | 5C,9H | 1C | 0 | 2C,8H | 10C | 0 | 8C | 4C,9H | 5G,5X | 4C,9H | 4C,9H | 9C | 9C |
| Wild Oats | 9G,7X | 4G,5X | 5C,9G | 0 | 2G | 0 | 3G | 0 | 3G | 3C,9G | 3H | 3C,9G | 3C,9G | 2C,6G | 9C |

4,514,211

TABLE A-continued

| | Cmpd. 40 | Cmpd. 41 | Cmpd. 42 | Cmpd. 43 | Cmpd. 44 | Cmpd. 45 | Cmpd. 46 | Cmpd. 47 | Cmpd. 48 | Cmpd. 49 | Cmpd. 50 | Cmpd. 51 | Cmpd. 52 | Cmpd. 53 | Cmpd. 54 |
|---|---|---|---|---|---|---|---|---|---|---|---|---|---|---|---|
| Wheat | 10C | 1C,5G | 9C | 0 | 3G | 5G | | 2G | | 9C | 8G | | 2C,9G,5X | 2C,8G | 9C |
| Corn | 9C | 2C,7H | 6U,9C | 0 | 3C,7G | 2C,9H | | 4C,8H | | 9C | 5U,9G | | 3U,9G | 2C,8G | 4U,9C |
| Soybean | 2H,5G | 1C,1H | 3C,5G | 0 | 4C,8G | 5C,9G | | 5C,6G | | 5C,9G | 5C,9G | | 5C,9G | 5C,9G | 4C,9G |
| Rice | 9C | 2U,9G | 9C | 0 | 4C,9G | 6C,9G | | 3C,9G | | 9C | 6C,9G | | 5C,9G | 4C,9H | 6C,9G |
| Sorghum | 9C | 2C,9H | 2U,9G | 2C | 5C,9G | 9G | | 2C,9G | | 9C | 3C,9G | | 2C,9G | 4C,7G | 9C |
| Sugar beet | — | — | — | — | — | — | — | — | — | 5C,9G | 5C,9G | | 9C | | 9C |
| Rate kg/ha | 0.05 | 0.05 | 0.4 | 0.4 | 0.4 | 0.4 | 0.4 | 0.4 | 0.4 | 0.05 | 0.05 | 0.05 | 0.05 | 0.05 | 0.05 |

POST-EMERGENCE

| | Cmpd. 40 | Cmpd. 41 | Cmpd. 42 | Cmpd. 43 | Cmpd. 44 | Cmpd. 45 | Cmpd. 46 | Cmpd. 47 | Cmpd. 48 | Cmpd. 49 | Cmpd. 50 | Cmpd. 51 | Cmpd. 52 | Cmpd. 53 | Cmpd. 54 |
|---|---|---|---|---|---|---|---|---|---|---|---|---|---|---|---|
| Bush bean | 4C,8G,6Y | 4C,9G,6Y | 5C,9G,6Y | 0 | 4C,4G,6Y | 0 | 0 | 6C,9G,6Y | | 5C,8G,6Y | | 4C,7G,6Y | | 9C | 9C |
| Cotton | 4C,7H | 2C,2H | 5C,9G | 0 | 2C | 0 | 0 | 1C | | 2C,5G | 9C | 1C | | 2C,8G | 9C |
| Morningglory | 4C,9G | 4C,8H | 10C | 2C,2H | 2C | 0 | 0 | 1C,2G | | 1C,4G | 4C,8H | 1C | | 3C,6G | 5C,9G |
| Cocklebur | 3C,9H | 4C,9H | 10C | 1C | 3C,8G | 0 | 0 | 1C | | 1C | 9C | 1C | | 3C,6G | 9C |
| Sicklepod | 2C | 2C,3H | 9C | 3C,7H | 2C | 0 | 0 | 0 | | 4C,9G | 9C | 0 | | 5C,9G | 5C,9G |
| Nutsedge | 0 | 0 | 9G | 2G | 0 | 0 | 0 | 0 | | 3C,7G | 10C | 2G | | 1C,5G | 5C,9G |
| Crabgrass | 1C | 2C | 5C,9G | 0 | 0 | 0 | 0 | 0 | | 2G | 2C,6G | 0 | | 2C,5G | 1C,4G |
| Barnyardgrass | 3C,9H | 4C,8H | 5C,9G | 0 | 0 | 0 | 0 | 0 | | 2C,6H | 10C | 0 | | 2C,9H | 3C,9H |
| Wild Oats | 1C,3G | 3C,9G | 9C | 0 | 0 | 0 | 0 | 0 | | 0 | 5G | 0 | | 0 | 1C,5G |
| Wheat | 1C,5G | 2C,5G | 4C,9G | 0 | 0 | 0 | 0 | 0 | | 1C,9G | 5G | 0 | | 2G | 4G |
| Corn | 2C,9G | 1U,9G | 1C,7G | 0 | 0 | 0 | 0 | 1C,2H | | 2C,8G | 2C,9G | 0 | | 1U,9H | 1C,9G |
| Soybean | 4C,9G | 3C,9G | 4U,9G | 0 | 2C,4G | 0 | 0 | 2C,4H | | 9C | 9C | 3C,3H | | 9C | 5C,9G |
| Rice | 6C,9G | 5C,9G | 9C | 2G | 0 | 0 | 0 | 2C,4G | | 3C,9G | 9G | 1C,4G | | 5C,9G | 5C,9G |
| Sorghum | 2C,9G | 2C,9G | 5C,9G | 0 | 2C,4G | 0 | 0 | 3C,8H | | 3C,9G | 2C,9G | 1C,3G | | 1C,9G | 1C,9G |
| Sugar beet | 4C,8G | 3C,5H | 2U,9G | 0 | 0 | 0 | 0 | 0 | | 4C,7G | — | 4C,9G | | 2C,9G | 3C,9G |
| Rate kg/ha | 0.05 | 0.05 | 0.4 | 0.4 | 0.4 | 0.4 | 0.4 | 0.4 | 0.4 | 0.05 | 0.05 | 0.05 | 0.4 | 0.05 | 0.05 |

| | Cmpd. 55 | Cmpd. 56 | Cmpd. 57 |
|---|---|---|---|

POST-EMERGENCE

| | Cmpd. 55 | Cmpd. 56 | Cmpd. 57 |
|---|---|---|---|
| Bush bean | 9C | 9C | 5C,8G,6Y |
| Cotton | 4C,8G | 5C,9G | 4C,3H,9G |
| Morningglory | 2C,8H | 5C,9G | 1C,2H |
| Cocklebur | 9C | 4C,5G | 5G |
| Sicklepod | 5C,9G | 10C | 2C,8H |
| Nutsedge | 4C,8G | 4C,8H | 9G |
| Crabgrass | 4C,9G | 9C | 0 |
| Barnyardgrass | 2C,9G | 5C,9G | 2C,8H |
| Wild Oats | 2C,9G | 9C | 0 |
| Wheat | 10C | 10C | 0 |
| Corn | 5C,9G | 9C | 2C,6G |
| Soybean | 5C,9G | 10C | 2C,9G |
| Rice | 9C | 9C | 6G |
| Sorghum | 9C | 10C | 2C,9H |
| Sugar beet | 2C,8H | 9C | — |
| Rate kg/ha | 0.4 | 0.05 | 0.4 |

| Structure No. | 1 | 2 | 3 | 4 | 5 | 6 |
|---|---|---|---|---|---|---|
| Rate kg/ha | 0.05 | 0.05 | 0.05 | 0.05 | 0.05 | 0.05 |

PRE-EMERGENCE

| | 1 | 2 | 3 | 4 | 5 | 6 | Cmpd. 7 | Compound 8 | Compound 9 | Compound 10 | Cmpd. 11 | Cmpd. 12 | Cmpd. 13 | Cmpd. 14 |
|---|---|---|---|---|---|---|---|---|---|---|---|---|---|---|
| Morningglory | 2C,6H | 8G | 9G | 9G | 9G | 2C,5H | 9G | 9C | 5C,9G | 2C,5G | 9G | 9G | 9C | 9C |
| Cocklebur | 8H | 9H | 9H | 9H | 9H | 2C,9H | 3C,8H | 9H | 9H | 5H | 9H | 9H | 9H | 9H |
| Sicklepod | 6G | 7G | 2C,7G | 5C,9G | 5C,9G | 1C | 3C,7G | 9G,4C | 5C,9G | 7G | 5C,9G | 9H | 2C,9G | 9G |

POST-EMERGENCE

| | Compound 8 | Compound 9 | Compound 10 | Cmpd. 11 | Cmpd. 12 | Cmpd. 13 | Cmpd. 14 |
|---|---|---|---|---|---|---|---|
| Bush bean | | | | 9C | 9C | 9C | 9C |
| Cotton | | | | 5C,9G | 9H | 9H | 9H |
| Morningglory | | | | 5C,9G | 5C,9G | 2C,9G | 9G |
| Rate kg/ha | 0.4 | 0.05 | 0.4 | 0.4 | 0.05 | 0.05 | 0.05 |

TABLE A-continued

| Rate kg/ha | Compound 15 0.4 0.05 | Compound 16 0.4 0.05 | Cmpd. 17 0.4 0.05 | Cmpd. 18 0.4 0.05 | Cmpd. 19 0.4 0.05 | Cmpd. 20 0.4 0.05 | Cmpd. 21 0.4 0.05 | Cmpd. 22 2.0 0.05 | Compound 23 2.0 0.05 | Cmpd. 24 0.05 | Cmpd. 25 0.05 | Compound 26 2.0 0.05 |
|---|---|---|---|---|---|---|---|---|---|---|---|---|
| Nutsedge | 3G | 10E | 5G 2C,7G | 3C,8G | 10E | 10E | 10E | 10E | 5G | 2G | 10E | 10E |
| Crabgrass | 1C | 2C,6G | 3C,6G 3C,7H | 3C,7G | 10E | 6C,9G | 6C,9H | 5C,9H | 2C,6G | 2C,6G | 5C,9G | 6C,9H |
| Barnyardgrass | 4C,9H | 5C,9H | 5C,9H 5C,9H | 3C,8H | 10E | 6C,9H | 6C,9H | 5C,8H | 3C,9H | 3C,9H | 4C,9H | 6C,9H |
| Wild Oats | 2C,9H | 4C,9H | 2C,9H 4C,9H | 5C,9G | 9H,7C | 6C,9H | 6C,9H | 5C,9H | 3C,8H | 2C,8H | 4C,8G | 9H |
| Wheat | 9H | 3C,9H | 2C,9G 10H | 3C,9G | 10E | 10E | 10E | 5C,9G | 9G | 1C | 9G | 9H |
| Corn | 1C,9G | 10H | 5C,9G 9H | 2C,9G | 9H | 10H | 10E | 9H | 2U,9G | 2C,7H | 5C,9H | 9H |
| Soybean | 2C | 9H | 5C,9G 6C,9H | 3C,6H | 10E | 10E | 9H | 5C,9G | 2C,8H | 2C,8H | 8H | 10E |
| Rice | 2C | 10E | 5C,9H 10E | 10E | 10E | 10E | 6C,9H | 6C,9H | 1C,1H | 10E | 5C,9H | 10H |
| Sorghum | 2C,8H | 5C,9G | 4C,9H 7C,9H | 4C,8H | 10E | 10E | 10E | 6C,9H | 10E | 9H | 10E | 10E |
| Sugar beet | — | — | — | — | — | — | — | — | 6G | — | — | 6C,9H |

| Rate kg/ha | Compound 27 0.4 0.05 | Compound 28 0.4 0.05 | Cmpd. 29 0.4 | Cmpd. 30 0.4 | Cmpd. 31 0.4 | Cmpd. 32 0.4 | Cmpd. 33 0.4 | Cmpd. 34 0.05 | Cmpd. 35 0.05 | Cmpd. 36 0.05 | Cmpd. 37 0.05 | Cmpd. 38 0.05 | Cmpd. 39 0.05 |
|---|---|---|---|---|---|---|---|---|---|---|---|---|---|
| | PRE-EMERGENCE | | | | | | | | | | | | |
| Morningglory | 9C | 9G | 0 | 9G | 9G | 2G | 3C,8H | 9G,9H | 2H | 0 | 2C,8G | 2C,8H | 9G |
| Cocklebur | 9H | 2C,8H | — | 9H | 8H | 9H | 9H | 5C,9G,9H | 8H | 0 | 8H | — | 9H |
| Sicklepod | 9C | 2G | 0 | 8G | 9G | 2C,6G | 2C,7G | 2C,3H | 1C | 0 | 3C,8H | 4G | 3C,8H |
| Nutsedge | 10E | 2G | 10E | 10E | 10E | 0 | 1H | 0 | 0 | 0 | 2C,6G | 4G | 2C,6G |
| Crabgrass | 7C,9G | 2G | 1C | 2C | 4G | 2C,7G | 2C,5G | 0 | 0 | 0 | 1C | 2G | 1C |
| Barnyardgrass | 3C,8G | 2G | 1C | 2C,6G | 5C,9H | 3C | 2C,9G | 6H | 4G | 0 | 2C,7H | 3C,9H | 4C,9H |
| Wild Oats | 4C,9H | 2G | 2G | 2C,6G | 2C,6G | 2C,9H | 2C,9G | 2C,5G | 5G | 6H | 2C,8H | 2C,8G | 2C,9G |
| Wheat | 0 | 2G | 0 | 2C,6H | 9H | 9C | 6C,9H | 2C,9G | 4G | 2G | 2C,9G | 2C,9H | 2C,9G |
| Corn | 5C,9H | 9G | 2C,5G | 2C,9G | 2C,9H | 2C,9H | 9C | 5C,9H | 5G | 0 | 2C,8G | 2C,9H | 2C,9G |
| Soybean | 10E | 2C,5G | 0 | 2C,6H | 2C,3H | 2C,3H | 2C,9H | 2G | 2G | 2G | 2C,6H | 2C,3H | 2C,5H |
| Rice | 8H | 1H | 1C | 10E | 9H | 10E | 2C,3H | 5C,8H | 0 | 0 | 2C,6G | 2C,6H | 2C,9H |
| Sorghum | 9G,9E | 2G | 2C,3G | 10E | 10E | 10E | 10E | 2G | 2G | 2G | 10E | 9H | 3C,9H |
| Sugar beet | 2C,9G | 1C,4G | 0 | — | 10H | 5C,9G | — | 2C,7G | 0 | 2G | 3C,7H | 3C,9G | 4C,9G |

| Rate kg/ha | Cmpd. 40 0.05 | Cmpd. 41 0.05 | Cmpd. 42 0.4 | Cmpd. 43 0.4 | Cmpd. 44 0.4 | Cmpd. 45 0.4 | Cmpd. 46 0.4 | Cmpd. 47 0.4 | Cmpd. 48 0.4 | Cmpd. 49 0.05 | Cmpd. 50 0.05 | Cmpd. 51 0.05 | Cmpd. 52 0.05 | Cmpd. 53 0.05 | Cmpd. 54 0.05 |
|---|---|---|---|---|---|---|---|---|---|---|---|---|---|---|---|
| | | | | | | | PRE-EMERGENCE | | | | | | | | |
| Morningglory | 3C,8G | 8G | 9G | 8G | 8G | 2G | 0 | 0 | 0 | 0 | 9C | 9G | 1C | 9G | 9G |
| Cocklebur | 9H | 8H | 9H | 8H | 8H | 8H | 0 | 0 | — | 3H | — | — | 0 | 9H | 9H |
| Sicklepod | 2C,5G | 7G | 9G | 5G | 5G | 5G | 8H | 0 | 0 | 9G | 9G | 9G | 1C | 8G | 9G |
| Nutsedge | 0 | 2G | 10E | 5G | 10E | 0 | 0 | 0 | 0 | 10E | 10C | 10E | 0 | 9G | 8G |

TABLE A-continued

| | | | | | | | | | | | | |
|---|---|---|---|---|---|---|---|---|---|---|---|---|
| Crabgrass | 1C | 1C | 10E | 5C,9G | 0 | 0 | 0 | 2G | 8G | 2G | 2G | 0 |
| Barnyardgrass | 5C,8H | 4C,8H | 5C,9H | 5C,9H | 3C | 2C | 0 | 1C | 9H | 1C | 3C | 2C,7H |
| Wild Oats | 3C,7G | 2C,8G | 5C,9H | 4C,8G | 0 | 0 | 0 | 1C | 3C,8H | 0 | 2C,4G | 2C,6G |
| Wheat | 7G | 2C,7G | 9H | 8G | 1C | 1C | 0 | 1C,5G | 8G | 0 | 6G | 6G |
| Corn | 2C,9G | 2C,9G | 9H | 3C,9G | 3C | 2C | 0 | 1C,5G | 2C,9G | 0 | 1C,9G | 1C,9G |
| Soybean | 3C,6H | 2C,4H | 9H | 9H | 2C | 0 | 0 | 0 | 7H | 0 | 7H | 9H |
| Rice | 10E | 10E | 8H | 9H | 0 | 1H | 1H | 2G | 9H | 0 | 10E | 10E |
| Sorghum | 2C,9H | 2C,9H | 10E | 5C,9G | 2C,5G | 3C,8H | 0 | 3C,5G | 5C,9H | 2G | 2C,8H | 2C,9H |
| Sugar beet | 4C,9G | 3C,9G | 10E | 10E | 1C | 3C,5H | 0 | 2G | — | 1C | 10E | 10E |

| | Cmpd. 55 | Cmpd. 56 | Cmpd. 57 | Cmpd. 58 |
|---|---|---|---|---|
| Rate kg/ha | 0.05 | 0.05 | 0.05 | 0.4 |
| PRE-EMERGENCE | | | | |
| Morningglory | 10C | 9H | 8H | 6G |
| Cocklebur | 9H | 9H | 9H | 8H |
| Sicklepod | 2C,9G | 9G | 9G | 5G |
| Nutsedge | 10E | 10E | 10E | 2C,8G |
| Crabgrass | 1C | 8G | 8G | 1C |
| Barnyardgrass | 2C,9H | 9H | 9H | 3C,6H |
| Wild Oats | 2C,9H | 6C,9G | 5C,9G | 2C,6C |
| Wheat | 5C,9H | 10C | 10E | 0 |
| Corn | 5C,9H | 10H | 5C,9H | 2C,7G |
| Soybean | 2C,8H | 9H | 2C,8H | 2H |
| Rice | 10E | 10E | 10E | 5G |
| Sorghum | 3C,9H | 6C,9H | 9H | 2C,5G |
| Sugar beet | 9G | 10E | 10E | — |

TEST B

Two plastic bulb pans were filled with fertilized and limed Woodstown sandy loam. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea* spp.), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B. Note that the compounds are highly active when applied as a pre-emergence treatment at low rates of application to soil.

Test C

The test chemicals, dissolved in a non-phytotoxic solvent, were applied in an overall spray to the foliage and surrounding soil of selected plant species. One day after treatment, plants were observed for rapid burn injury. Approximately fourteen days after treatment, all species were visually compared to untreated controls and rated for response to treatment. The rating system was as described previously for Test A. The data are presented in Table C.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), sicklepod (*Cassia obtusifolia*), morningglory (*Ipomoea hederacea*), jimsonweed (*Datura stramonium*), cocklebur (*Xanthium pensylvanicum*), crabgrass (*Digitaria* sp.), nutsedge (*Cyperus rotundus*), barnyardgrass (*Echinochola crusgalli*), giant foxtail (*Setaria faberii*) and wild oats (*Avena fatua*). The following species were grown in soil in a paper cup (12 cm diameter by 13 cm deep): sunflower, sugarbeets, and mustard. All plants were sprayed approximately 14 days after planting. Additional plant species are sometimes added to this standard test in order to evaluate unusual selectivity.

The compounds tested by this procedure are highly active post-emergence herbicides when one considers the low rates of application selected for this test.

TABLE B

PRE-EMERGENCE ON WOODSTOWN SANDY LOAM

| Rate kg/ha | Compound 3 | | Compound 9 | | Compound 12 | | Compound 25 | | Compound 31 | | | Compound 42 | | Compound 50 | |
|---|---|---|---|---|---|---|---|---|---|---|---|---|---|---|---|
| | 0.03 | 0.120 | 0.25 | 0.06 | 0.015 | 0.06 | 0.125 | 0.03 | 0.05 | 0.125 | 0.03 | 0.125 | 0.03 | 0.125 | 0.03 |
| Crabgrass | 2G | 6G,3H | 10C | 10C | 9G | 9G,9C | 0 | 0 | 0 | 0 | 0 | 9G | 8G | 7G | 2G |
| Barnyardgrass | 7G,3H | 9G,5H | 10C | 9G,9C | 6G | 9G,9C | 5G,3H | 0 | 6G | 4G | 2G | 9G | 8G | 9G,9C | 8G |
| Sorghum | — | — | 10C | 10C | 10C | 10C | 9G,9C | 4G,2H | 9G,9C | 8G,8C | 6G | 10C | 9G | 10C | 9G,9C |
| Wild Oats | 6G | 7G | 9G | 9G | 7G | 9G | 2G | 0 | 0 | 0 | 0 | 8G | 6G | 7G | 7G |
| Johnsongrass | 7G,3H | 8G,3H | 9G,9C | 9G | 8G | 9G | 8G,5H | 6G,3H | 9G | 10C | 6G | 9G | 8G | 8G | 8G |
| Dallisgrass | 7G,3H | 8G,3H | 10C | 10C | 10C | 10C | 3H | 0 | 0 | 0 | 0 | 7C | 5G | 8G | 5G |
| Giant foxtail | 3G | 5G,3H | 10C | 10C | 9G | 9G,9C | 2H | 0 | 4G | 2G | 2G | 9G | 5G | 6G | 2G |
| Ky. bluegrass | 9G,9C | 8G,8C | 9G,9C | 9G,9C | 9G | 9G,9C | 5G,3H | 3G | 7G | 5G | 2G | 9G | 8G | 9G,9C | 8G |
| Cheatgrass | 7G | 8G,8C | 10C | 10C | 9G | 10C | 7G,5H | 0 | 2G | 0 | 0 | 9G | 7G | 9G,9C | 9G |
| Sugar beets | 0 | 5G | 10C | 10C | 9G | 10C | 6G,5H | 2G | 9G,9C | 8G | 4G | 10C | 10C | 10C | 8G |
| Corn | 4G | 6G,5H | 10C | 10C | 7G | 10C | 9G,9C | 2G | 8G,5H | 4G | 2G | 9G | 6G | 9G,9C | 7G,5H |
| Mustard | 9G,8C | 9G,9C | 10C | 10C | 9G | 9G,9C | 8G,8C | 0 | 8G | 5G | 3G | 9G | 9G | 10C | 9G,9C |
| Cocklebur | 4G | 6G,3H | 7G,5H | 6G,3H | 6G | 9G | 7G | 0 | 7G,3C | 5G | 0 | 7G | 6G | — | — |
| Pigweed | 8G | 10C | — | — | — | — | 9G,9C | 2G | — | — | — | — | — | — | — |
| Nutsedge | 3G | 5G | 10C | 10C | 10C | 10C | 0 | 0 | 2G | 0 | 0 | 7G | 4G | 10C | 10C |
| Cotton | 2H | 6G,5H | 8G | 8G | 5G | 7G | 5G,3H | 0 | 2G | 0 | 0 | 9G | 6G | 8G | 7G |
| Morningglory | 3G | 7G,5H | 8G | 8G | 6G | 7G | 7G | 0 | 4G | 0 | 0 | 7G | 4G | 3G | 0 |
| Sicklepod | 3G | 4G | 9G,9C | 8G,8C | 9G | 9G | 6G | 0 | 8G,8C | 5G | 0 | 9G | 9G | 9G | 9G |
| Teaweed | 0 | 5G | 7G | 5G | 2G | 6G | 5G | 2G | 9G | 8G | 0 | 9G | 8G | 8G | 7G |
| Velvetleaf | 2G | 6G,5H | 9G,9C | 8G | 8G | 9G | 5H,5G | 0 | — | — | — | 9G | 9G | 9G | 8G |
| Jimsonweed | 4G,3H | 7G,5H | 10C | 9G | 8G | 9G,9C | 5G | 0 | 4G | 2G | 0 | 9G | 9G | 9G | 8G |
| Soybean | 4G,3H | 6G,5H | 9G | 9G | 6G | 8G,7H | 3G | 0 | 4G | 4G | 3G | 9G | 8G | 7G,7H | 6G,5H |
| Rice | 7G | 8G,5H | 10C | 10C | 10C | 10C | 10C | 4G | 10C | 10C | 10C | 10C | 10C | 10C | 10C |
| Wheat | 4G | 7G,3C | 10C | 10C | 8G | 10C | 2G | 0 | 3G | 0 | 0 | 7G | 3G | 7G | 3G |

TABLE C

Overall Soil-Foliage Treatments

| Rate kg/ha | Compound 4 | | | Compound 13 | | | Compound 27 | | | Compound 30 | |
|---|---|---|---|---|---|---|---|---|---|---|---|
| | 0.06 | 0.015 | 0.004 | 0.06 | 0.015 | 0.004 | 0.25 | 0.06 | 0.015 | 0.25 | 0.06 |
| Soybeans | 9G,5C | 9G,3C | 8G,6C | 10C | 9G,8C | 9G,8C | 1H,6G | 4G | 0 | 7G,8C | 6G,6C |
| Velvetleaf | 9G,5C | 9G | 9G | 10C | 9G | 8G | 6G | 1C | 0 | 6C | 6G |
| Sesbania | 9G,9C | 9G | 10G | 10C | 9G | 8G | 5G | 0 | 0 | 5G,5C | 5G,5C |
| Sicklepod | 8G | 7G | 6G | 7G | 7G | 10C | 7G | 0 | 0 | 2C | 2C |
| Cotton | 2C,9G | 6G | 5G | 8G | 10C | 10C | 5G | 1G | 2G | 8G | 7G |

TABLE C-continued

| | Overall Soil-Foliage Treatments | | | | | | | | | | |
|---|---|---|---|---|---|---|---|---|---|---|---|
| | Compound 4 | | | Compound 13 | | | Compound 27 | | | Compound 30 | |
| Rate kg/ha | 0.06 | 0.015 | 0.004 | 0.06 | 0.015 | 0.004 | 0.25 | 0.06 | 0.015 | 0.25 | 0.06 |
| Morningglory | 9G,5C | 9G | 9G,4C | 10C | 10C | 7G | 8G | 2G | 0 | 9G | 8G |
| Alfalfa | 8G,8C | 8G,6C | 6G | 7G | 9G | 4C,4G | 7G | 4G | 0 | 8G,4C | 8G,4C |
| Jimsonweed | 5G,2C | 8G,2C | 3G | 8G | 8G | 8G | 5G | 5G | 0 | 2G | 2G |
| Cocklebur | 8G | 8G | — | 9G | 9G | 5G | 4G | 1G | — | 10C | 9G |
| Corn | 8G,6U | 8G,2H | 8G,2U | 10C | 10C | 10C | 8C,9G | 7G | 2G | 1G,1H | 1H |
| Crabgrass | 8G | 2G | 0 | 9G | 9G | — | 4G | 3G | 0 | 0 | 0 |
| Rice | 8G,7C | 8G,3C | 5G,3C | 9G,4C | 9G,7C | 9G,8C | 8G,4C | 6G | 0 | 9C | 9G |
| Nutsedge | 0 | 0 | 0 | 8G | 8G,9C | 7G | 3G | 0 | 0 | 0 | 0 |
| Barnyardgrass | 10C | 8G | 8G | 10C | 10C | 8C,9G | 3G | 1G | 0 | 0 | 0 |
| Wheat | 8G | 5G | 2G | 9G,3C | 9G,6C | 9G,3C | 1G | 0 | 0 | 2G | 0 |
| Giant foxtail | 9G | 3G | 0 | 8G | 8G | 9G | 0 | 0 | 0 | 4G | 0 |
| Wild Oats | 7G,2C | 7G | 0 | 9G,3C | 10C | 9G,3C | 1G | 0 | 0 | 0 | 0 |
| Sorghum | 7G,2C | 8G | 8G | 9G,4U | 9G,2U | 9G,2U | 8G | 8G | 4G | 9G | 8G |
| Sunflower | 10C | 10C | 10C | 10C | 9G | 9G | 6G,2H | 3G | 1G | 10C | 10C |
| Mustard | 8G,8C | 7G,4C | 5G,4C | 9G | 10C | 10C | 9G | 8G | 5G | 7G | 2G |
| Johnsongrass | 8G,8U | 7G,3U | 8G | 9G,8U | 10C | 10C | 8G | 7G | 0 | 10U | 1H,9G |
| Sugar beets | 9G | 9G | 6G | — | — | — | 5G,4C | 4G | 0 | 10C | 8G |
| Bindweed | 7G | 0 | 0 | 10C | 7G | 5G | 7G,2C | 5G | 2G | 8G | 4G |

Test D

Plastic pots lined with polyethylene bags were filld with prepared Woodstown sandy loam soil. Seeds of kochia (*Kochia scoparia*), Russian thistle (*Salsola kali*), downy brome (*Bromus tectorum*) and green foxtail (*Setaria lutescens*) were planted. About 10 days later seeds of wheat (*Triticum aestivum*) and wild oats (*Avena fatua*) were added. After an additional 10 days, seeds of wheat, corn and sorghum were planted. The compounds were then diluted with a non-phytotoxic solvent and sprayed over the pots. An untreated control and a solvent-alone control were included for comparison. All treatments were maintained in a greenhouse for 19–22 days at which time the treatments were compared to the controls and the effects visually rated.

The data, presented in Table D, indicate that certain of the test compounds have utility for the control of undesirable vegetation on land which is kept in fallow between cereal crops.

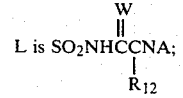   I'

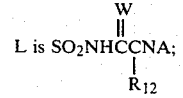   II

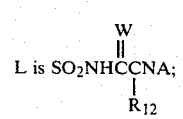   II'

TABLE D

| | Compound Nos. | | | | | | | | | | |
|---|---|---|---|---|---|---|---|---|---|---|---|
| | 7 | | 8 | | 9 | | 12 | | 13 | | 14 |
| Rate, g/ha | 16 | 4 | 16 | 4 | 16 | 4 | 16 | 4 | 16 | 4 | 16 | 4 |
| POST-EMERGENCE | | | | | | | | | | | |
| Russian thistle | 5C | 0 | 10C | 10C | 10C | 7C | 10C | 5G | 10C | 3G | 10C | 10C |
| Kochia | 5G | 0 | 10C | 9G | 10C | 2G | 9C,9G | 4G | 9G | 3G | 10C | 10C |
| Downy brome | 5G | 0 | 8C | 6G | 10C | 8C | 10C | 5G | 9C | 6G | 10C | 10C |
| Green foxtail | 5G | 0 | 8C | 7C | 9C | 6C | 4G | 2G | 5G | 4G | 10C | 7C,9G |
| Wild oats | 5G | 0 | 10C | 9C | 10C | 9C | 10C | 5G | 10C | 4G | 10C | 10C |
| Wheat | 9C | 0 | 10C | 10C | 10C | 10C | 10C | 8G | 10C | 9G | 10C | 10C |
| PRE-EMERGENCE | | | | | | | | | | | |
| Wheat | 0 | 0 | 8G | 0 | 3C,8G | 2G | 8G | 0 | 9C | 3G | 10E | 9G |

What is claimed is:

1. A compound selected from:

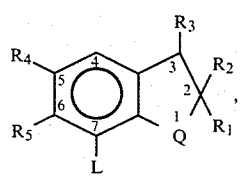   I wherein
Q is O, S, SO or SO$_2$;
Q$_1$ is O, S or SO$_2$

L is SO$_2$NHĊCNA;
  ‖    |
  W    R$_{12}$

R$_1$ is H or C$_1$–C$_4$ alkyl;
R$_2$ is H or C$_1$–C$_4$ alkyl;
R$_3$ is H or CH$_3$;

$R_4$ is H, Cl, $CH_3$, $CF_3$, $OCH_3$, Br, F, $SCH_3$ or $OCF_2H$;

$R_5$ is H, $CH_3$, $OCH_3$, Cl, Br, $NO_2$, $CO_2R_7$, $SO_2R_8$, $OSO_2R_9$, $SO_2NR_{10}R_{11}$, F, $CF_3$, $SCH_3$, $OCF_2H$ or $SO_2N(OCH_3)CH_3$;

$R_6$ is H, Cl, Br of $C_1-C_4$ alkyl;

$R_6'$ is H, $CH_3$, Cl or Br;

$R_7$ is $C_1-C_3$ alkyl, $CH_2CH=CH_2$, $CH_2CH_2OCH_3$ or $CH_2CH_2Cl$;

$R_8$ is $C_1-C_3$ alkyl;

$R_9$ is $C_1-C_3$ alkyl or $CF_3$;

$R_{10}$ and $R_{11}$ are independently $C_1-C_2$ alkyl;

$R_{12}$ is H or $CH_3$;

W is O or S;

A is

[structures]

X is H, $CH_3$, $OCH_3$, Cl, F, $OCF_2H$ or $SCF_2H$;

Y is $CH_3$, $OCH_3$, $OC_2H_5$, $CH_2OCH_3$, $NH_2$, $NHCH_3$, $N(CH_3)_2$, $CH(OCH_3)_2$, $CH(OCH_2CH_3)_2$, $C_2H_5$, $CF_3$, $CH_2=CHCH_2O$,

[structures]

$CH\equiv CCH_2O$, $CF_3CH_2O$, $OCH_2CH_2Cl$, $OCH_2CH_2Br$, $OCH_2CH_2F$, CN, $CH_2OCH_2CH_3$, $OCH_2CH_2OCH_3$ or $GCF_2T$ wherein G is O or S and T is H, CHClF, CHBrF, $CF_2H$ or $CHFCF_3$;

Z is CH, N, $CCH_3$, $CC_2H_5$, CCl or CBr;

$Y_1$ is O or $CH_2$;

$X_1$ is $CH_3$, $OCH_3$, $OC_2H_5$ or $OCF_2H$;

$X_2$ is $CH_3$, $C_2H_5$ or $CH_2CF_3$;

$Y_2$ is $C_2H_5$, $CH_3$, $OCH_3$, $OC_2H_5$, $SCH_3$ or $SC_2H_5$; and $X_3$ is $CH_3$ or $OCH_3$; provided that (1) in Formulae II and II′, when $R_5$ is $NO_2$, then $R_6$ is $C_1-C_4$ alkyl and $R_6'$ is $CH_3$;

(2) when X is Cl or F, then Z is CH and Y is $OCH_3$, $NH_2$, $NHCH_3$, $N(CH_3)_2$ or $OCF_2H$;

(3) when Q is SO, then W is O;

(4) when $R_4$ is other than H, then $R_5$ is H; and (5) $R_1$ and $R_2$ taken together are not more than four carbon atoms.

2. Compounds of claim 1, Formula I.

3. Compounds of claim 2 where W is O.

4. Compounds of claim 3 where $R_5$ is H, Cl, $CH_3$, $OCH_3$, $CO_2R_7$ or $SO_2R_8$, $R_4$ is H, Cl, $CH_3$ or $OCH_3$, and Y is $CH_3$, $OCH_3$, $OC_2H_5$, $CH_2OCH_3$, $NH_2$, $NHCH_3$, $N(CH_3)_2$, $CH(OCH_3)_2$,

[structure]

$C_2H_5$, $CF_3$, $CH_2=CHCH_2O$, $HC\equiv CCH_2O$, $CF_3CH_2O$, $OCF_2H$ or $SCF_2H$.

5. Compounds of claim 4 where $R_3$, $R_4$, $R_5$ and $R_{12}$ are H, $R_1$ is H, $CH_3$ or $CH_2CH_3$ and $R_2$ is H or $CH_3$.

6. Compounds of claim 5 where A is

[structure]

Z is CH or N; and X is $CH_3$, $OCH_3$ or Cl.

7. Compounds of claim 6 where Y is $CH_3$, $OCH_3$, $CH_2OCH_3$ or $N(CH_3)_2$.

8. Compounds of claim 1, Formula I′.

9. Compounds of claim 8 where W is O and Q is S or O.

10. Compound of claim 9 where $R_5$ is H, Cl, $CH_3$, $OCH_3$, $CO_2R_7$ or $SO_2R_8$; and Y is $CH_3$, $OCH_3$, $OC_2H_5$, $CH_2OCH_3$, $NH_2$, $NHCH_3$, $N(CH_3)_2$, $CH(OCH_3)_2$,

[structure]

$C_2H_5$, $CF_3$, $CH_2=CHCH_2O$, $HC\equiv CCH_2O$, $CF_3CH_2O$, $OCF_2H$ or $SCF_2H$.

11. Compounds of claim 10 where $R_5$ and $R_{12}$ are H and $R_1$ and $R_2$ are independently H or $CH_3$.

12. Compounds of claim 11 where A is

[structure]

Z is CH or N; and X is $CH_3$, $OCH_3$ or Cl.

13. Compounds of claim 12 where Y is $CH_3$, $OCH_3$, $CH_2OCH_3$ or $N(CH_3)_2$.

14. Compounds of claim 1, Formula II.

15. Compounds of claim 14 where W is O, $R_6$ is H, $CH_3$ or $CH_2CH_3$ and $R_6'$ is H.

16. Compounds of claim 15 where $R_5$ is H, Cl, $CH_3$, $OCH_3$, $CO_2R_7$ or $SO_2R_8$, $R_4$ is H, Cl, $CH_3$ or $OCH_3$, and Y is $CH_3$, $OCH_3$, $OC_2H_5$, $CH_2OCH_3$, $NH_2$, $NHCH_3$, $N(CH_3)_2$, $CH(OCH_3)_2$,

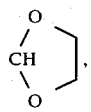

$C_2H_5$, $CF_3$, $CH_2=CHCH_2O$, $HC\equiv CCH_2O$, $CF_3CH_2O$, $OCF_2H$ or $SCF_2H$.

17. Compounds of claim 16 where $R_4$, $R_5$, $R_6'$ and $R_{12}$ are H and $R_6$ is H or $CH_3$.

18. Compounds of claim 17 where A is

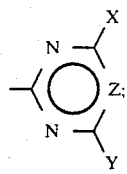

Z is CH or N; and X is $CH_3$, $OCH_3$ or Cl.

19. Compounds of claim 18 where Y is $CH_3$, $OCH_3$, $CH_2OCH_3$ or $N(CH_3)_2$.

20. Compounds of claim 1, Formula II'.

21. Compounds of claim 20 where W is O, Q is O or S, $R_6$ is H or $CH_3$ and $R_6'$ is H or $CH_3$.

22. Compounds of claim 21 where $R_5$ is H, Cl, $CH_3$, $OCH_3$, $CO_2R_7$ or $SO_2R_8$; and Y is $CH_3$, $OCH_3$, $OC_2H_5$, $CH_2OCH_3$, $NH_2$, $NHCH_3$, $N(CH_3)_2$, $CH(OCH_3)_2$,

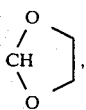

$C_2H_5$, $CF_3$, $CH_2=CHCH_2O$, $HC\equiv CCH_2O$, $CF_3CH_2O$, $OCF_2H$ or $SCF_2H$.

23. Compounds of claim 22 where $R_5$ and $R_{12}$ are H.

24. Compounds of claim 23 where A is

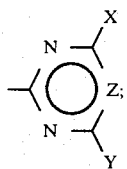

Z is CH or N; and X is $CH_3$, $OCH_3$ or Cl.

25. Compounds of claim 24 where Y is $CH_3$, $OCH_3$, $CH_2OCH_3$ or $N(CH_3)_2$.

26. The compound of claim 1 which is N-[(4,6-dimethylpyrimidin-2-yl)aminocarbonyl]-2,3-dihydro-2-methyl-7-benzothiophenesulfonamide, 1,1-dioxide.

27. The compound of claim 1 which is N-[(4-methoxy-6-methylpyrimidin-2-yl)aminocarbonyl]-2,3-dihydro-2-methyl-7-benzothiophenesulfonamide, 1,1-dioxide.

28. The compound of claim 1 which is N-[(4,6-dimethoxypyrimidin-2-yl)aminocarbonyl]-2,3-dihydro-2-methyl-7-benzothiophenesulfonamide, 1,1-dioxide.

29. The compound of claim 1 which is N-[(4-methoxy-6-methyl-1,3,5-triazin-2-yl)aminocarbonyl]-2,3-dihydro-2-methyl-7-benzothiophenesulfonamide, 1,1-dioxide.

30. The compound of claim 1 which is N-[(4,6-dimethoxy-1,3,5-triazin-2-yl)aminocarbonyl]-2,3-dihydro-2-methyl-7-benzothiophenesulfonamide, 1,1-dioxide.

31. The compound of claim 1 which is N-[(4,6-dimethoxypyrimidin-2-yl)aminocarbonyl]-2,3-dihydro-7-benzothiophenesulfonamide, 1,1-dioxide.

32. The compound of claim 1 which is N-[(4,6-dimethoxypyrimidin-2-yl)aminocarbonyl]-2,3-dihydro-2,2-dimethyl-7-benzothiophenesulfonamide, 1,1-dioxide.

33. The compound of claim 1 which is N-[(4,6-dimethylpyrimidin-2-yl)methylaminocarbonyl]-2,3-dihydro-2-methyl-7-benzothiophenesulfonamide, 1,1-dioxide.

34. A composition suitable for controlling the growth of undesired vegetation which comprises an effective amount of a compound of claim 1 and at least one of the following: surfactant, solid or liquid diluent.

35. A composition suitable for controlling the growth of undesired vegetation which comprises an effective amount of a compound of claim 2 and at least one of the following: surfactant, solid or liquid diluent.

36. A composition suitable for controlling the growth of undesired vegetation which comprises an effective amount of a compound of claim 3 and at least one of the following: surfactant, solid or liquid diluent.

37. A composition suitable for controlling the growth of undesired vegetation which comprises an effective amount of a compound of claim 4 and at least one of the following: surfactant, solid or liquid diluent.

38. A composition suitable for controlling the growth of undesired vegetation which comprises an effective amount of a compound of claim 5 and at least one of the following: surfactant, solid or liquid diluent.

39. A composition suitable for controlling the growth of undesired vegetation which comprises an effective amount of a compound of claim 6 and at least one of the following: surfactant, solid or liquid diluent.

40. A composition suitable for controlling the growth of undesired vegetation which comprises an effective amount of a compound of claim 7 and at least one of the following: surfactant, solid or liquid diluent.

41. A composition suitable for controlling the growth of undesired vegetation which comprises an effective amount of a compound of claim 8 and at least one of the following: surfactant, solid or liquid diluent.

42. A method for controlling the growth of undesired vegetation which comprises applying to the locus to be protected an effective amount of a compound of claim 1.

43. A method for controlling the growth of undesired vegetation which comprises applying to the locus to be protected an effective amount of a compound of claim 2.

44. A method for controlling the growth of undesired vegetation which comprises applying to the locus to be protected an effective amount of a compound of claim 3.

45. A method for controlling the growth of undesired vegetation which comprises applying to the locus to be protected an effective amount of a compound of claim 4.

46. A method for controlling the growth of undesired vegetation which comprises applying to the locus to be protected an effective amount of a compound of claim 5.

47. A method for controlling the growth of undesired vegetation which comprises applying to the locus to be protected an effective amount of a compound of claim 6.

48. A method for controlling the growth of undesired vegetation which comprises applying to the locus to be protected an effective amount of a compound of claim 7.

49. A method for controlling the growth of undesired vegetation which comprises applying to the locus to be protected an effective amount of a compound of claim 8.

50. The compound (2,3-dihydro-N-[(4-methoxy-6-methylthio-1,3,5-triazin-2-yl)aminocarbonyl]-2-methyl-benzo[b]thiophene-7-sulfonamide, 1,1-dioxide).

51. The compound of claim 1, N-(2,3-dihydro-2-methylbenzo[b]furan-7-yl-sulfonyl)-N'-(4,6-dimethyl-pyrimidin-2-yl)urea.

52. The compound of claim 1, N-(2,3-dihydro-2-methylbenzo[b]furan-7-yl-sulfonyl)-N'-(4-methoxy-6-methylpyrimidin-2-yl)urea.

* * * * *